United States Patent
Ibarra et al.

(10) Patent No.: US 9,603,717 B2
(45) Date of Patent: Mar. 28, 2017

(54) SYSTEM AND METHOD FOR AN EXPANDABLE INTERVERTEBRAL IMPLANT

(71) Applicants: Matthew Ibarra, Lakewood, CA (US); Aaron Ricica, Brookline, MA (US); Lin Yin, Brookline, MA (US)

(72) Inventors: Matthew Ibarra, Lakewood, CA (US); Aaron Ricica, Brookline, MA (US); Lin Yin, Brookline, MA (US)

(73) Assignee: SPINEFRONTIER, INC, Malden, MA (US)

( * ) Notice: Subject to any disclaimer, the term of this patent is extended or adjusted under 35 U.S.C. 154(b) by 0 days.

(21) Appl. No.: 14/320,763

(22) Filed: Jul. 1, 2014

(65) Prior Publication Data

US 2015/0012097 A1    Jan. 8, 2015

Related U.S. Application Data

(60) Provisional application No. 61/842,729, filed on Jul. 3, 2013.

(51) Int. Cl.
  *A61F 2/44* (2006.01)
  *A61F 2/46* (2006.01)
  (Continued)

(52) U.S. Cl.
  CPC .............. *A61F 2/447* (2013.01); *A61F 2/442* (2013.01); *A61F 2/4611* (2013.01);
  (Continued)

(58) Field of Classification Search
  CPC ........ A61F 2/447; A61F 2/442; A61F 2/4611; A61F 2002/30482; A61F 2002/2817; A61F 2002/2835; A61F 2002/30062; A61F 2002/30266; A61F 2002/30397; A61F 2002/30405; A61F 2002/30411;
  (Continued)

(56) References Cited

U.S. PATENT DOCUMENTS

2007/0162129 A1* 7/2007 Edie ...................... A61F 2/4465
                                                            623/17.11
2012/0130494 A1* 5/2012 Delurio ................. A61F 2/4465
                                                            623/17.16

(Continued)

*Primary Examiner* — Pedro Philogene
(74) *Attorney, Agent, or Firm* — AKC Patents, LLC; Aliki K. Collins

(57) ABSTRACT

An expandable intervertebral implant includes a base body, a top endplate and a center component. The top endplate is configured to be placed onto an open top of the base body and to expand upward. The top endplate includes a plate, first and second side protrusions extending vertically downward from first and second sides of the plate, respectively, first and second protrusions including inclined surfaces and extending obliquely downward from a first end of the plate and third and fourth protrusions having a triangular shape with at least one inclined surface and extending downward from a second end of the plate. The center component is configured to be placed within the base body and to interface with the top endplate and to move longitudinally forward or backward within the base body, thereby causing the top endplate to expand upwards or move downward, respectively.

21 Claims, 42 Drawing Sheets

(51) Int. Cl.
  *A61F 2/28* (2006.01)
  *A61F 2/30* (2006.01)
(52) U.S. Cl.
  CPC ............ *A61F 2002/2817* (2013.01); *A61F 2002/2835* (2013.01); *A61F 2002/3056* (2013.01); *A61F 2002/30062* (2013.01); *A61F 2002/3083* (2013.01); *A61F 2002/30266* (2013.01); *A61F 2002/30397* (2013.01); *A61F 2002/30405* (2013.01); *A61F 2002/30411* (2013.01); *A61F 2002/30415* (2013.01); *A61F 2002/30471* (2013.01); *A61F 2002/30472* (2013.01); *A61F 2002/30482* (2013.01); *A61F 2002/30484* (2013.01); *A61F 2002/30517* (2013.01); *A61F 2002/30523* (2013.01); *A61F 2002/30555* (2013.01); *A61F 2002/30556* (2013.01); *A61F 2002/30579* (2013.01); *A61F 2002/30601* (2013.01); *A61F 2002/30607* (2013.01); *A61F 2002/30828* (2013.01); *A61F 2002/30841* (2013.01); *A61F 2002/30843* (2013.01); *A61F 2002/30904* (2013.01); *A61F 2002/4475* (2013.01); *A61F 2310/00011* (2013.01); *A61F 2310/00017* (2013.01); *A61F 2310/00023* (2013.01); *A61F 2310/00179* (2013.01); *A61F 2310/00293* (2013.01); *A61F 2310/00371* (2013.01); *A61F 2310/00796* (2013.01)

(58) Field of Classification Search
  CPC .. A61F 2002/30415; A61F 2002/30471; A61F 2002/30472; A61F 2002/30484; A61F 2002/30517; A61F 2002/30523; A61F 2002/30555; A61F 2002/30556; A61F 2002/3056; A61F 2002/30579; A61F 2002/30601; A61F 2002/30607; A61F 2002/30228; A61F 2002/3083; A61F 2002/30841; A61F 2002/30843; A61F 2002/30904; A61F 2002/4475; A61F 2310/00011; A61F 2310/00017; A61F 2310/00023; A61F 2310/00179; A61F 2310/00293; A61F 2310/00371; A61F 2310/00796
  USPC .............. 623/17.11–17.16; 606/86 R, 96, 99
  See application file for complete search history.

(56) References Cited

U.S. PATENT DOCUMENTS

| | | | |
|---|---|---|---|
| 2012/0191194 A1* | 7/2012 | Olmos | A61F 2/4455 623/17.16 |
| 2012/0226357 A1* | 9/2012 | Varela | A61F 2/447 623/17.16 |
| 2013/0006361 A1* | 1/2013 | Glerum | A61F 2/447 623/17.16 |

* cited by examiner

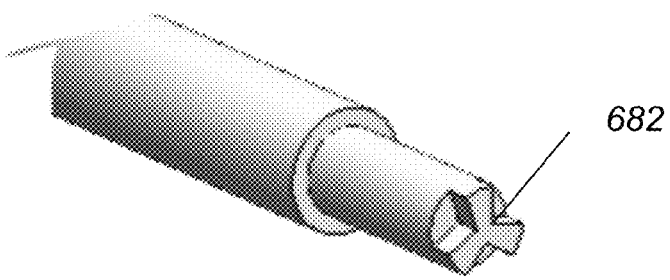
FIG. 32A
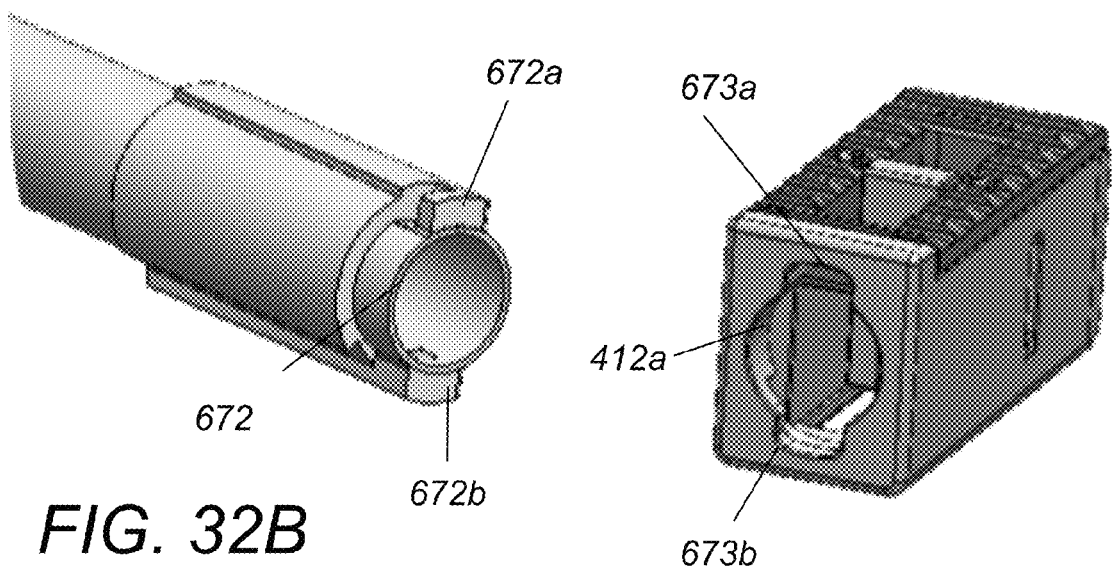
FIG. 32B
FIG. 32C

SYSTEM AND METHOD FOR AN EXPANDABLE INTERVERTEBRAL IMPLANT

CROSS REFERENCE TO RELATED CO-PENDING APPLICATIONS

This application claims the benefit of U.S. provisional application Ser. No. 61/842,729 filed Jul. 3, 2013 and entitled "SYSTEM AND METHOD FOR AN EXPANDABLE INTERVERTEBRAL IMPLANT", the contents of which are expressly incorporated herein by reference.

FIELD OF THE INVENTION

The present invention relates to a system and a method for an intervertebral implant, and more particularly to an intervertebral implant that expands upwards or downwards or both upwards and downwards.

BACKGROUND OF THE INVENTION

The human spine includes individual vertebras that are connected to each other. Under normal circumstances the structures that make up the spine function to protect the neural structures and to allow us to stand erect, bear axial loads, and be flexible for bending and rotation. However, disorders of the spine occur when one or more of these spine structures are abnormal. In these pathologic circumstances, surgery may be tried to restore the spine to normal and to relieve the patient of pain. The goal of spine surgery for a multitude of spinal disorders is often filling of voids within a pathologic vertebral body (exemplified by kyphoplasty or vertebroplasty procedures), replacement of a degenerated intervertebral disc with an intervertebral implant device that preserves mobility (disc replacement) or one that fuses adjacent vertebral segments (interbody and posterolateral fusions). Fusion works well because it stops pain due to movement at the facet joints or intervertebral discs, holds the spine in place after correcting deformity, and prevents instability and or deformity of the spine after spine procedures such as laminectomies or verterbrectomies. However, maintaining spinal mobility between the intervertebral discs and facets may be preferred over fusion in some cases to allow more flexibility of the spine and to decrease the risk of problems above and below the level of the fixation due to increased stress at the adjacent moveable segments.

The common approach to the removal of diseased intervertebral discs or vertebras includes a posterior laminectomy to first decompress the posterior neural elements and to gain access either through a direct posterior approach, or through a transpedicular approach, or through a posterior-lateral or transforaminal approach. After posterior exposure, the intervertebral discs can be removed and replaced with an interbody fusion device inserted through a posterior-lateral approach (PLIF-Posterolateral interbody fusion) or through a lateral transforaminal approach (TLIF/T-PLIF-Transforaminal lateral interbody fusion). Although open laminectomy provides exposure of the disc space, the large size of current interbody devices often makes it technically challenging to avoid injury to the dura and nerve roots during insertion of interbody devices. The large exposure also puts the neural elements and spinal cord at risk from direct mechanical injury during insertion or scarring from overlying soft tissues postoperatively. Scarring is considered a major cause for failed back syndrome in which patients continue to have back and leg pain after spinal surgery. In order to avoid neural injuries with posterior interbody fusion devices some surgeons elect to approach the spine anteriorly, which allows for direct removal of intervertebral discs and vertebras without exposing the neural tissues. Vertebral bodies and intervertebral discs can also be removed anteriorly through a peritoneal or retro-peritoneal approach. Anterior approaches are now more popular and are becoming the standard approach for implanting intervertebral disc replacement or interbody fusion (ALIF-Anterior lumbar interbody fusion) devices but still require major surgery and in cases of interbody fusion they require a second open posterior exposure for supplemental postero-lateral instrumented fusion and harvesting of iliac crest bone graft.

Thus, there is increasing consensus among surgeons that there is a need to develop devices, instruments, and methods to limit the size of the incision, extensive muscle stripping, prolonged retraction of muscles for visualization, avoidance of neural tissue retraction and injury, and denervation and devascularization that are known to contribute to poorer patient outcome after traditional open surgeries to treat pathologies deep within the body. In many cases these complications lead to permanent scarring and pain that can be more severe than the pain from the initial ailment. Limiting these complications in addition to the operative, general anesthesia, and recovery times are among the goals of this invention and that of percutaneous or minimally invasive surgeries.

Current disc replacement and interbody fusion devices are fixed in size and shape and although techniques are now being developed to insert these devices percutaneously, for example U.S. Pat. Nos. 5,792,044 and 5,902,231 attributed to Foley et al., the fixed size and shapes of these interbody devices still require distraction instrumentation and techniques to access the intervertebral disc space which necessitates open surgery for anterior placements and limited open exposures for posterior procedures. Although the focus is shifting away from fusion towards maintaining motion with facet replacements and an interbody device (disc or vertebral body replacements), the majority of these disc replacement devices are designed based on a ball-and-socket articulating principle with variable degrees of motion in different planes from a constrained device limiting some motion to a fully unconstrained device with motion in all planes. However, these devices do not permit percutaneous access primarily because they are fixed in shape and size, need to be inserted as separate articulating components, require distraction instrumentation and techniques to open the disc space, and they need to be anchored to the vertebral endplate.

Accordingly, there is a need for an intervertebral implant device that can be inserted in a collapsed state via minimally invasive surgery (MIS) and then can be expanded in situ distally.

SUMMARY OF THE INVENTION

The present invention relates to an intervertebral implant, and more particularly to an intervertebral implant that expands upwards or downwards or both upwards and downwards.

In general, in one aspect, the invention features an expandable intervertebral implant including a base body, a top endplate and a center component. The base body has a front end, a back end, and first and second side portions connecting the front end and the back end. The top endplate is configured to be placed onto an open top of the base body and to expand upward. The top endplate includes a plate, first and second side protrusions extending vertically downward from first and second sides of the plate, respectively, first and second protrusions having inclined surfaces and extending obliquely downward from a first end of the plate and third and fourth protrusions having a triangular shape with at least one inclined surface and extending downward from a second end of the plate. The center component is configured to be placed within the base body and to interface with the top endplate and to move longitudinally forward or backward within the base body, thereby causing the top endplate to expand upwards or move downward, respectively.

Implementations of this aspect of the invention may include one or more of the following features. The center component includes a threaded through-opening in a front portion thereof, first and second sides, and each of the first and second sides of the center component comprises first and second protrusions having inclined surfaces. The expandable intervertebral implant further includes an actuator rod having an outer threaded surface and being configured to be threaded into the threaded through-opening in the front portion of the center component. Threading the actuator rod into the threaded through-opening in the front portion of the center component moves the center component longitudinally forward into the base body, and causes the inclined surfaces of the first and second protrusions of the top endplate to slide upward onto the inclined surfaces of the first protrusions of the first and second sides of the center component, respectively, and the inclined surfaces of the third and fourth protrusions of the top endplate to slide upward onto the inclined surfaces of the second protrusions of the first and second sides of the center component, respectively, thereby causing the top endplate to expand upward. Threading the actuator rod out of the threaded through-opening in the front portion of the center component moves the center component longitudinally backward out of the base body, and causes the inclined surfaces of the first and second protrusions of the top endplate to slide downward onto the inclined surfaces of the first protrusions of the first and second sides of the center component, respectively, and the inclined surfaces of the third and fourth protrusions of the top endplate to slide downward onto the inclined surfaces of the second protrusions of the first and second sides of the center component, respectively, thereby causing the top endplate to move downward. The first and second side portions of the base body have rectangular-shaped first and second recesses configured to complement and receive the first and second side protrusions of the top endplate. The first and second side portions of the base body further include triangular-shaped third and fourth recesses configured to complement and receive third and fourth side protrusions of the top endplate, respectively. The expandable intervertebral implant further includes removable pins configured to be inserted into openings formed in the first and second side portions of the base body and into openings formed in the center component. The openings formed in the first and second side portions are coaxial with the openings formed in the center component. The actuator has a slotted front end, sized and shaped to receive a key. The base body further includes a base plate and the first and second side portions extend upward from the base plate. An outer surface of the base plate includes teeth, ridges, grooves or protrusions. An outer surface of the top endplate includes teeth, ridges, grooves or protrusions. The expandable intervertebral implant further includes a bottom endplate configured to be placed onto an open bottom of the base body and to expand downward. The bottom endplate includes a plate, first and second side protrusions extending vertically upward from first and second sides of the plate, respectively, first and second protrusions having inclined surfaces and extending obliquely upward from a first end of the plate and third and fourth protrusions having a triangular shape with at least one inclined surface and extending upward from a second end of the plate. The center component is also configured to interface with the bottom endplate and to move longitudinally forward or backward within the base body, thereby causing the bottom endplate to expand downward or move upward, respectively. The center component includes a threaded through-opening in a front portion, first and second sides, and each of the first and second sides of the center component has first and second protrusions including upper and lower parallel inclined surfaces and a third protrusion connecting the first and second protrusions. The expandable intervertebral implant further includes an actuator rod having an outer threaded surface and being configured to be threaded into the threaded through-opening in the front portion of the center component. Threading the actuator rod into the threaded through-opening in the front portion of the center component moves the center component longitudinally forward into the base body, and causes the inclined surfaces of the first and second protrusions of the top endplate to slide upward onto the upper inclined surfaces of the first protrusions of the first and second sides of the center component, respectively, and the inclined surfaces of the third and fourth protrusions of the top endplate to slide upward onto the upper inclined surfaces of the second protrusions of the first and second sides of the center component, respectively, thereby causing the top endplate to expand upward. Threading the actuator rod into the threaded through-opening in the front portion of the center component moves the center component longitudinally forward into the base body, and also causes the inclined surfaces of the first and second protrusions of the bottom endplate to slide downward onto the lower inclined surfaces of the first protrusions of the first and second sides of the center component, respectively, and the inclined surfaces of the third and fourth protrusions of the bottom endplate to slide downward onto the lower inclined surfaces of the second protrusions of the first and second sides of the center component, respectively, thereby causing the bottom endplate to expand downward. The plate of the top endplate includes a longitudinally extending central opening and first and second openings positioned on either side of the longitudinally extending central opening. The base body further includes first and second recesses formed on outer surfaces of the first and second side portions thereof, respectively, and the first and second recesses are configured to receive grasping protrusions of an inserter tool. The back end of the base body includes a through-opening configured to receive bone graft material. The actuator includes a front end with a tri-lobe shaped slot configured to receive a tri-lobe shaped tip of an inserter tool.

The details of one or more embodiments of the invention are set forth in the accompanying drawings and description below. Other features, objects, and advantages of the invention will be apparent from the following description of the preferred embodiments, the drawings, and the claims

BRIEF DESCRIPTION OF THE DRAWINGS

Referring to the figures, wherein like numerals represent like parts throughout the several views:

FIG. 32A is a perspective view of the tip of the cylindrical shaft of the inserter tool of FIG. 31A;

FIG. 32B is a perspective view of the front of the cylindrical sleeve of the inserter tool of FIG. 31A;

FIG. 32C is a perspective view of the front of the intervertebral implant 400 of FIG. 31A;

DETAILED DESCRIPTION OF THE INVENTION

The present invention relates to an intervertebral implant that is inserted in a collapsed configuration between two neighboring vertebras and then is distally expanded upwards or downwards or both upwards and downwards.

Figure 1A:
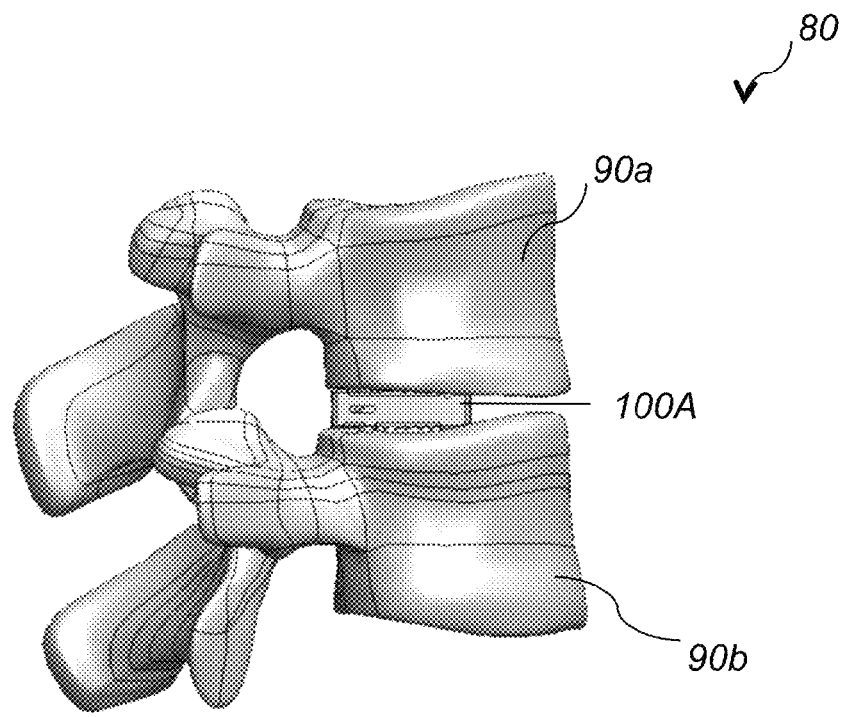
FIG. 1A is a schematic side view of an intervertebral implant that is inserted between two neighboring vertebras and expands upwards and downwards, according to this invention.
Figure 1B:
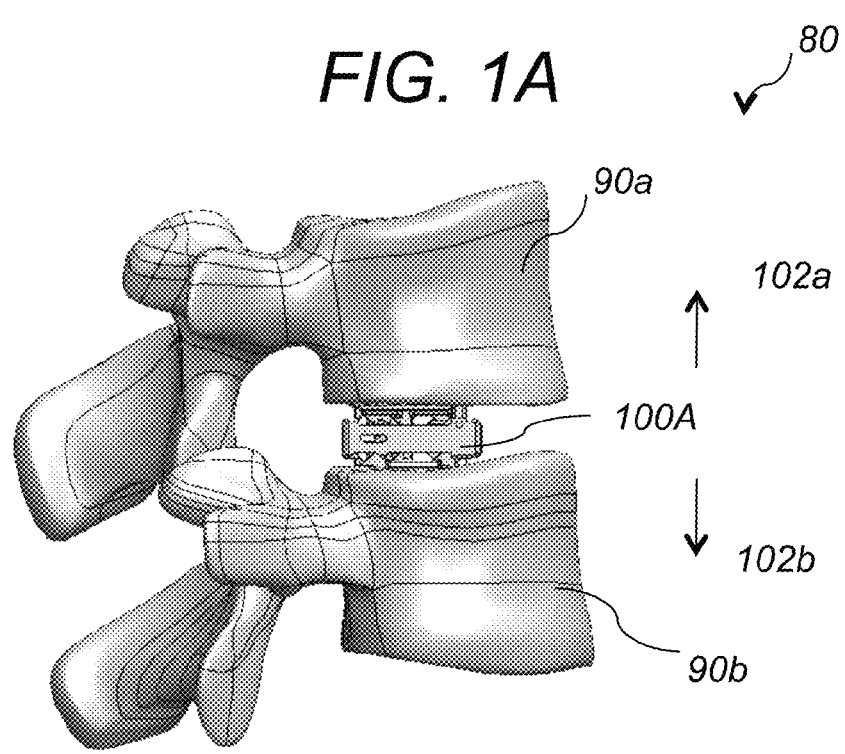
FIG. 1B is a schematic side view of the intervertebral implant of FIG. 1A in the "expanded" configuration.
Figure 10:
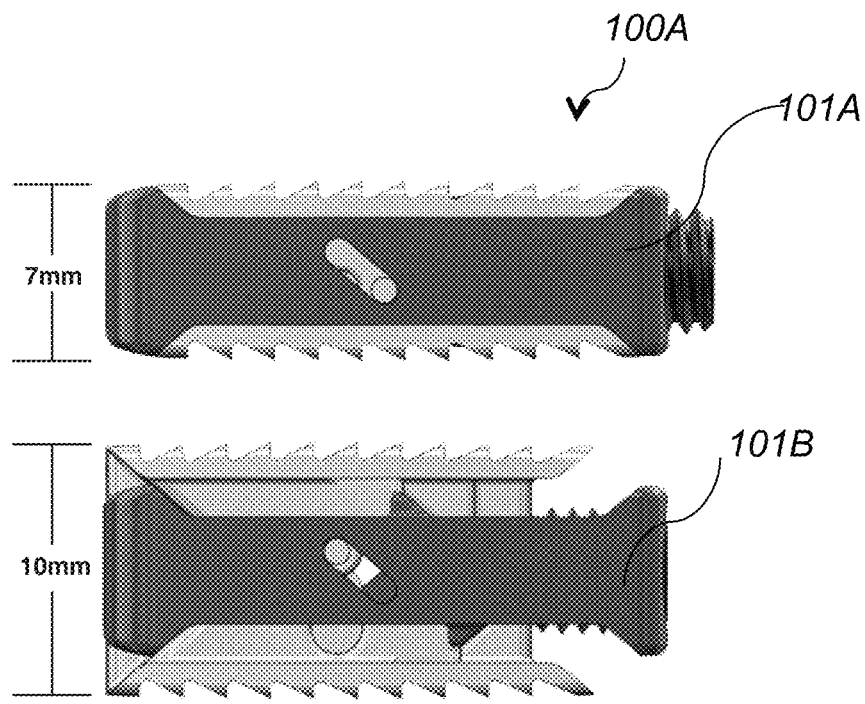
FIG. 10 depicts left side views of the intervertebral implant of FIG. 2A in the collapsed and in the expanded configurations.

Referring to FIG. 1A, intervertebral implant 100A is inserted between neighboring vertebras 90a and 90b. Once inserted in the intervertebral disk space, intervertebral implant 100A expands upwards and downwards along directions 102a and 102b, respectively, as shown in FIG. 1B. Intervertebral implant 100A is used in posterior, anterior, lateral, trans-foraminal to extra-foraminal implantation procedures. Intervertebral implant 100A has a small sized cage and a compact-sized expansion mechanism. The expansion mechanism allows the cage to be expanded in height after the implant is inserted into the intervertebral space. The height of the cage may be expanded in the range of 6 mm-16 mm. In one example, intervertebral implant 100A has a height of 7 mm and expands to a height of 10 mm, as shown in FIG. 10.

Figure 2A:
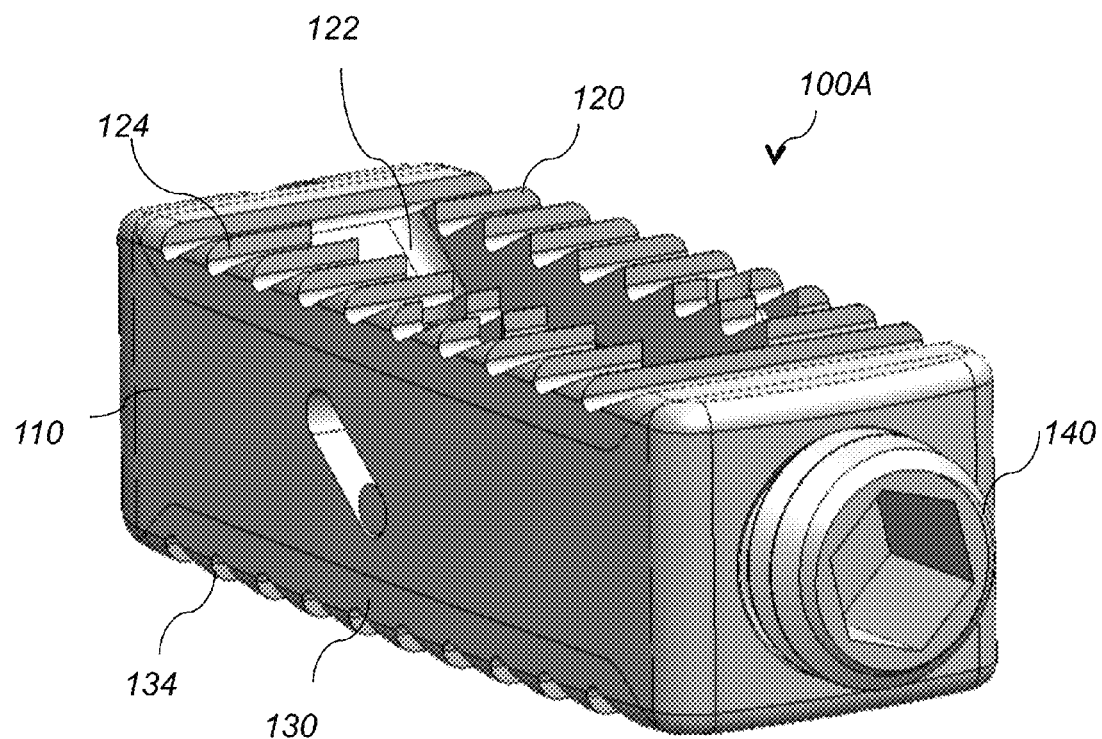
FIG. 2A is a perspective view of an intervertebral implant in the "collapsed" configuration.
Figure 2B:
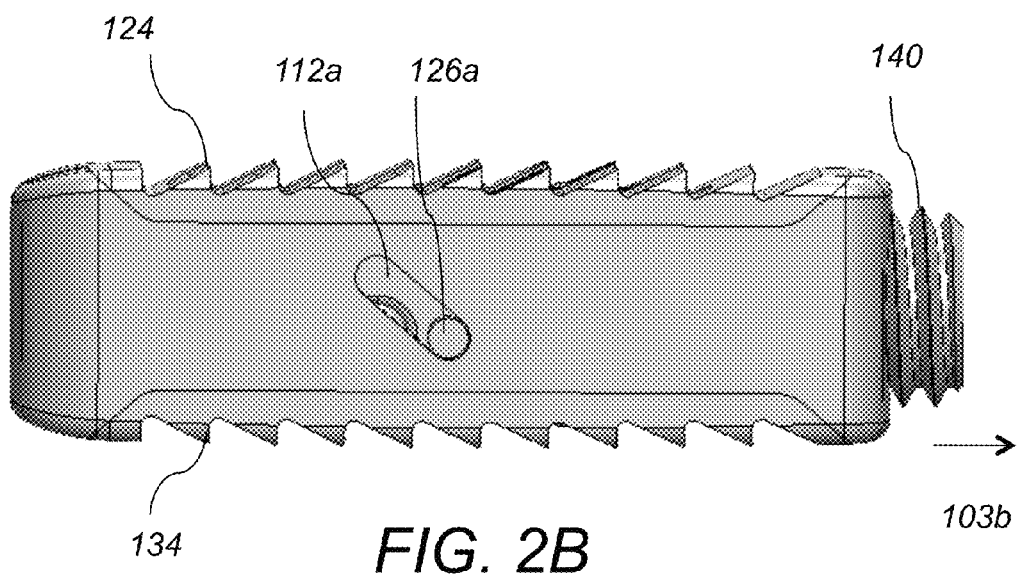
FIG. 2B is a side view of the intervertebral implant of FIG. 2A.
Figure 3A:
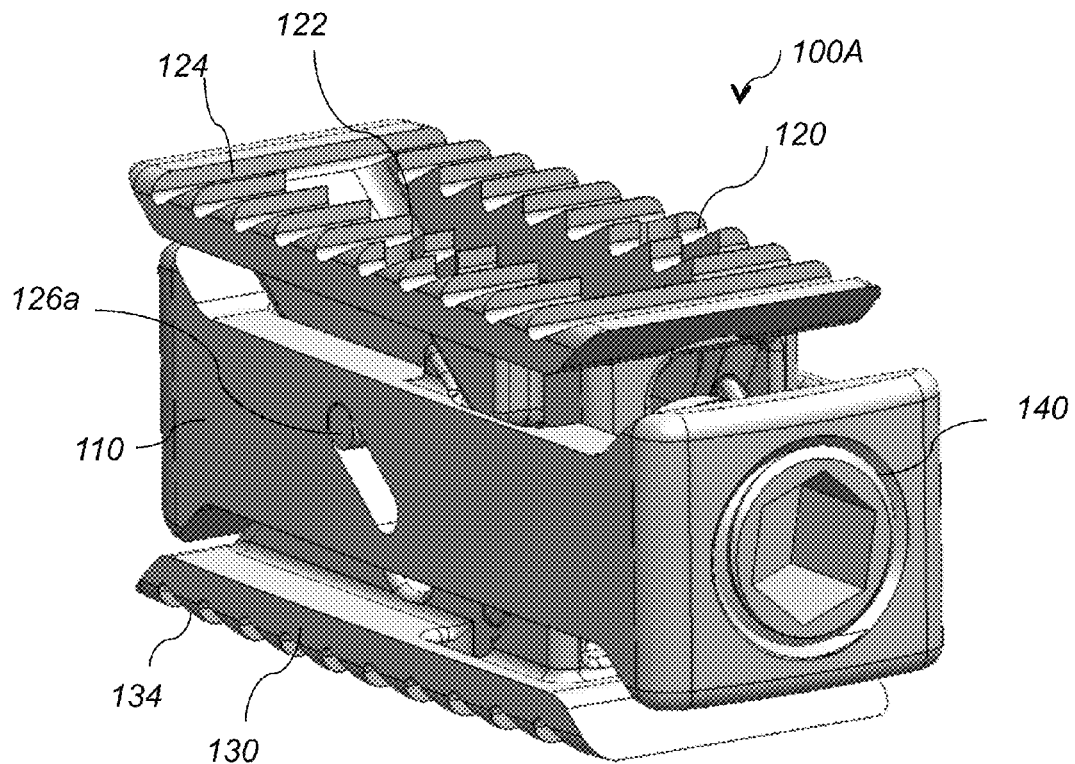
FIG. 3A is a perspective view of an intervertebral implant in the "expanded" configuration.
Figure 3B:
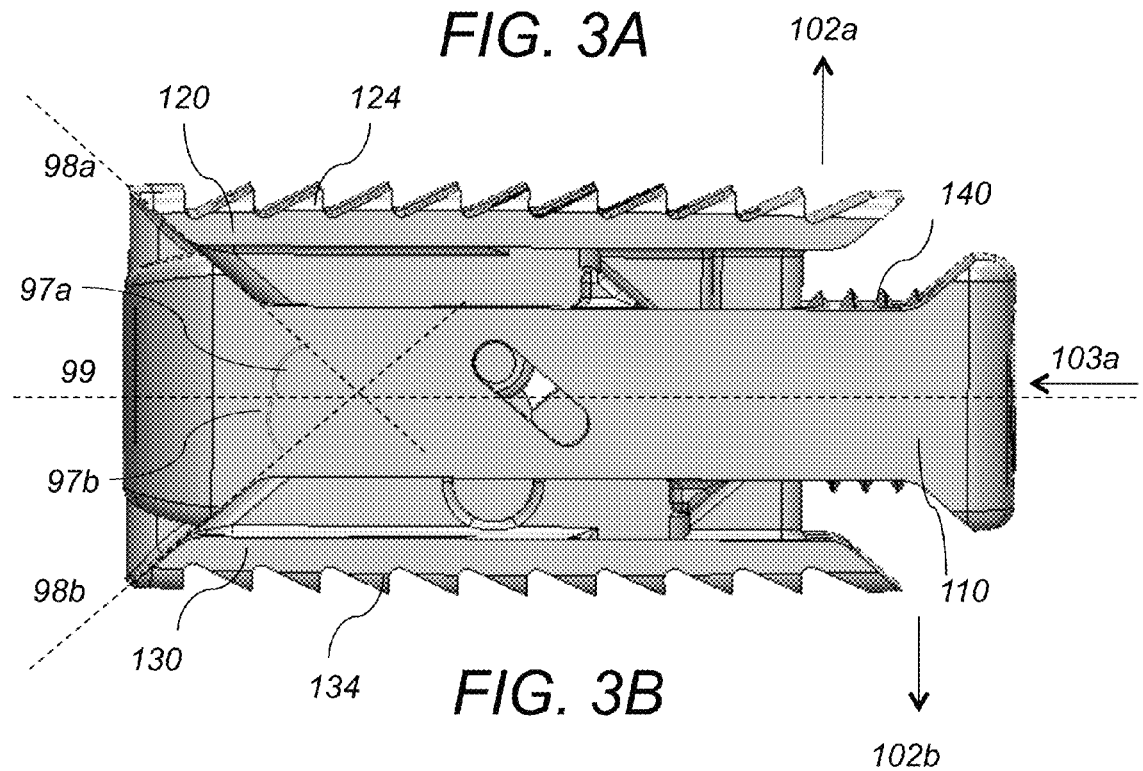
FIG. 3B is a side view of the intervertebral implant of FIG. 3A.
Figure 4:
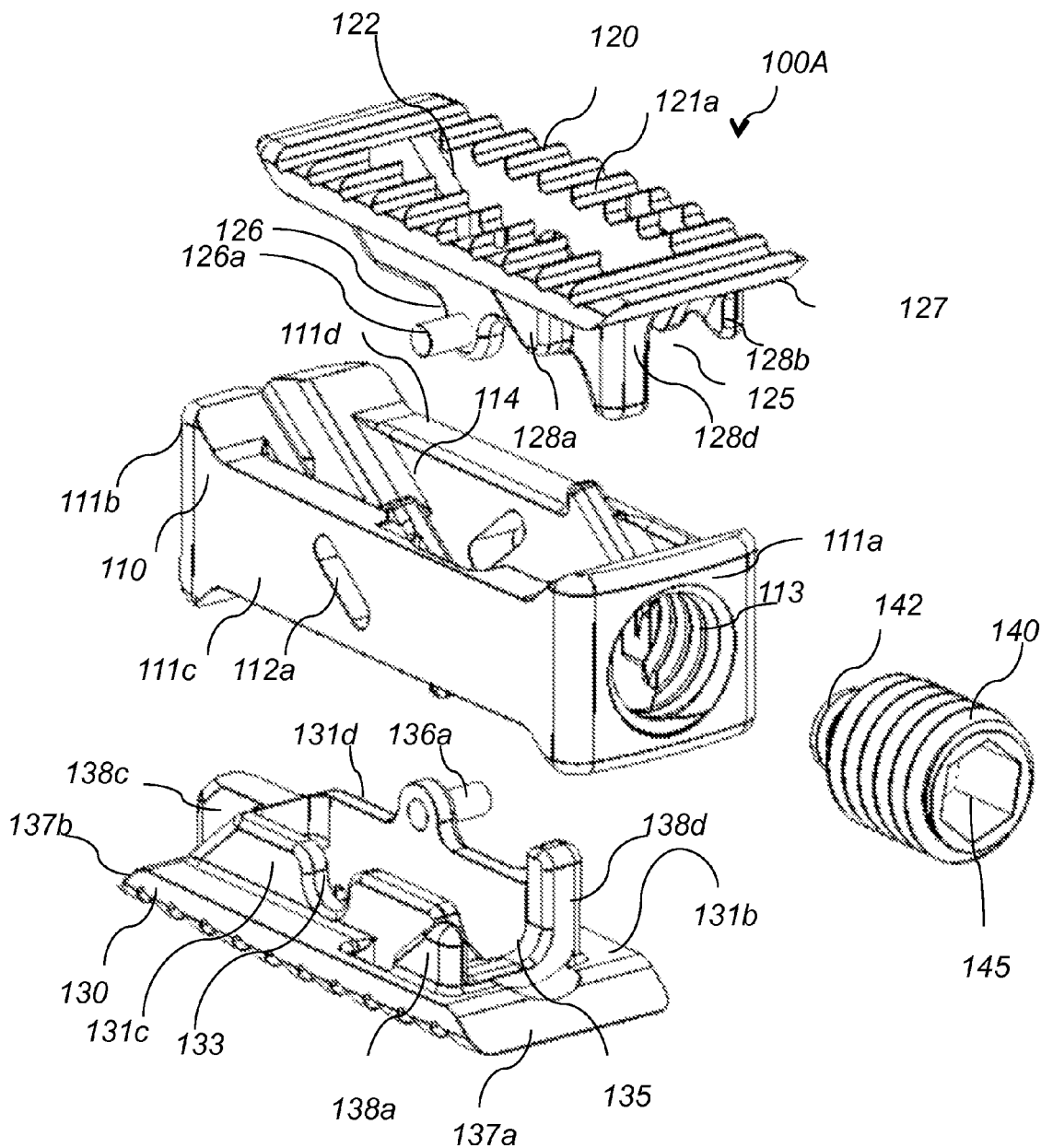
FIG. 4 is an exploded view of the intervertebral implant of FIG. 2A.
Figure 5A:
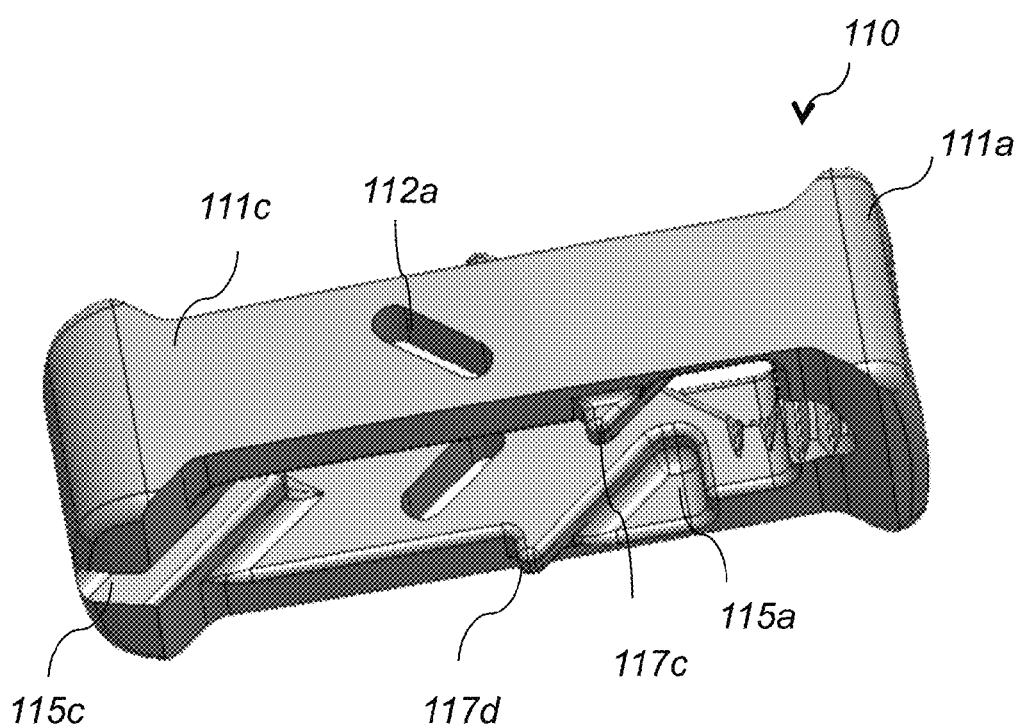
FIG. 5A is a bottom perspective view of the center body of the intervertebral implant of FIG. 2A.
Figure 5B:
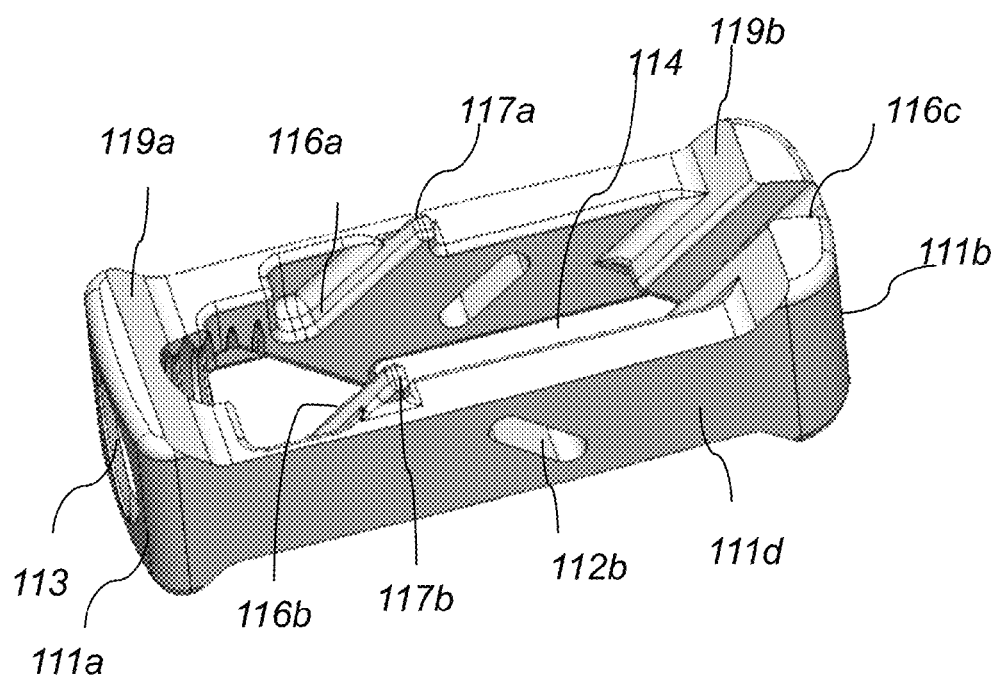
FIG. 5B is a top perspective view of the center body of the intervertebral implant of FIG. 2A.

Referring to FIG. 2A and FIG. 2B, intervertebral implant 100A includes a center body 110, a top endplate 120, a bottom endplate 130, and a threaded actuator 140. Threaded actuator 140 is turned clockwise distally with a driver (not shown) to expand the intervertebral implant 100A by moving the top and bottom plates upwards 102a and downwards 102b, respectively, as shown in FIG. 3B. Threaded actuator 140 may also be turned counter-clockwise distally with the driver to collapse the intervertebral implant 100A by moving the top and bottom plates downwards upwards 102b and upwards 102a, respectively. Top and bottom endplates 120, 130 slide along inclines 98a, 98b, respectively, oriented at angles 97a, 97b of 40 degrees relative to the center body axis 90.

Figure 8A:
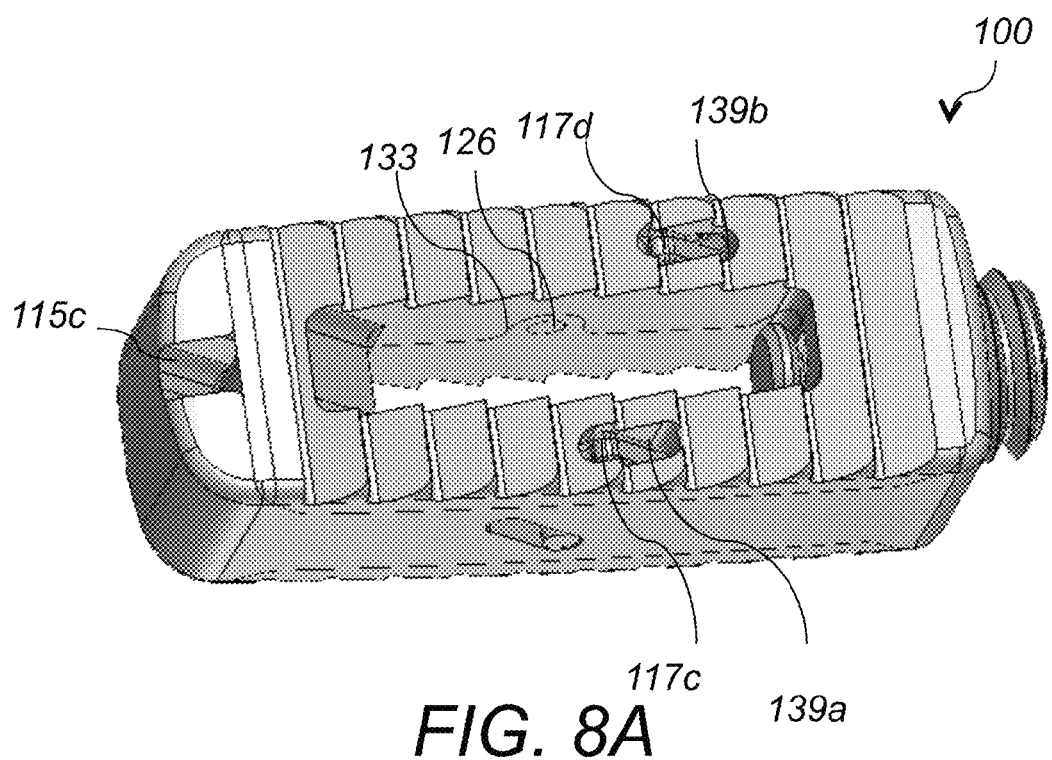
FIG. 8A is a bottom perspective view of the intervertebral implant of FIG. 2A.
Figure 8B:
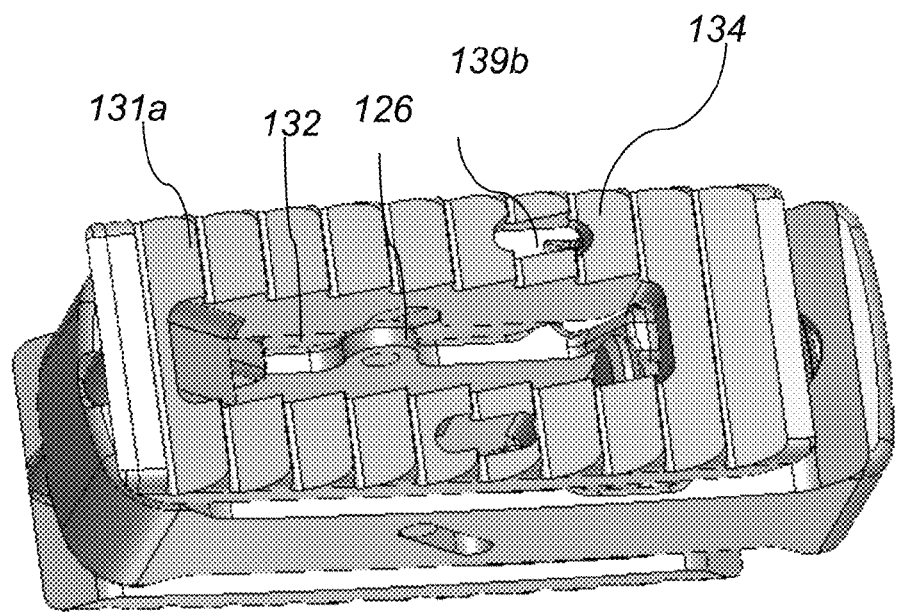
FIG. 8B is a bottom perspective view of the intervertebral implant of FIG. 2A in the expanded configuration.
Figure 9A:
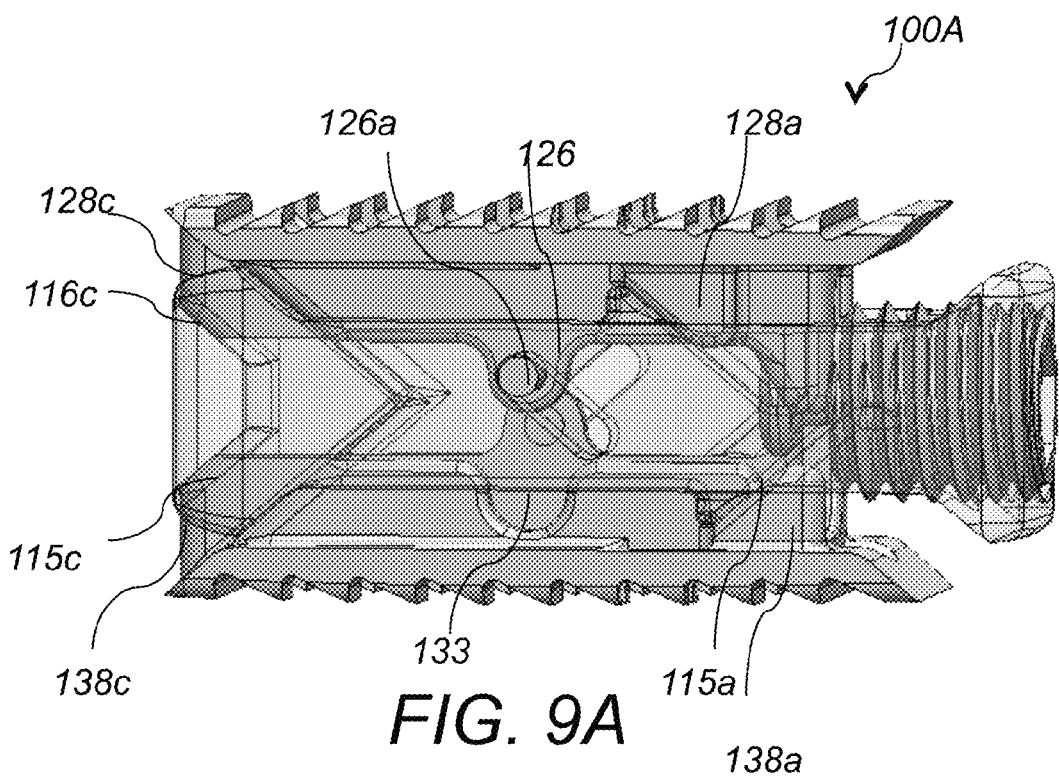
FIG. 9A is left side view of the intervertebral implant of FIG. 3A in the expanded configuration.
Figure 9B:
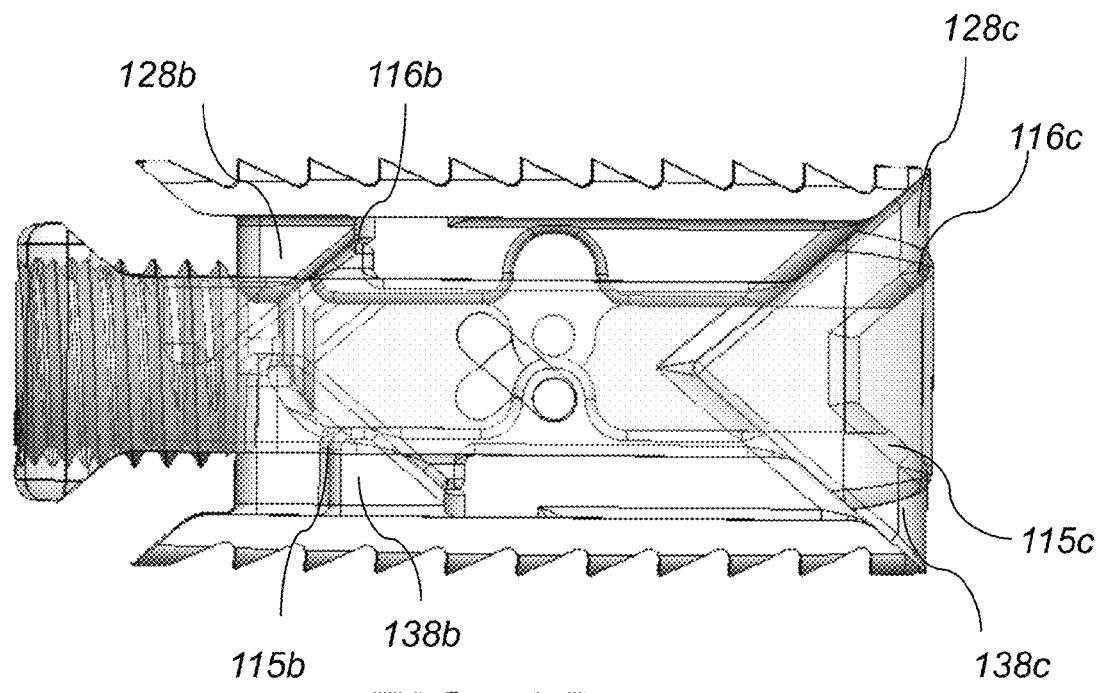
FIG. 9B is a right side view of the intervertebral implant of FIG. 3A in the expanded configuration.

Referring to FIG. 2A-FIG. 5B, in one example, center body 110 includes a front side 111b, a back side 111a, a left side 111c and a right side 111d. Left and right sides 111c, 111d connect the front and back sides 111b, 111a. Back side 111a includes a threaded through-opening 113 shaped and sized to engage the threaded actuator 140. The inner surface of the front side 111b includes inclined recessed paths 116c and 115c, as shown also in FIG. 9A and FIG. 9B. In FIG. 9A and FIG. 9B, center body 110 is depicted as transparent to help visualize the mechanical interconnections of the center body with the top and bottom endplates. The inner surface of the left side 111c also includes inclined recessed paths 116a and 115a. The inner surface of the right side 111d also includes inclined recessed paths 116b and 115b. As was mentioned above, in one example, inclined recessed paths 116a-116c, 115a-115c are oriented at an angle of 40 degrees relative to the center body axis 90. Inclined recessed paths 116a-116c, and 115a-115c are shaped and sized to receive and slidably engage protrusions 128a, 128b, 128c, and 138a, 138b, 138c of the top and bottom endplates 120, 130, respectively, as will be described below. Left side 111c and right side 111d also include slots 112a, 112b, respectively. Slots 112a, 112b are also oriented at an angle of 40 degrees relative to the center body axis 90 and are shaped and sized to receive and slidably engage protrusions 126a, 126b of the top and bottom endplates 120, 130, respectively, as will be described below. Center body 110 also includes left side and right side top protrusions 117a, 117b and left side and right side bottom protrusions 117c, 117d. Top protrusions 117a, 117b are shaped and sized to engage left and right openings 129a, 129b of the top endplate, respectively, when the implant 100A is in the collapsed configuration. Bottom protrusions 117a, 117b are shaped and sized to engage left and right openings 139a, 139b of the bottom endplate, respectively, when the implant 100A is in the collapsed configuration, as shown in FIG. 8A. Center body 110 has back and front chamfered surfaces 119a, 119b that complement chamfered surfaces 127b, 127a of the top endplate 120 and chamfered surfaces 137b, 137a of the bottom endplate 130. Center body 110 also forms a central opening 114 extending from the top side to the bottom side. Central opening 114 is shaped and sized for housing the expansion mechanism of the intervertebral implant 100A, in the collapsed configuration of FIG. 2A.

Referring to FIG. 2A-FIG. 8B, in one example, top endplate 120 includes a top surface 121a, a bottom surface 121b, left side 121c, right side 121d and a central through opening 122 extending from the top surface to the bottom surface. Top surface 121a includes teeth 124 and two openings 129a, 129b positioned left and right of the central opening 124. As was mentioned above, openings 129a, 129b engage top protrusions 117a, 117b of the center body 110, when the implant 110A is in the collapsed configuration. Top endplate also includes left and right side protrusions 128a, 128b and a front side protrusion 128c. As was mentioned above, protrusions 128a, 128b and 128c are shaped and sized to slide within inclined recessed paths 116a, 116b, and 116c of the center body, respectively, when the actuator 140 moves along direction 103a and pushes the top plate upwards along 102a. Left side 121c also includes a semi-circular protrusion 126 that fits in a complementary semi-circular recess 133 formed on the left side of the bottom endplate 130, when the implant 100A is in the collapsed configuration, as shown in FIG. 8A. Left side also includes a cylindrical protrusion 126a, extending sidewise from the semi-circular protrusion 126. Cylindrical protrusion 126a is shaped and sized to engage and slide within slot 112a of the center body 110, when the implant expands. The right side 121d of the top endplate 120 includes a semicircular recess 123 that is shaped and sized to receive a semi-circular protrusion 136 of the bottom endplate 130. Top endplate 120 also includes a downward extending protrusion 128d that is dimensioned to engage the recessed space 143 of the actuator 140, shown in FIG. 11. Top endplate 120 also has front and back chamfered surfaces 127b, 127a that complement chamfered front and back surfaces 119b, 119a of the center body 110, respectively.

Bottom endplate 130 is shaped similarly to the top endplate 120. Referring to FIG. 2A-FIG. 8B, in one example, bottom endplate 130 includes a bottom surface 131a, a top surface 131b, left side 121c, right side 131d and a central through opening 132 extending from the bottom surface to the top surface. Bottom surface 131a includes teeth 134 and two openings 139a, 139b positioned left and right of the central opening 134. As was mentioned above, openings 139a, 139b engage bottom protrusions 117c, 117d of the center body 110, when the implant 110A is in the collapsed configuration. Bottom endplate also includes left and right side protrusions 138a, 138b and a front side protrusion 138c. As was mentioned above, protrusions 138a, 138b and 138c are shaped and sized to slide within inclined recessed paths 115a, 115b, and 115c of the center body, respectively, when the actuator 140 moves along direction 103a and pushes the bottom plate downwards along 102b. Right side 131d also includes a semi-circular protrusion 136 that fits in the complementary semicircular recess 123 formed on the right side of the top endplate 120, when the implant 100A is in the collapsed configuration, as shown in FIG. 7A. Right side also includes a cylindrical protrusion 136a, extending sidewise from the semi-circular protrusion 136. Cylindrical protrusion 136a is shaped and sized to engage and slide within slot 112b of the center body 110, when the implant expands. The left side 131c of the bottom endplate 130 includes a semicircular recess 133 that is shaped and sized to receive the semi-circular protrusion 126 of the top endplate 120, as shown in FIG. 8A. Bottom endplate 130 also includes an upward extending protrusion 138d that is dimensioned to engage the recessed space 143 of the actuator 140, shown in FIG. 11. Through-openings 122, 132 of the top and bottom endplates, respectively are used for receiving fusion promoting bone graft material. Bottom endplate 130 also has front and back chamfered surfaces 137b, 137a that complement chamfered front and back surfaces 119b, 119a of the center body 110, respectively.

Figure 11:
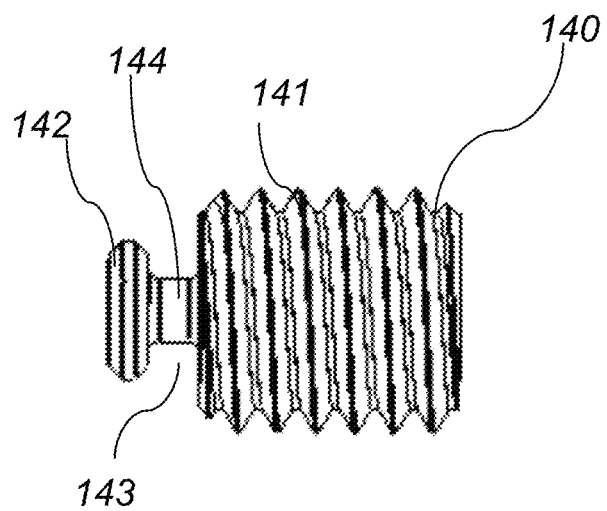
FIG. 11 is a side view of the threaded actuator of the intervertebral implant of FIG. 2A.
Figure 12A:
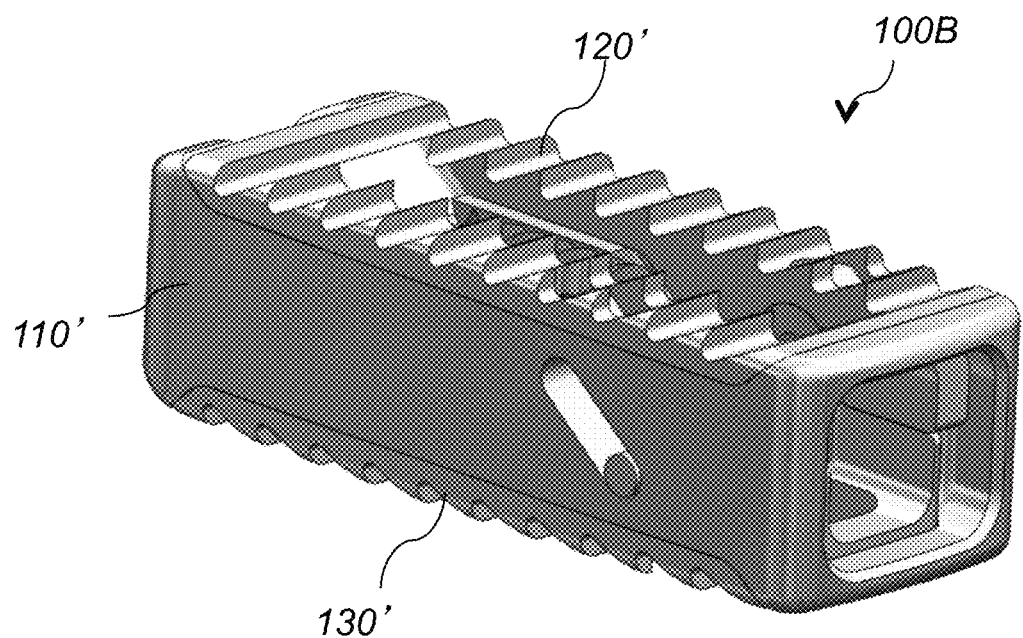
FIG. 12A is a perspective view of another example of an intervertebral implant in the "collapsed" configuration.
Figure 12B:
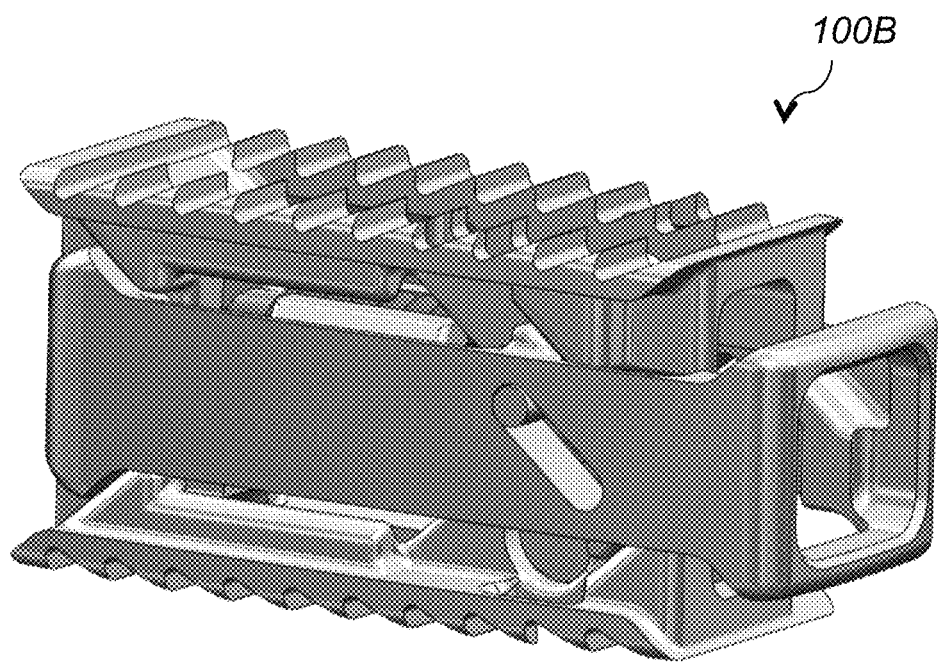
FIG. 12B is a perspective view of the intervertebral implant of FIG. 12A in the "expanded" configuration.
Figure 12C:
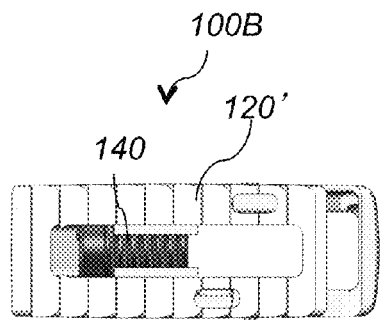
FIG. 12C is a top view of the intervertebral implant of FIG. 12A.
Figure 12E:
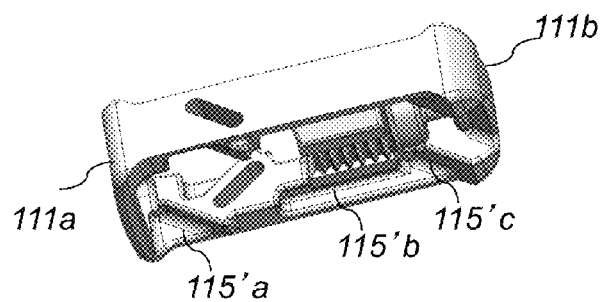
FIG. 12E is a bottom perspective view of the center body of the intervertebral implant of FIG. 12A.
Figure 12D:
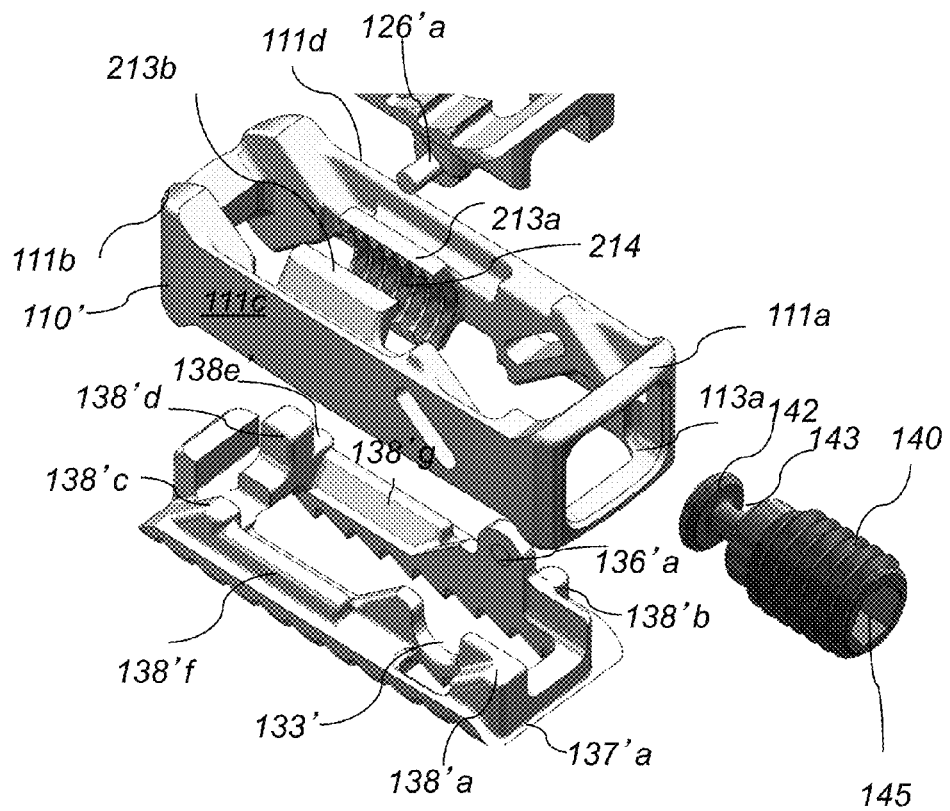
FIG. 12D is an exploded view of the intervertebral implant of FIG. 12A.

Referring to FIG. 11, actuator screw 140 includes a threaded main portion 141, a front portion 142 and a rod 144 connecting the main portion 141 to the front portion 142. Main portion 141 has a larger diameter than the front portion 142. A recessed space 143 is formed around rod 144 between the back of the main portion 140 and the front of the front portion 142. Actuator 140 engages the top endplate 120 and the bottom endplate 130 by receiving protrusions 128d and 138d within recessed space 143. The back side of the actuator 140 also includes a hexagonal opening 145 that is sized and shaped to receive the distal portion of a driver tool.

In operation, the expandable intervertebral implant 100A is inserted in the collapsed configuration of FIG. 2A with an inserter in the intervertebral disk space between vertebras 90a, 90b. Next, a driver tool is inserted in opening 145 of the actuator 140 and is used to rotate clockwise the actuator screw 140. Rotating the actuator screw 140 clockwise moves the actuator along direction 103a and this motion of the actuator 140 causes the protrusions of the top and bottom endplates to slide up and down within their corresponding inclined recesses of the center body 110, respectively, and moves the top endplate 120 upwards along 102a and the bottom endplate 130 downwards along 102b, thereby expanding the height of the intervertebral implant 100A, as shown in the expanded configuration of FIG. 3A. Rotating the actuator screw 140 counter-clockwise moves the actuator 140 along direction 103b and this motion of the actuator 140 causes the protrusions of the top and bottom endplates to slide down and up within their corresponding inclined recesses of the center body 110, respectively, and moves the top endplate 120 downwards along 102b and the bottom endplate 130 upwards along 102a, thereby collapsing the height of the intervertebral implant 100A, as shown in the collapsed configuration of FIG. 2A.

The components of the intervertebral implant 100A may be made of bone, polyetheretherketone (PEEK), Nitinol, metals, titanium, steel, metal composites, biodegradable materials, collagen matrices, synthetic polymers, polysaccharides, calcium minerals, calcium salts, or composites containing calcium or phosphorous naturally or man made.

Referring to FIG. 12A-12D, in other examples, center body 110' includes a front side 111b, a back side 111a, a left side 111c and a right side 111d. Left and right sides 111c, 111d connect the front and back sides 111b, 111a. Back side 111a includes a non-threaded through-opening 113a shaped and sized to allow the threaded actuator 140 to pass through. Center body 110 also includes spaced apart semi-cylindrical components 213a, 213b extending from about the centers of the inner side surfaces 111d and 111c, respectively, and being oriented opposite to each other. The inner surfaces of components 213a, 213b include threads 214. Components 213a, 213b and threads 214 are shaped and sized to engage the threaded actuator 140 after it passes through opening 113. In this example, bottom endplate 130' includes left side protrusions 138'a, 138'f and 138'c that are shaped and sized to slide within inclined recessed paths 115'a, 115'b, and 115'c of the center body 110', respectively, when the actuator 140 moves along direction 103a and pushes the bottom plate downwards along 102b. The right side of the bottom endplate 130' also includes similar protrusions 138'b, 138', 138'e that are also shaped and sized to slide within corresponding inclined recessed paths on the right side of the center body 110'. Bottom endplate 130' also includes an upward extending protrusion 138d that is located closer to the back side of the bottom endplate 130' and is dimensioned to engage the recessed space 143 of the actuator 140, shown in FIG. 12D. Top endplate 120' is shaped similarly to the bottom endplate 130'. In this example, fusion promoting bone graft material is inserted from the back side of the intervertebral implant 100B through the front opening 113a after the implant has been inserted and expanded.

Figure 6A:
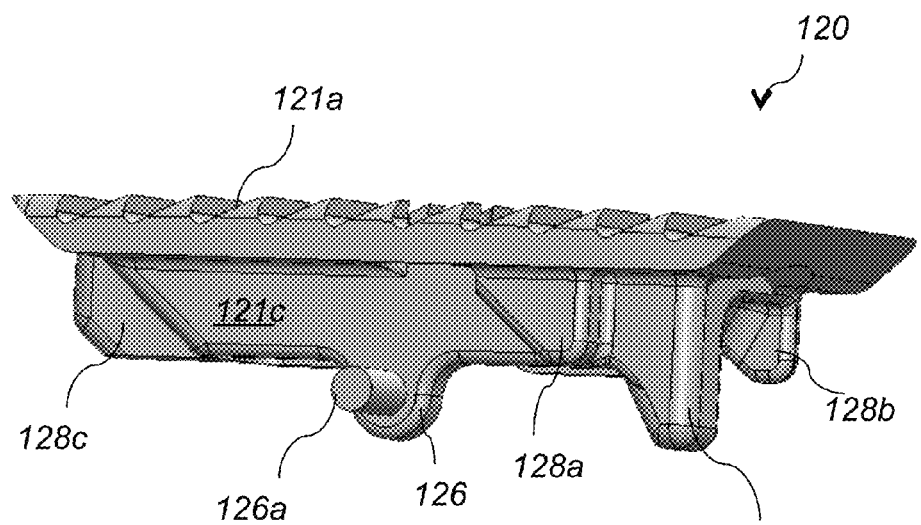
FIG. 6A is a left side perspective view of the top endplate of the intervertebral implant of FIG. 2A.
Figure 6B:
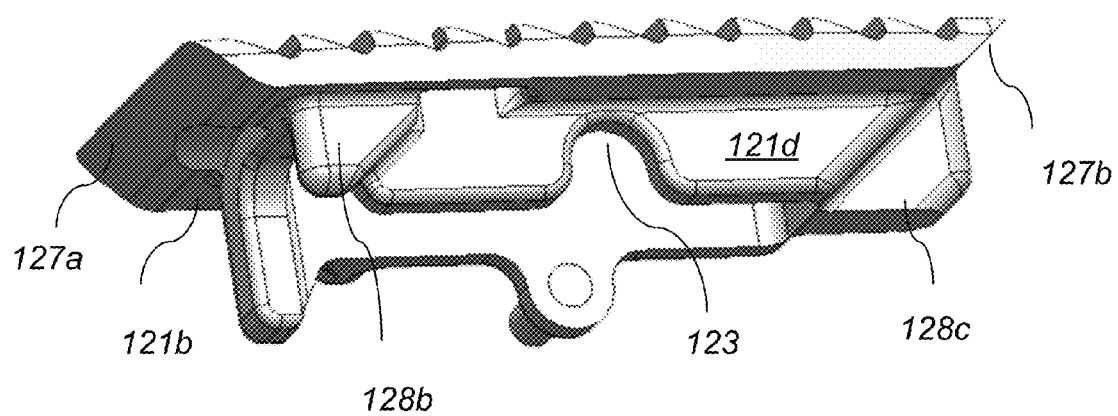
FIG. 6B is a right side perspective view of the top endplate of the intervertebral implant of FIG. 2A.
Figure 7A:
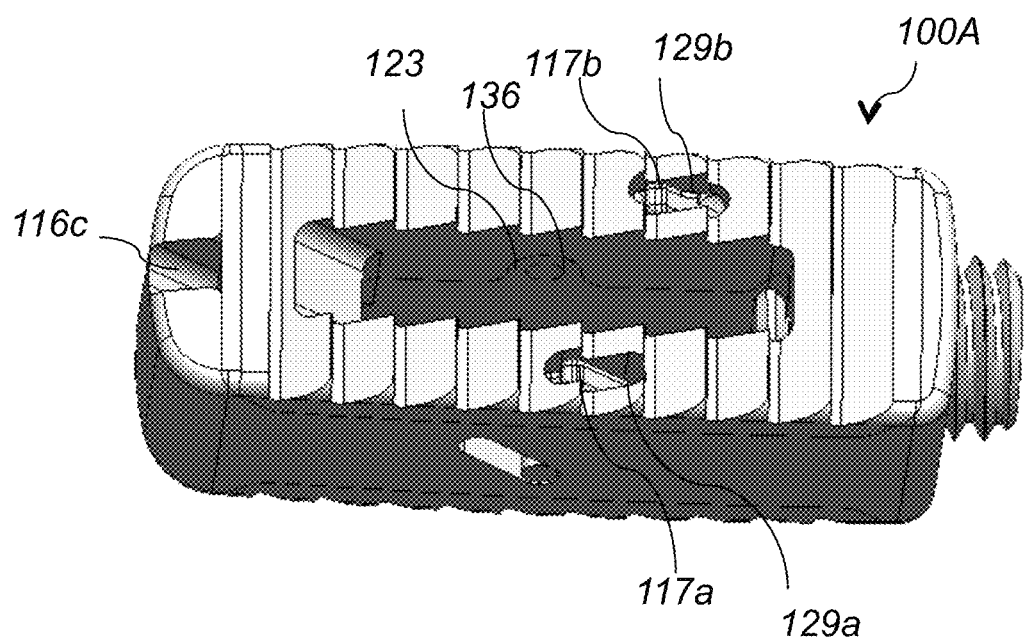
FIG. 7A is a top perspective view of the intervertebral implant of FIG. 2A.
Figure 7B:
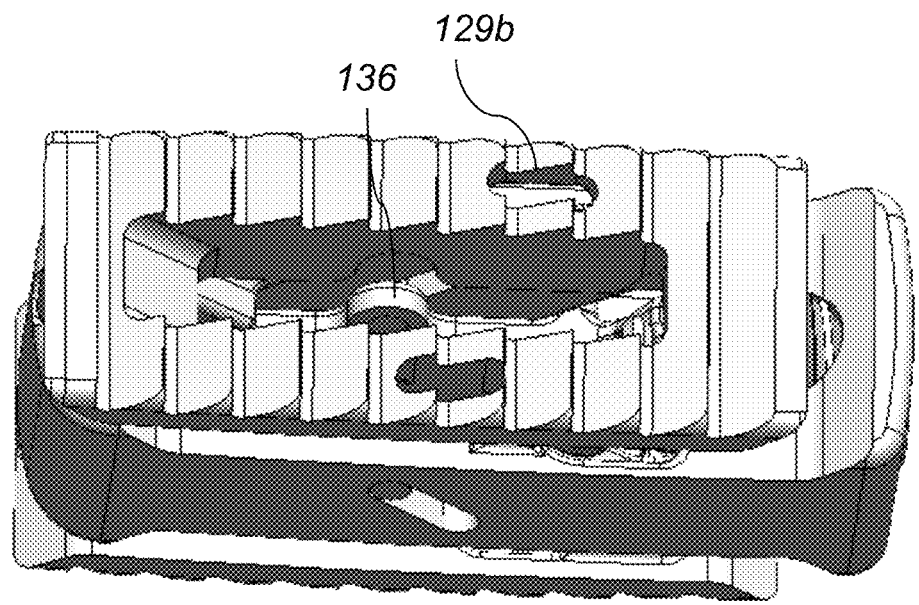
FIG. 7B is a top perspective view of the intervertebral implant of FIG. 2A in the expanded configuration.
Figure 13A:
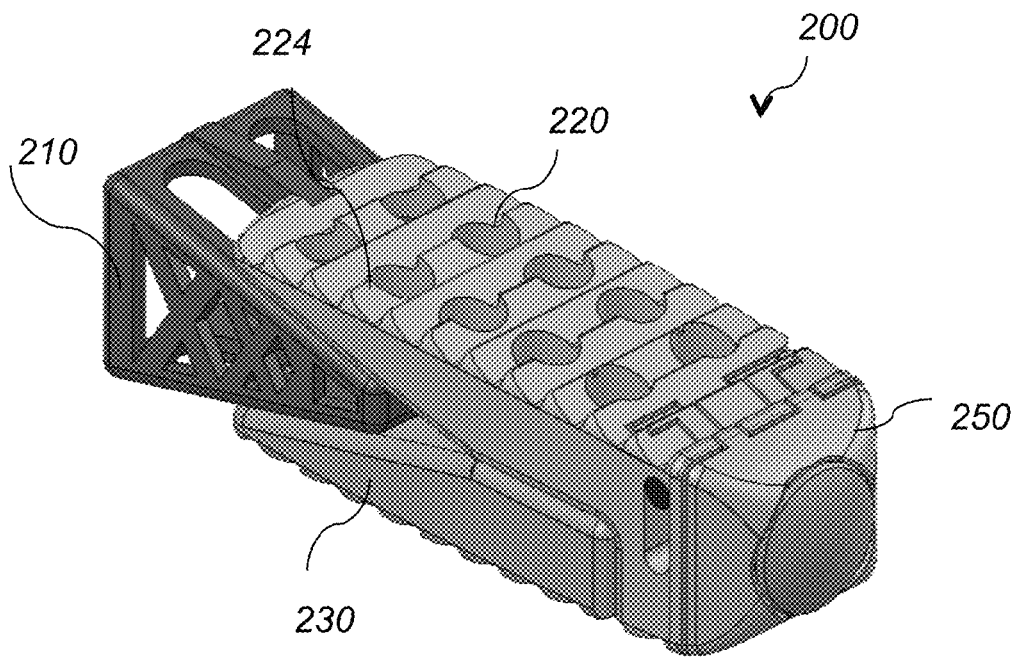
FIG. 13A is a perspective view of another embodiment of an intervertebral implant in the "collapsed" configuration.
Figure 13B:
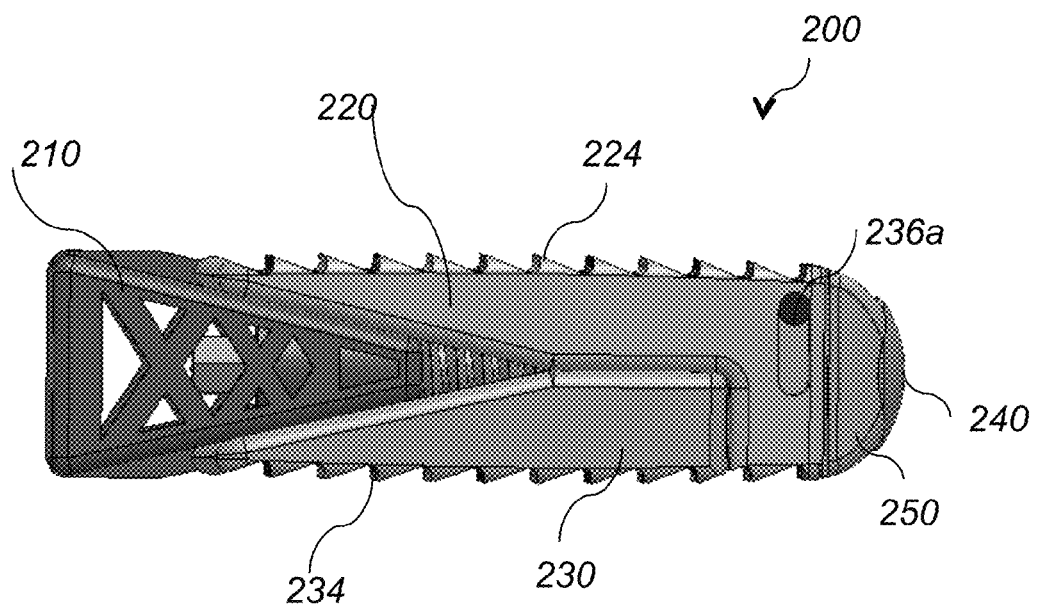
FIG. 13B is a side view of the intervertebral implant of FIG. 13A.
Figure 14A:
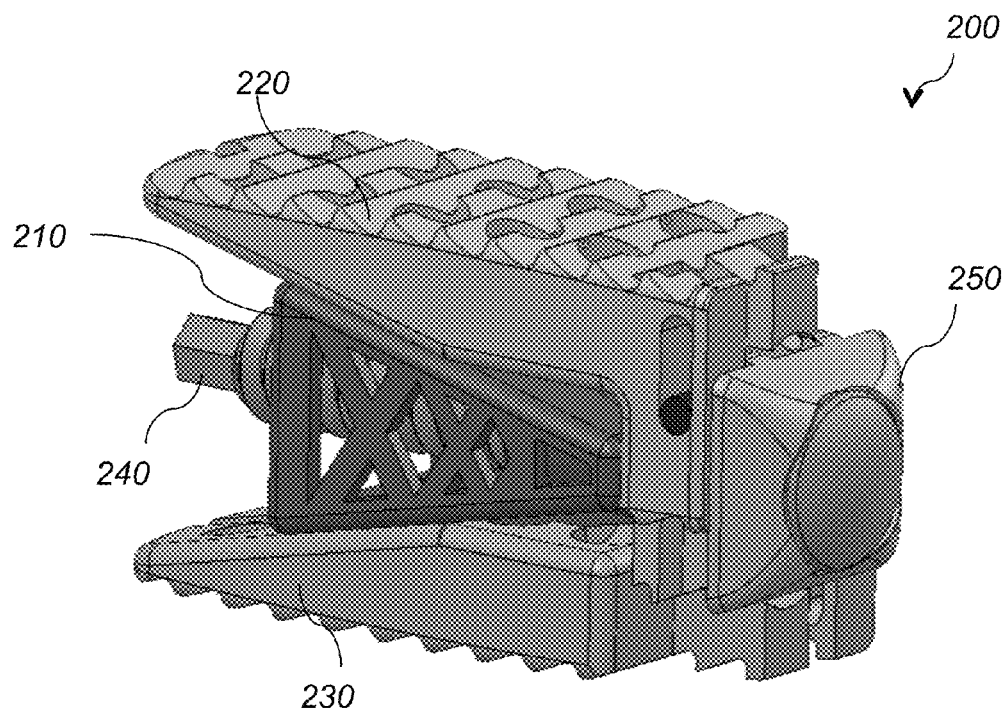
FIG. 14A is a perspective view of the intervertebral implant of FIG. 13A in the "expanded" configuration.
Figure 14B:
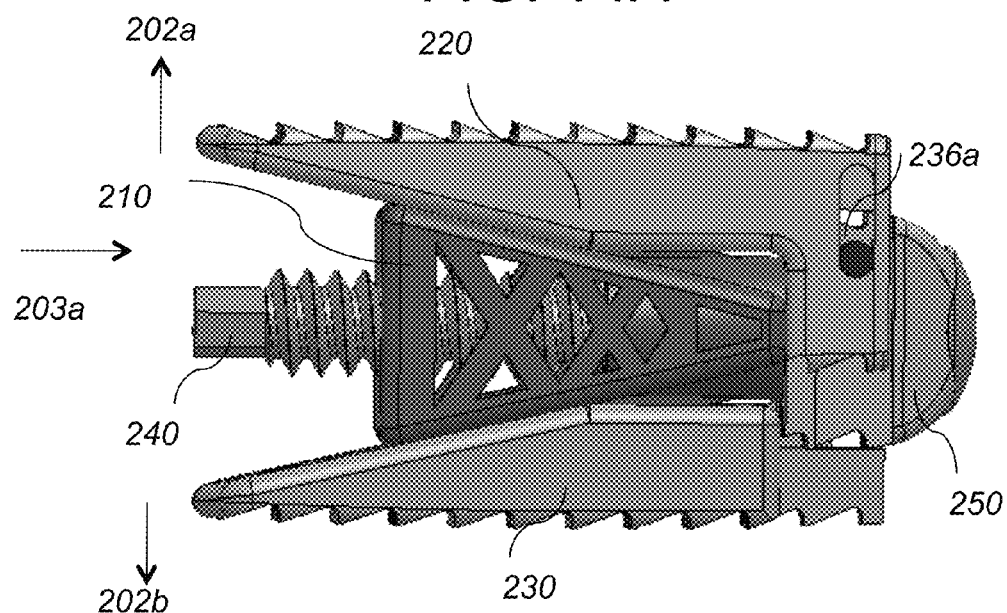
FIG. 14B is a side view of the intervertebral implant of FIG. 14A.

Referring to FIG. 13A-FIG. 6 in another embodiment, an intervertebral implant 200 that expands equally upwards and downwards along directions 202a, 202b includes a top endplate 220, a bottom endplate 230, a wedged basket 210, a front component 250, and a threaded actuator 240. Threaded actuator 240 is turned clockwise distally with a driver (not shown) to move the wedged basket 210 forward. The forward motion of the wedged basket 210 moves the top and bottom endplates upwards 202a and downwards 202b, respectively, and thereby expands the intervertebral implant 200, as shown in FIG. 14B. Threaded actuator 240 may also be turned counter-clockwise distally with the driver to move the wedged basket 210 backward. Moving the wedged basket backwards causes the top and bottom plates to move down along 102b and up along 102a, respectively, and thereby to collapse the intervertebral implant 200.

Figure 15A:
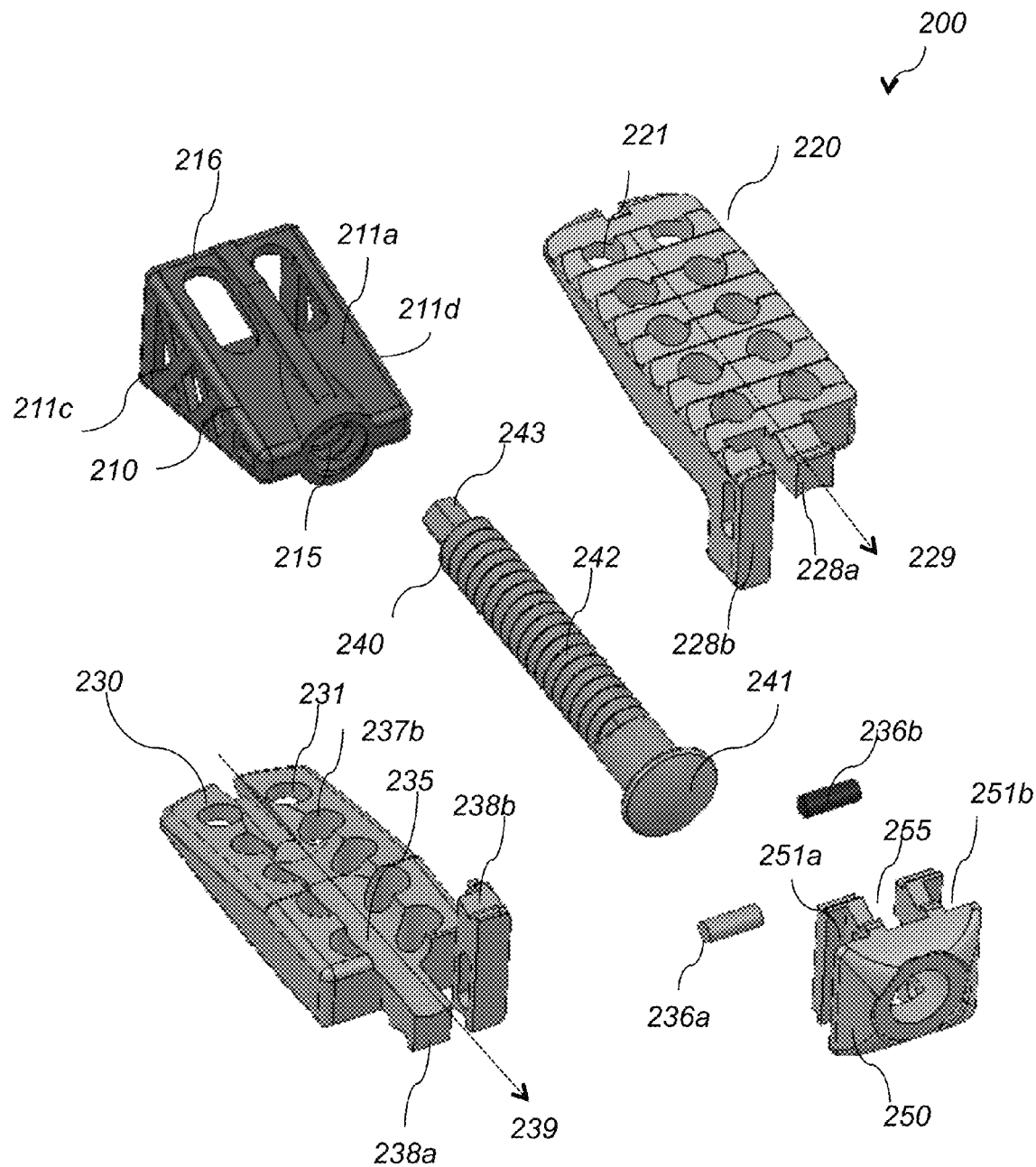
FIG. 15A is an exploded view of the intervertebral implant of FIG. 14A.
Figure 15B:
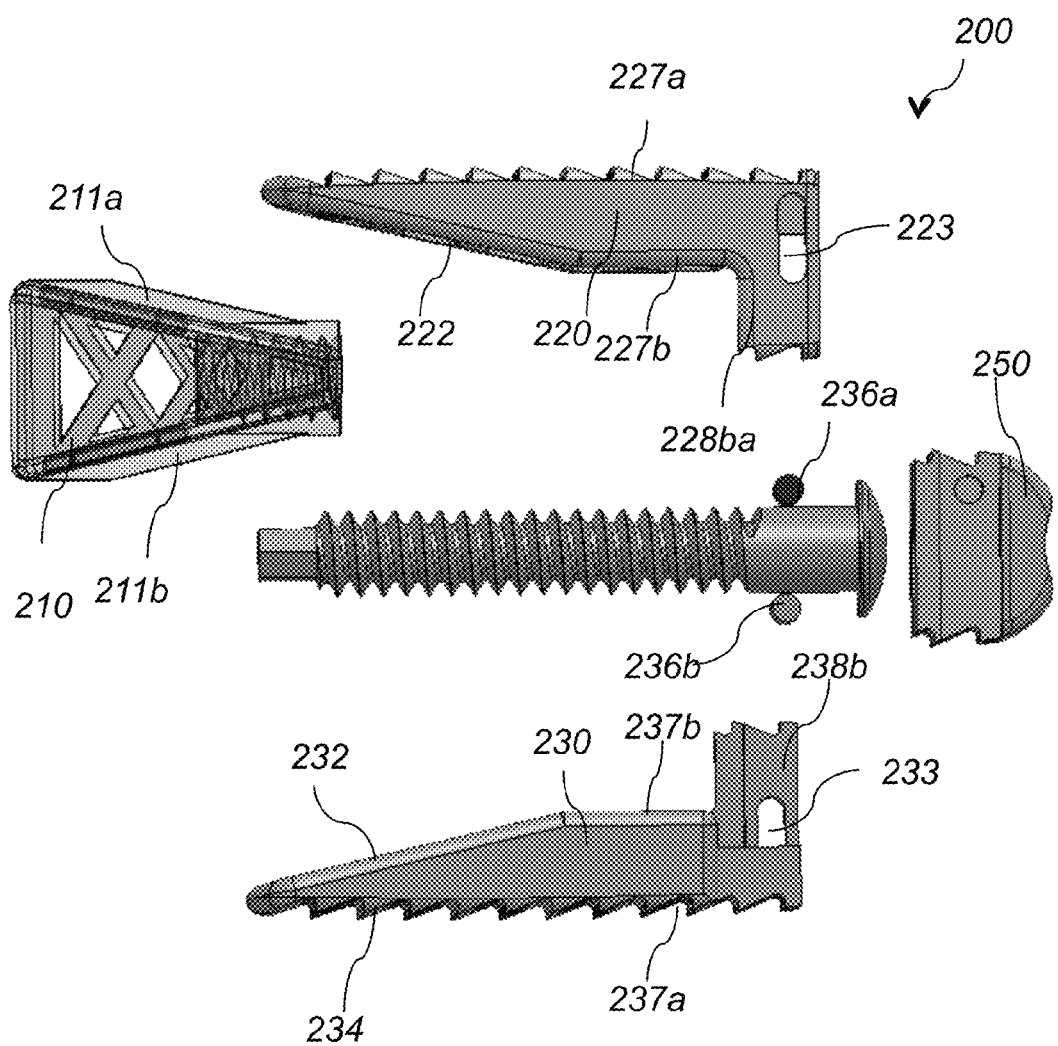
FIG. 15B is another exploded view of the intervertebral implant of FIG. 14A.
Figure 16:
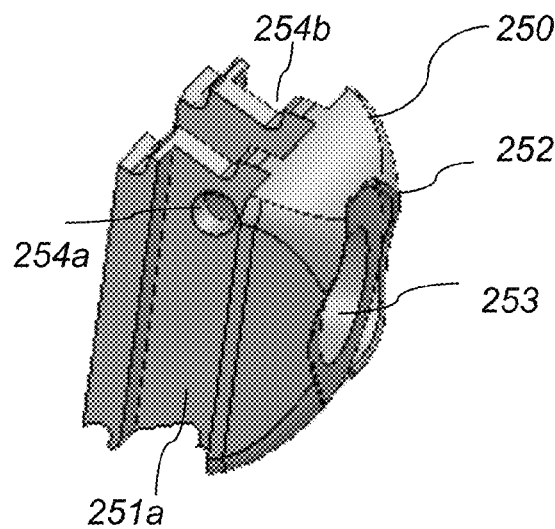
FIG. 16 is a perspective view of the front component of the intervertebral implant of FIG. 14A.

Referring to FIG. 15A-FIG. 16, bottom endplate 230 includes a bottom surface 237a, a top surface 237b, a first protrusion 238a extending along the plate axis 239 and a second protrusion 238b extending perpendicular to the top surface 237b. Second protrusion 238b has an elongated through opening 233. Bottom surface 237a has teeth 234 and the top surface has an inclined surface area 232. Through-openings 231 extend from the top surface 237b to the bottom surface 237a of the bottom endplate 230. Top endplate 220 has a similar structure as the bottom plate 230 and includes a top surface 227a, a bottom surface 227b, a first protrusion 228a extending along the plate axis 229 and a second protrusion 228b extending perpendicular to bottom surface 227b. Second protrusion 228b has an elongated through opening 223. Top surface 227a has teeth 234 and the bottom surface 227b has an inclined surface area 222. Through-openings 221 extend from the top surface 227a to the bottom surface 227b of the to endplate 220.

Wedged basket 210 has a conical shape and includes top and bottom inclined surfaces 211a, 211b, respectively, and left and right inclined side surfaces 211c, 211d. Wedged basket 210 has an open back side 216 and a threaded opening 215 in the front. Each of the top and bottom inclined surfaces 211a, 211b has elongated through openings 217 and a wedged shaped protrusion 218. The side surfaces 211c, 211d have a lattice structure. The inclination angle of the top and bottom surfaces 211a, 211b match the inclination angles of the inclined surface areas 222, 232 of the top endplate 220 and the bottom endplate 230, respectively. Top and bottom endplates 220, 230 slide along inclined surfaces 211a, 211b of the wedged basket, respectively, as the wedged basket moves forwards along 203a or backwards. Wedged shaped protrusion 218 is shaped and sized to slide within a complementary shaped recess formed on the corresponding bottom surface of the top endplate or the corresponding top surface 235 of the bottom endplate.

Actuator 240 includes an elongated cylindrical threaded body 242, a bulleted front end 241 and a hexagonal shaped back end 243. The threaded body 242 has threads that are shaped and sized to engage the inner threads of the front opening 215 of the wedge basket 210. The hexagonal back end 243 is sized and shaped to be engaged by the distal end of an inserter.

Front component 250 has a rounded front surface 252, a front through opening 253, vertical side recesses 251a, 251b, vertical back recess 255 and side openings 254a, 254b. Through-opening 253 is shaped and sized to let the threaded body 242 of the threaded actuator 240 to pass through and to retain the bulleted front end 241 of the actuator 240 at the front surface 252. Vertical protrusions 238b and 228b of the bottom and top endplates 230, 220 are shaped and sized to slide within vertical side recesses 251b and 251a, respectively. Pins 236a, 236b pass through the elongated openings 223 and 233 of the second extensions 228b and 238b and through side opening 254a, and 254b formed on the recessed sides 251a, 251b of the front component 250, respectively and thereby they movably connect the top and bottom endplates 220, 230 to the front component 250. The range of the vertical motion of the top and bottom endplates 220, 230 along directions 202a, 202b is determined by the height of the elongated openings 223, 233, respectively. First protrusions 238a, 228b of the bottom and top endplates 230, 220 are shaped and sized to slide within the bottom and top of the vertical back recesses 255, respectively.

The back side of this intervertebral implant 200 is fully open and fusion promoting bone graft material may be inserted from the back side of the intervertebral implant 200 after the implant has been inserted and expanded. The open side holes of the lattice structure of the wedge and the openings 221 and 231 of the top and bottom endplates 220, 230, respectively, allow blood flow all around the implant, and this promotes fusion throughout the implant.

Figure 17A:
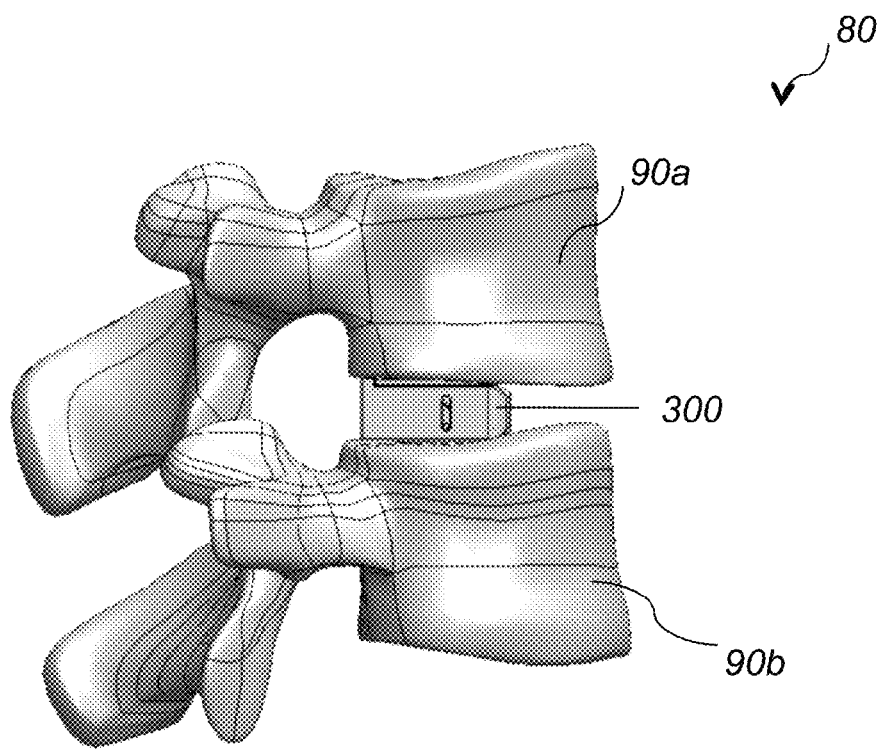
FIG. 17A is a schematic side view of an intervertebral implant that is inserted between two neighboring vertebras and expands upwards, according to this invention.
Figure 17B:
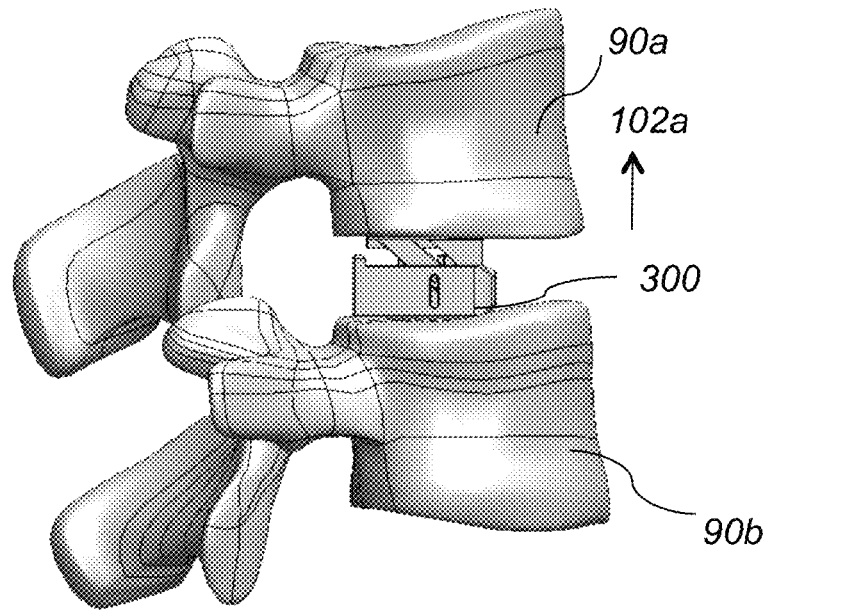
FIG. 17B is a schematic side view of the intervertebral implant of FIG. 17A in the "expanded" configuration.

Referring to FIG. 17A, in another embodiment, intervertebral implant 300 is inserted between neighboring vertebras 90a and 90b. Once inserted in the intervertebral disk space, intervertebral implant 300 expands upwards along direction 102a, as shown in FIG. 17B. Intervertebral implant 300 is used in posterior, trans-foraminal to extra-foraminal implantation procedures. Intervertebral implant 300 has a small sized cage and a compact-sized expansion mechanism. The expansion mechanism allows the cage to be expanded in height after the implant is inserted into the intervertebral space. The height of the cage may be expanded in the range of 6 mm-16 mm.

Figure 18A:
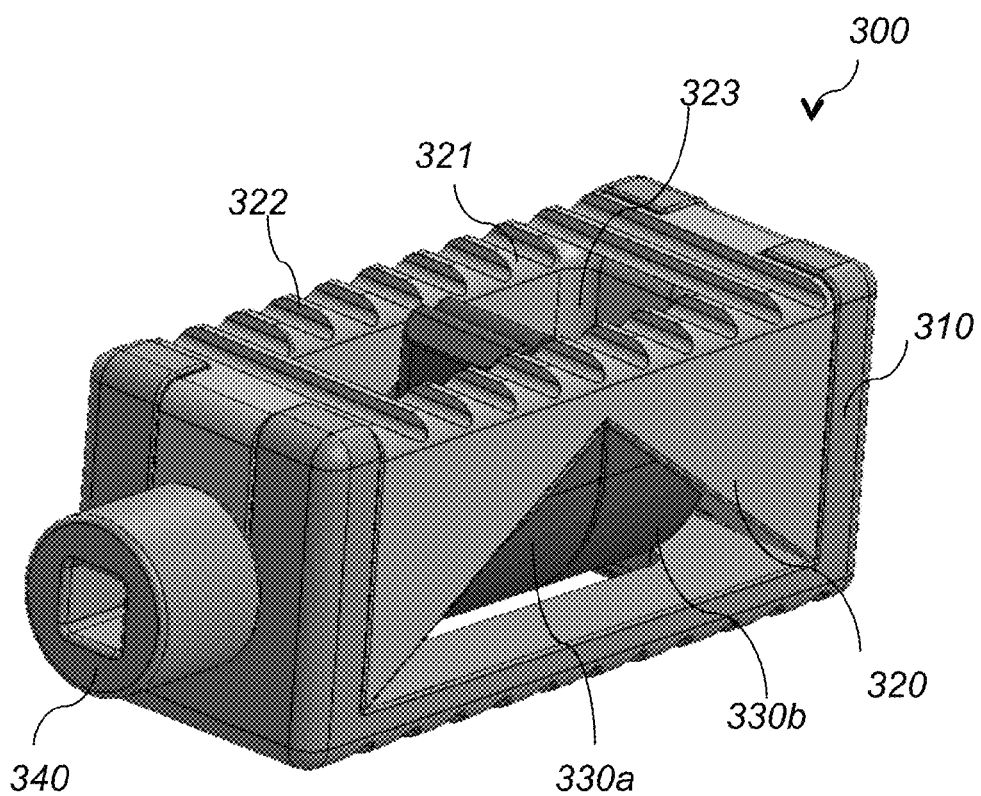
FIG. 18A is a perspective view of the intervertebral implant of FIG. 17A in the "collapsed" configuration.
Figure 18B:
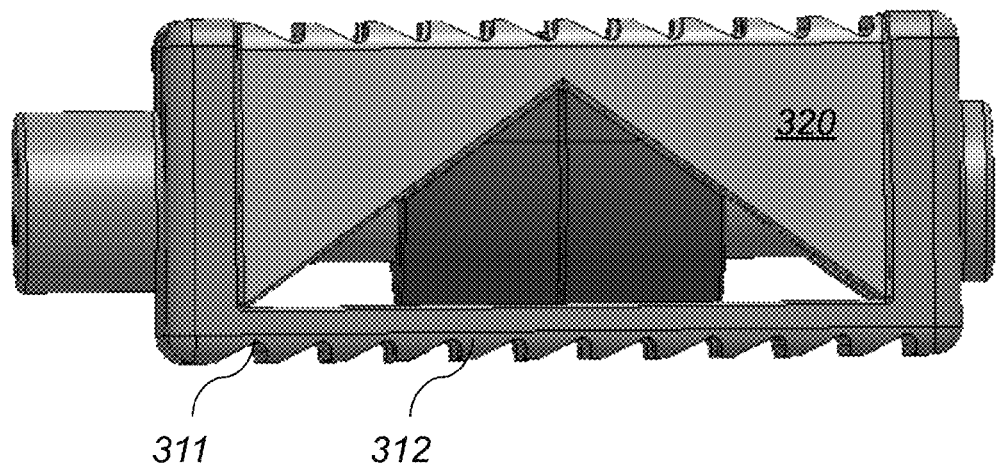
FIG. 18B is a side view of the intervertebral implant of FIG. 18A.
Figure 19A:
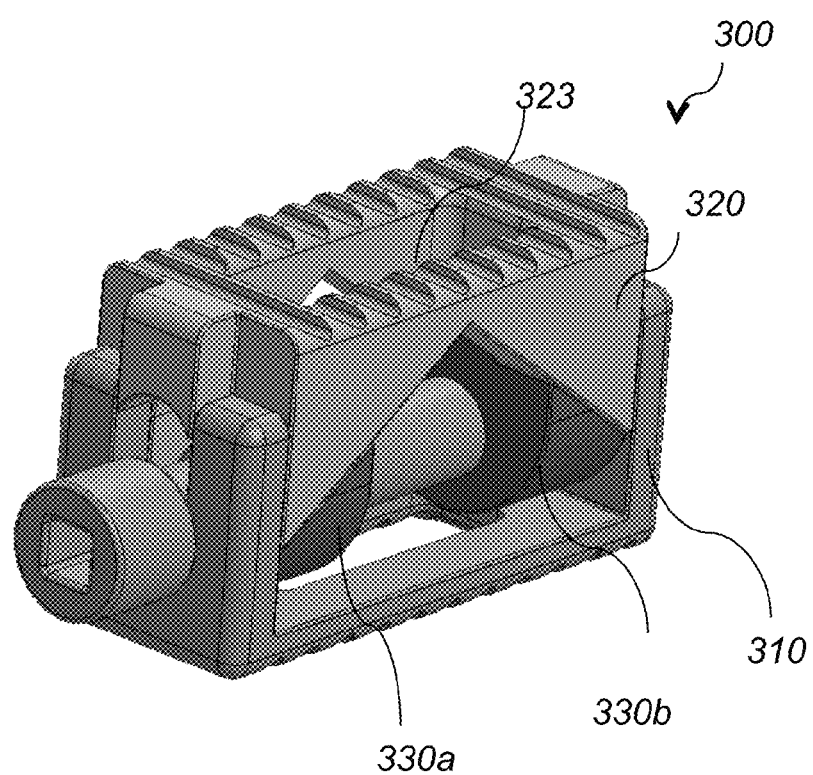
FIG. 19A is a perspective view of the intervertebral implant of FIG. 18A in the "expanded" configuration.
Figure 19B:
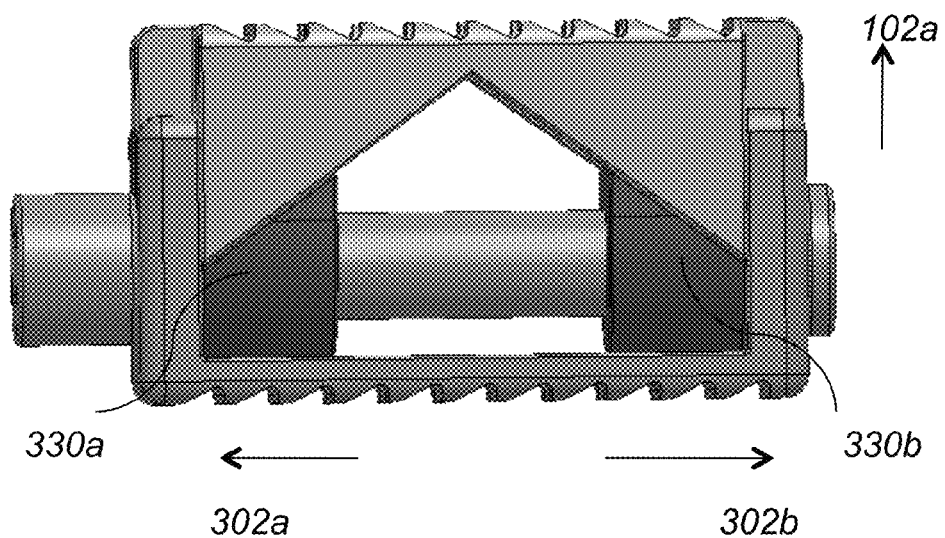
FIG. 19B is a side view of the intervertebral implant of FIG. 18A in the "expanded" configuration.
Figure 20A:
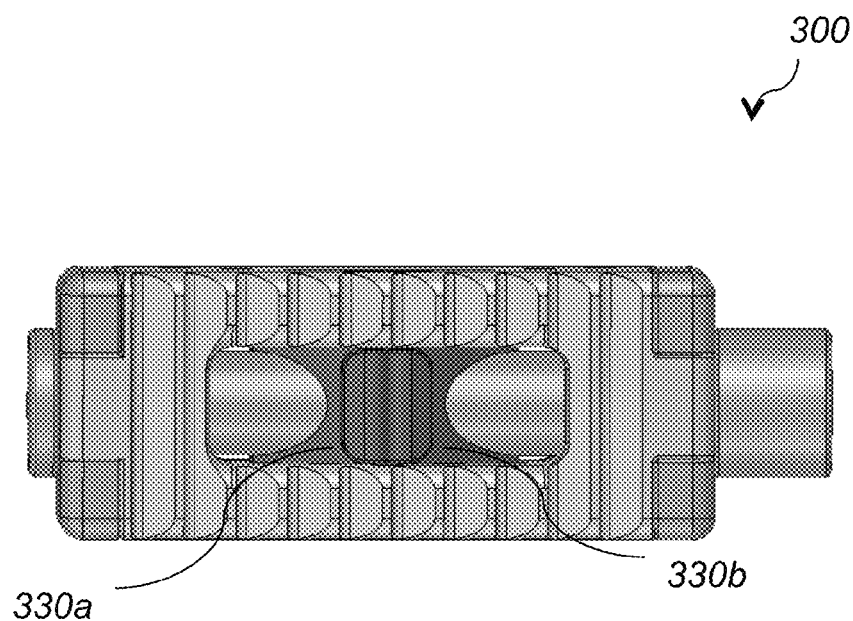
FIG. 20A is a top view of the intervertebral implant of FIG. 18A in the "collapsed" configuration.
Figure 20B:
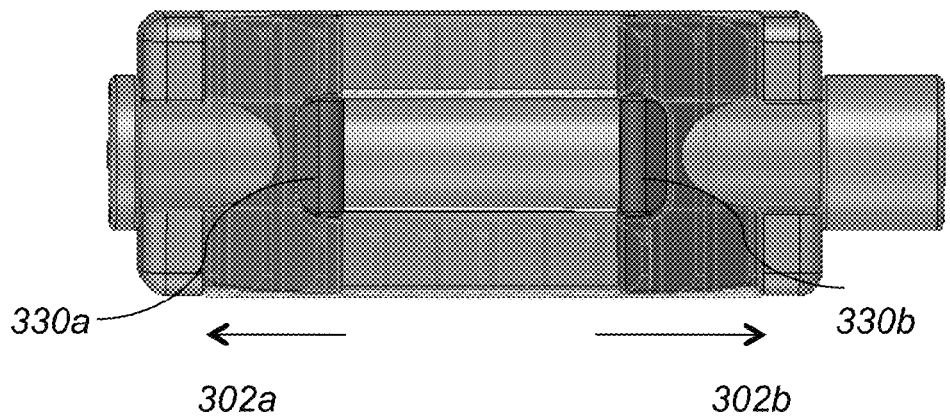
FIG. 20B is a top view of the intervertebral implant of FIG. 18A in the "expanded" configuration.
Figure 21:
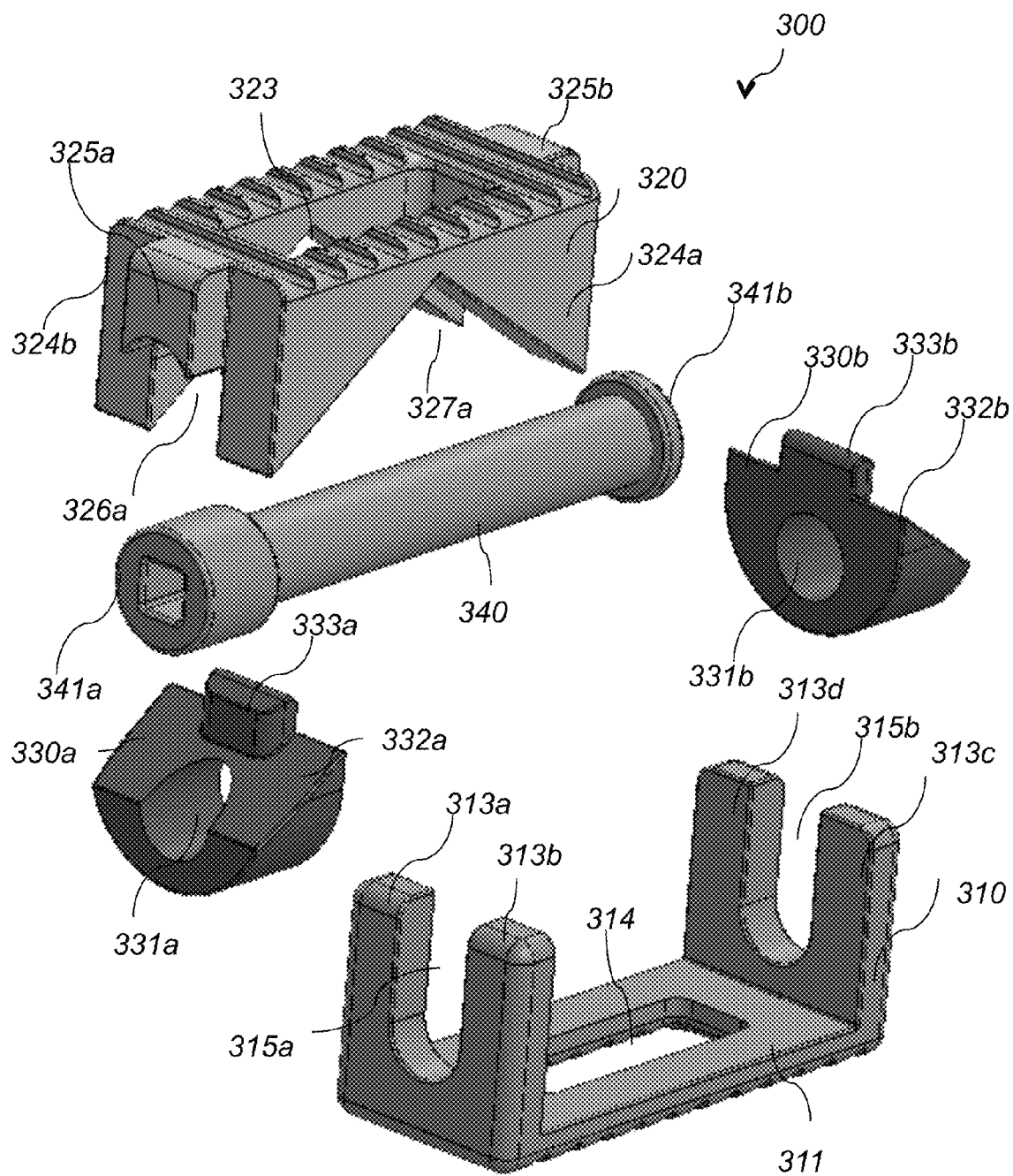
FIG. 21 is an exploded view of the intervertebral implant of FIG. 18A.
Figure 22A:
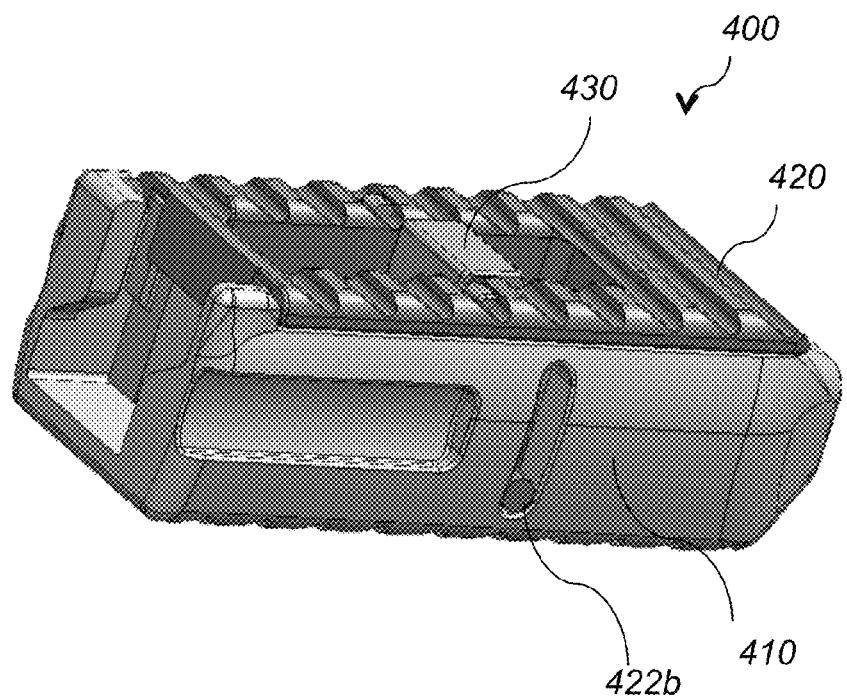
FIG. 22A is a perspective view of another example of the intervertebral implant of FIG. 17A in the "collapsed" configuration.
Figure 22B:
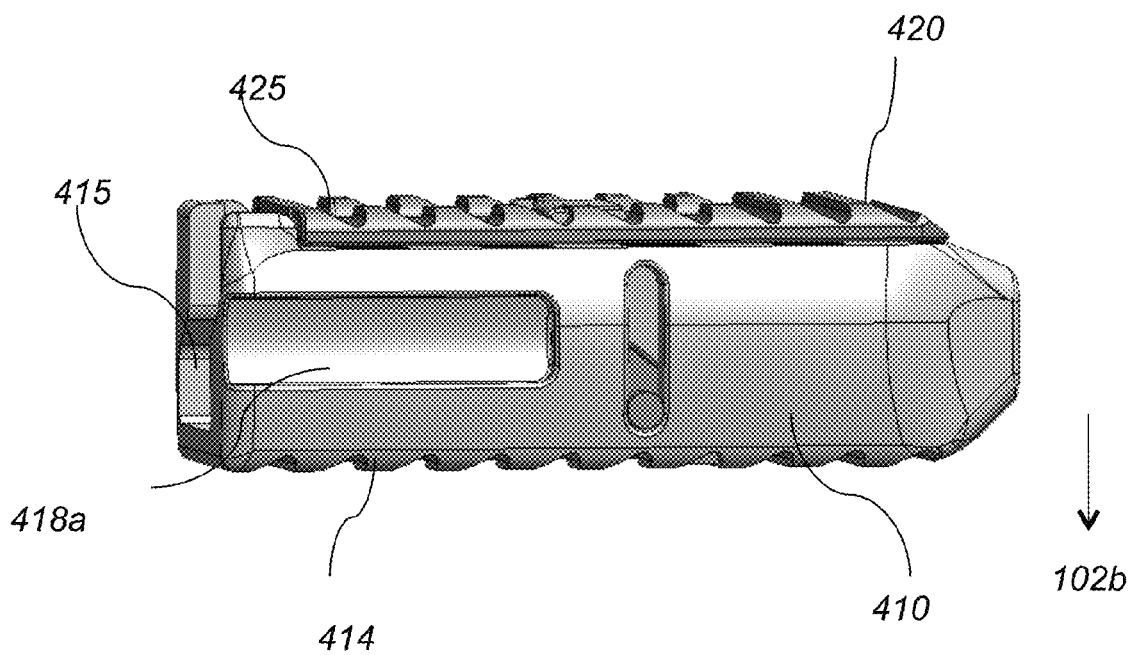
FIG. 22B is a side view of the intervertebral implant of FIG. 22A.

Referring to FIG. 18A-FIG. 21, intervertebral implant 300 includes a base 310, a single endplate 320, wedges 330a, 330b and an actuator rod 340. Endplate 320 is shown to be a top endplate that expands upwards along direction 102a. However, in other embodiments endplate 320 may be a bottom endplate that expands downwards. Base 310 includes a plate 312 having teeth on its bottom surface and four protrusions 313a-313d extending upwards from the four corners of the plate's top surface. The center of the plate has a through opening 314. Endplate 320 includes a top plate 322 and sides 324a and 324b. Top plate 322 has teeth 321 on its top surface and sides 324a, 324b have triangular shaped openings 327a, 327b, respectively. Gaps 326a, 326b are formed between sides 324a, 324b and protrusions 325a, 325b extend downwards into gaps 326a, 326b, respectively, from the front end and back end of the top plate 322. Actuator 340 is a threaded cylinder and has a front end 341a and a back end 341b. Wedge 330a includes an inclined surface 332a, a through opening 331a and an upwards extending protrusion 333a. Similarly, wedge 330b includes an inclined surface 332b, a through opening 331b and an upwards extending protrusion 333b. Actuator rod 340 is inserted into openings 331a and 331b of wedges 330a, 330b, respectively, and wedges 330a, 330b are oriented so that their inclined surfaces 332a, 332b are sloped downwards, as shown in FIG. 21. Wedges 330a, 330b with the inserted actuator rod 340 are inserted in the base 310 so that the actuator rod is supported within gaps 315a, 315b formed between upward extending protrusions 313a and 313b and between upward extending protrusions 313c and 313d, respectively. Ends 341a, 341b of the actuator rod 340 protrude from the gaps 315a, 315b, respectively, as shown in FIG. 18A. Endplate 320 is placed on top of base 310 so that protrusions 325a, 325b slide within gaps 325a and 315b of the base 310, as shown in FIG. 18A. In the collapsed configuration, wedges 330a, 330b are next to each other in the center of the intervertebral assembly 300, a shown in FIG. 18B. The inclined surfaces 332a, 332b of wedges 330a, 330b are configured to match and slide along the inclined inner surfaces of the triangular shaped openings 327a, 327b of the endplate 320. Rotating the actuator rod 340 clockwise moves wedges 330a, 330b outwards along directions 302a, 302b, respectively, and raises the endplate 320 upwards along direction 102a, as shown in FIG. 19B. Reversing the actuator rod rotation direction, moves the wedges 330a, 330b back to the center of the intervertebral assembly 300 and collapses the intervertebral assembly 300. In the expanded configuration, the sides 327a, 327b of the intervertebral assembly 300 are open and are filled with fusion promoting bone graft material.

Referring to FIG. 22A-FIG. 26, in another embodiment, upwards expanding intervertebral implant 400 includes a base body 410, a single top endplate 420, a center component 430 and an actuator rod 440. Endplate 420 is shown to be a top endplate that expands upwards along direction 102a. However, in other embodiments endplate 420 may be a bottom endplate that expands downwards. Base body 410 has an open back side 417 and includes a base plate 414 having teeth 414a on its bottom surface, left side 411a, right side 411b and front 412. The center of the base plate 414 has an elongated through opening 415. Sides 411a and 411b include vertically extending elongated slots 416a, 416b, respectively. In this example, the outer surfaces of sides 411a, 411b include recesses 418a, 418b, respectively, that are shaped and sized to receive grasping protrusions of an inserter tool, as will be described below. In other examples, recesses 418a, 418b are formed in the inside surfaces of sides 411a, 411b. Front 412 includes a protrusion 413 and a through opening 413a.

Endplate 420 includes a top plate 425 and sides protrusions 423a and 423b, 421a and 421b. Top plate 425 has teeth 425a on its top surface, a central through-opening 426 and two through-openings 427a, 427b located left and right of the central opening 426. Side protrusions 421a and 421b and 423a and 423b extend downwards and have surfaces 424a, 424b, and 424e, 424f, and 424c, and 424d, respectively, that are inclined and form an angle 424 with the base body axis 99. Side protrusions 421a, 421b also include cylindrical protrusions 422a, 422b, respectively.

Center component 430 includes sides 436a, 436b, front 434 and an open back side. Front 434 includes a through-opening 435 and sides 436a and 436b include protrusions 433a, 433c and 433b, 433d, respectively. Protrusions 433a, 433c and 433b, 433d have inclined surfaces that match and complement the inclined surfaces of the endplate side protrusions 423a and 421a and 423b and 421b, respectively. Center component 430 is placed within the base body 410 so that through-opening 435 is aligned with through-opening 413a. Top plate 420 is placed on top of the center component 430 and the base body 410, so that the inclined surfaces of the side protrusions 423a and 421a and 423b and 421b match and complement the inclined surfaces of the center component protrusions 433a, 433c and 433b, 433d, respectively and cylindrical protrusions 422a, 422b slide within elongated slots 416a, 416b of the base body 410, respectively. Actuator 440 is cylindrically shaped and has a front end 441a and a reversed threaded back end 441b. Actuator rod 440 is inserted into through-openings 413a, 435.

Figure 23A:
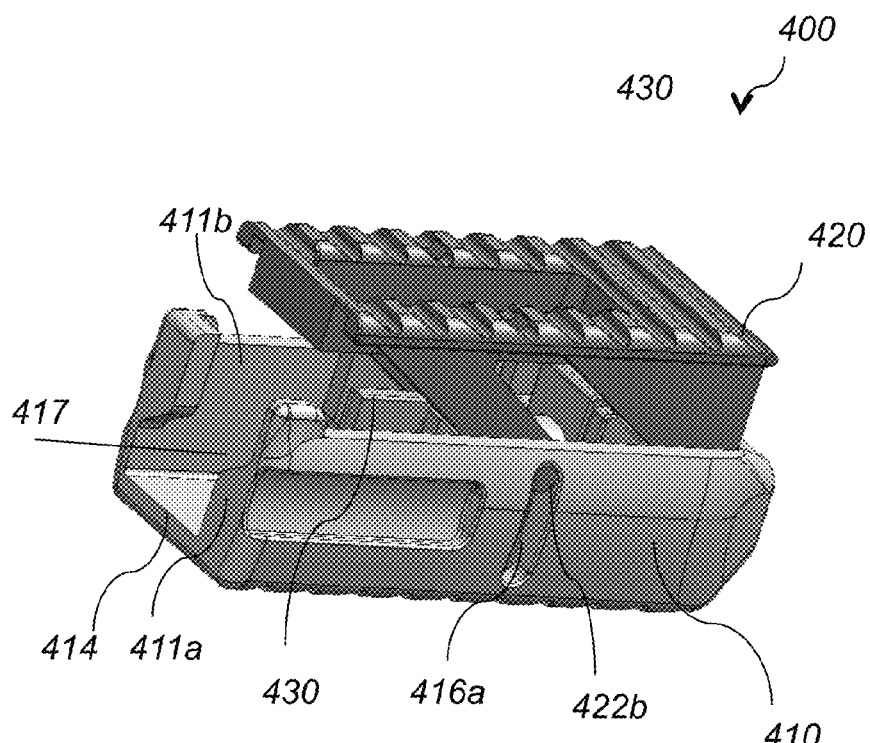
FIG. 23A is a perspective view of the intervertebral implant of FIG. 22A in the "expanded" configuration.
Figure 23B:
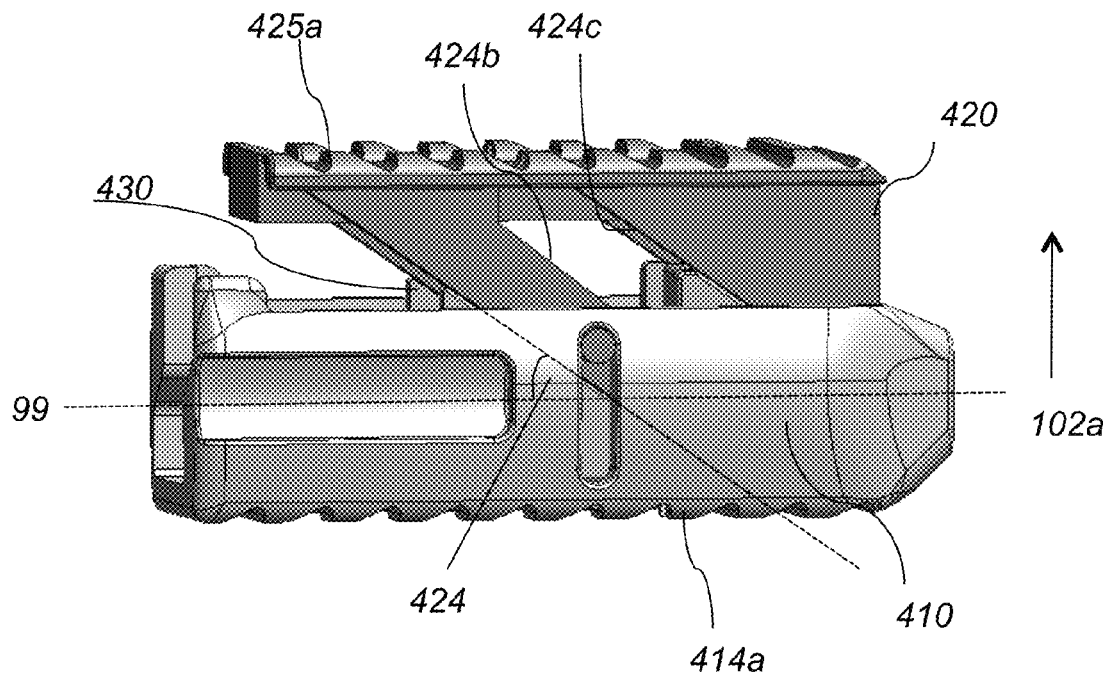
FIG. 23B is a side view of the intervertebral implant of FIG. 22A in the "expanded" configuration.
Figure 24A:
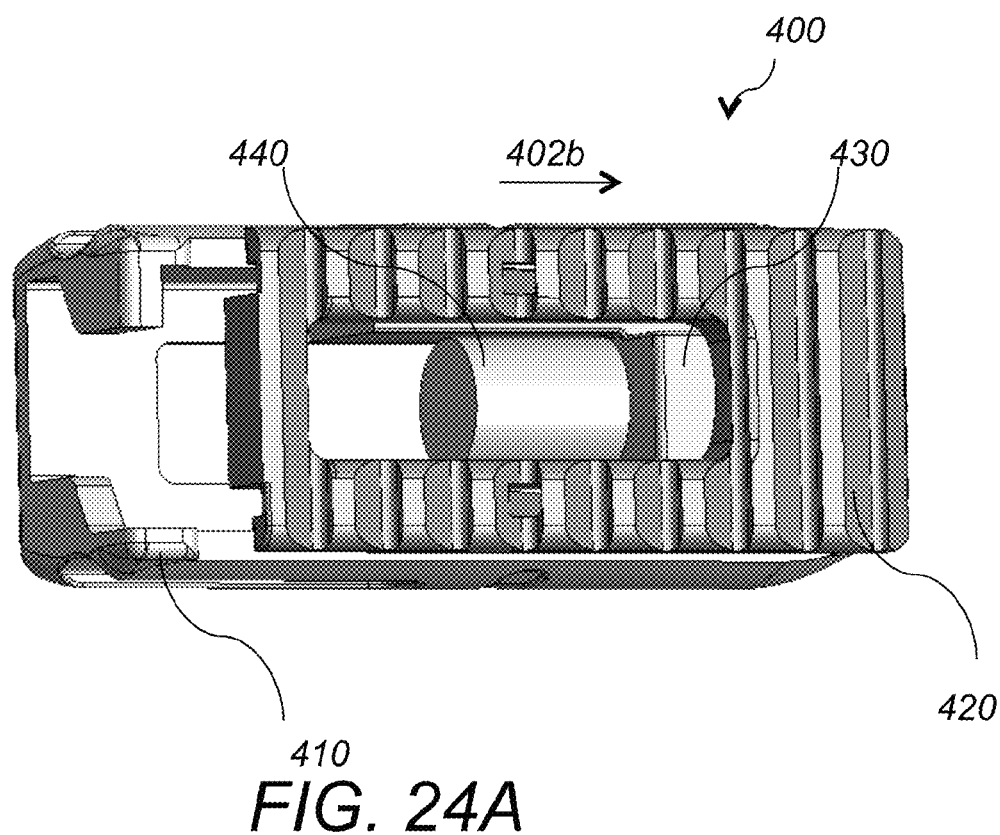
FIG. 24A is a top view of the intervertebral implant of FIG. 22A in the "collapsed" configuration.
Figure 24B:
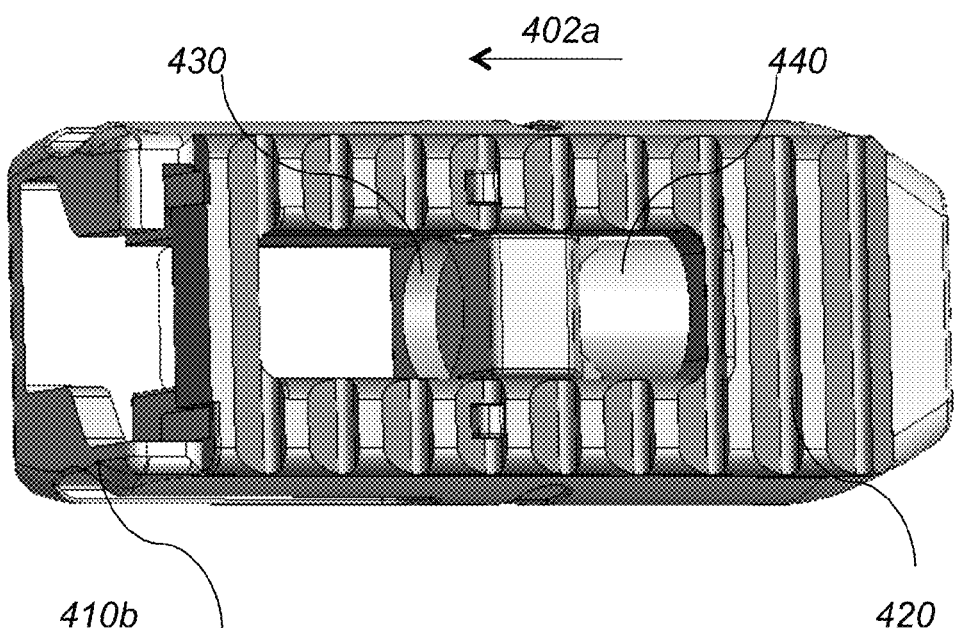
FIG. 24B is a top view of the intervertebral implant of FIG. 22A in the "expanded" configuration.
Figure 25A:
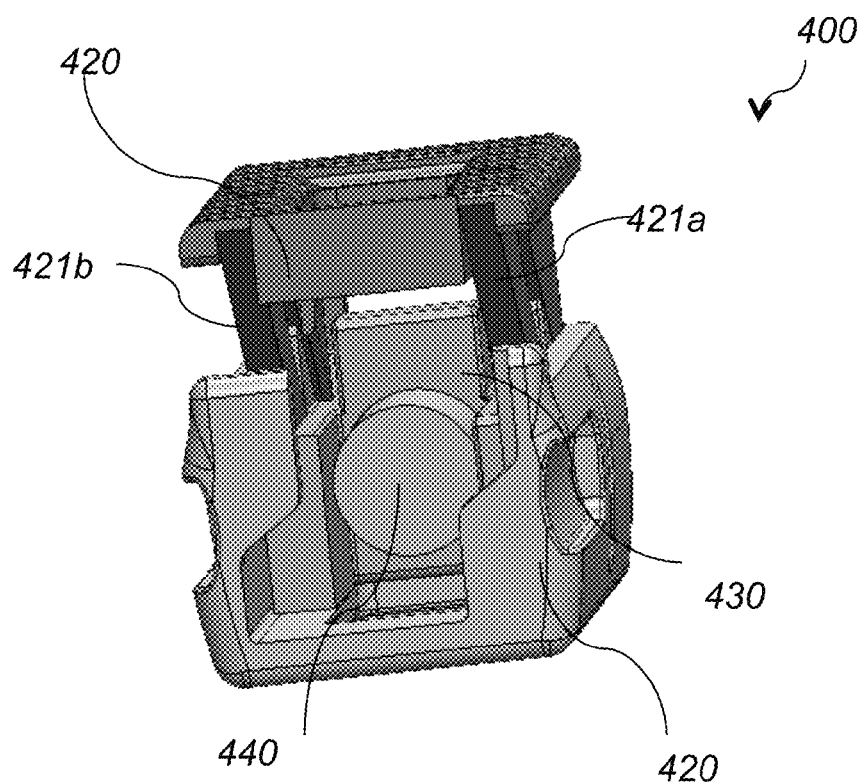
FIG. 25A and FIG. 25B are back views of the intervertebral implant of FIG. 22A in the "expanded" configuration.
Figure 25B:
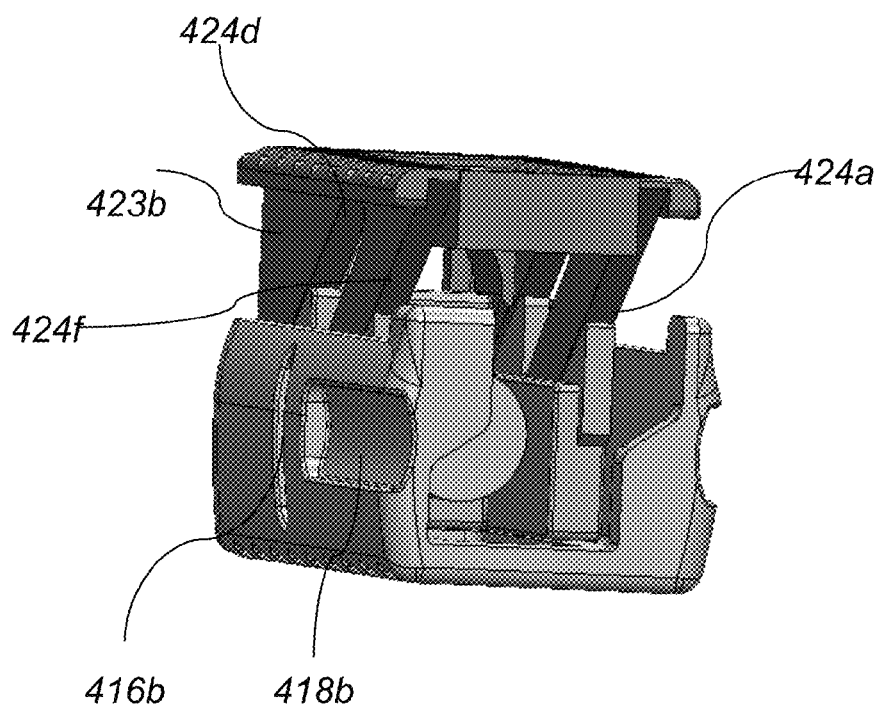
Figure 26:
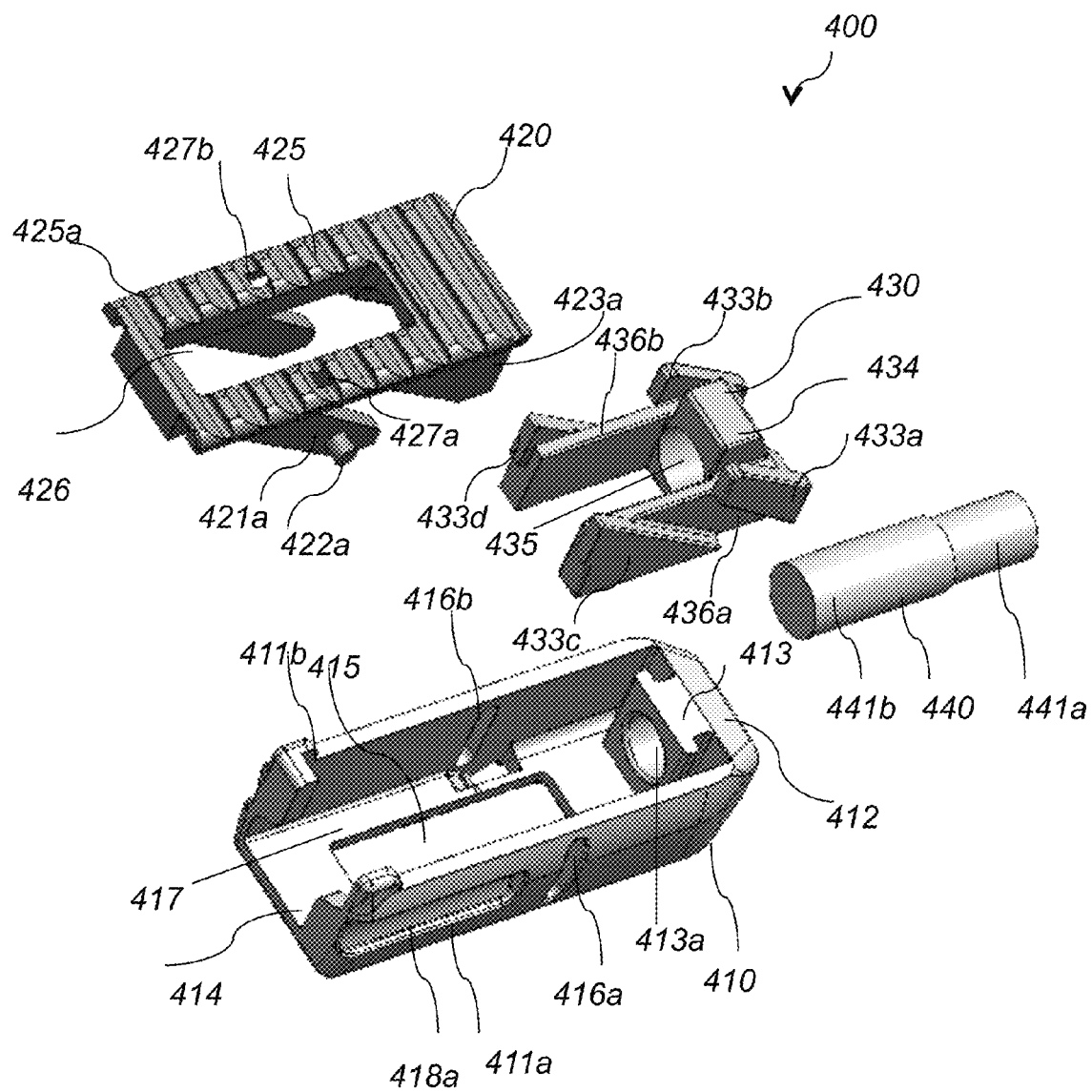
FIG. 26 is an exploded view of the intervertebral implant of FIG. 22A.
Figure 27A:
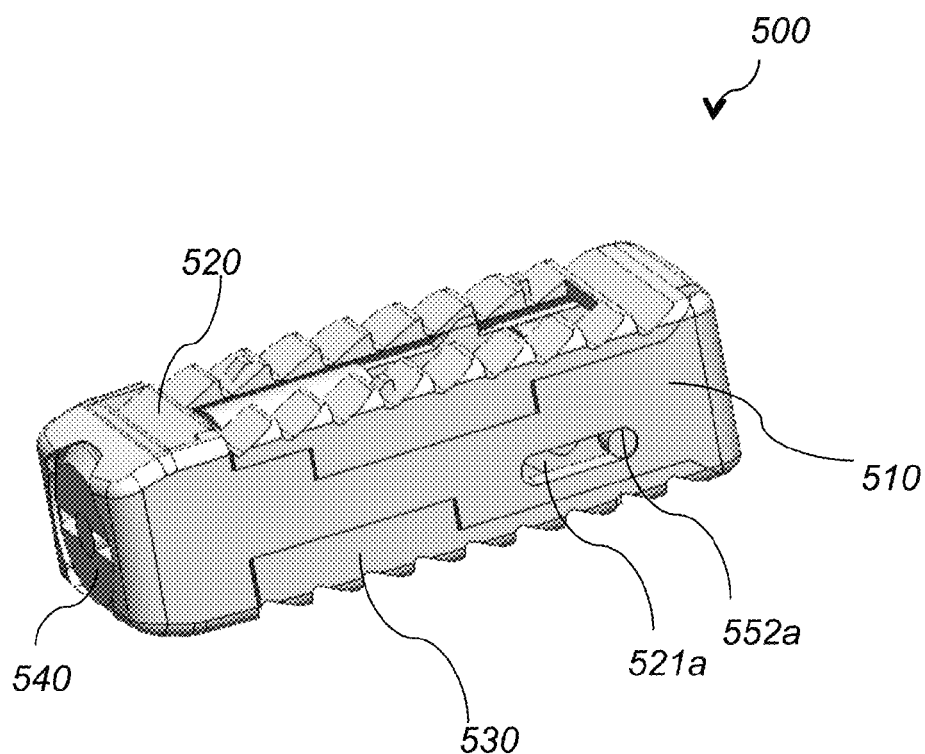
FIG. 27A is a perspective view of another example of the intervertebral implant of FIG. 1A in the "collapsed" configuration.
Figure 27B:
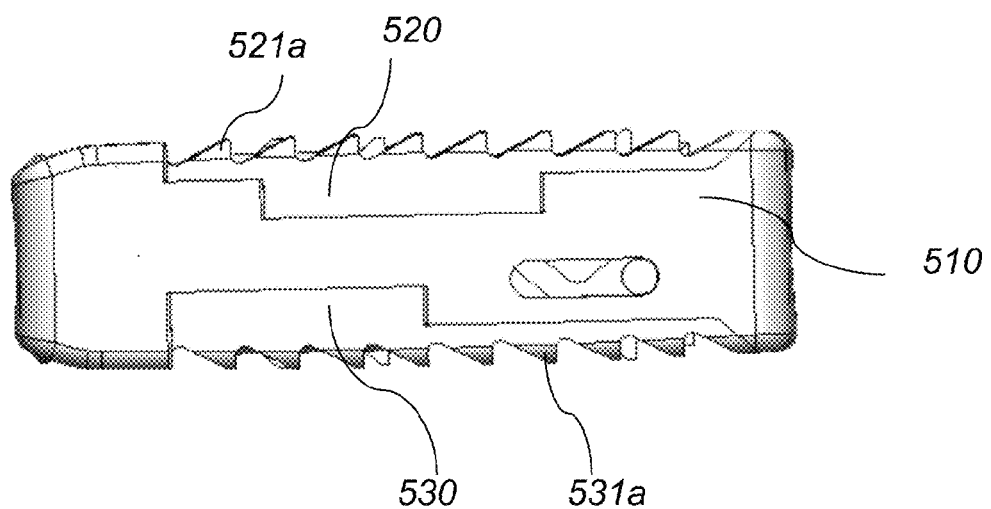
FIG. 27B is a side view of the intervertebral implant of FIG. 27A.
Figure 28A:
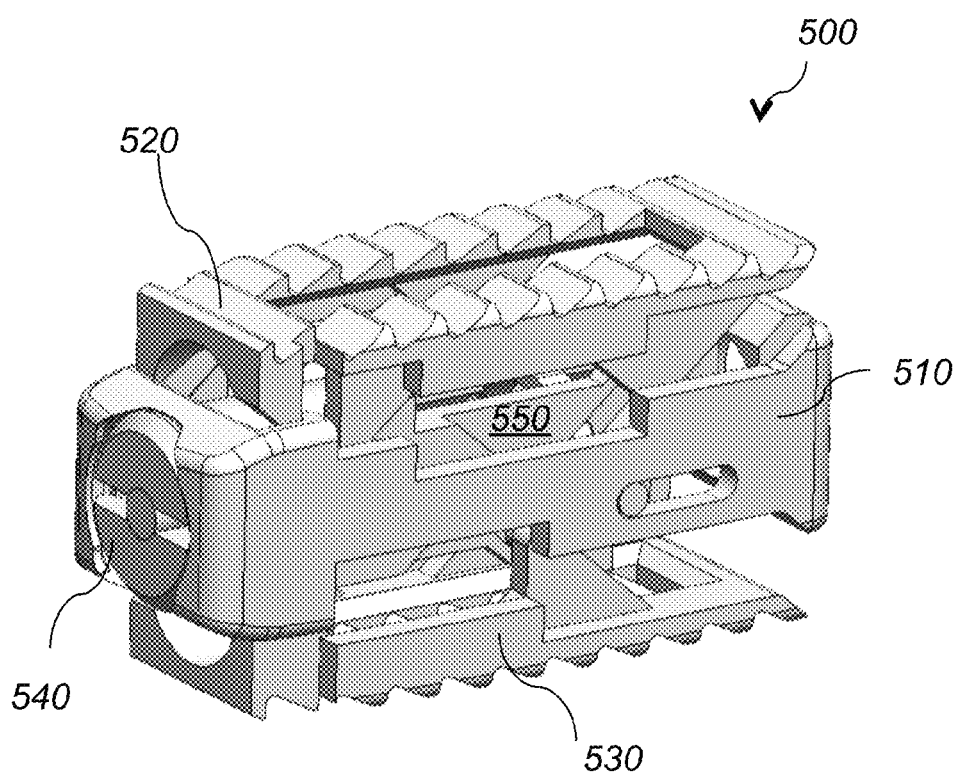
FIG. 28A is a perspective view of the intervertebral implant of FIG. 27A in the "expanded" configuration.
Figure 28B:
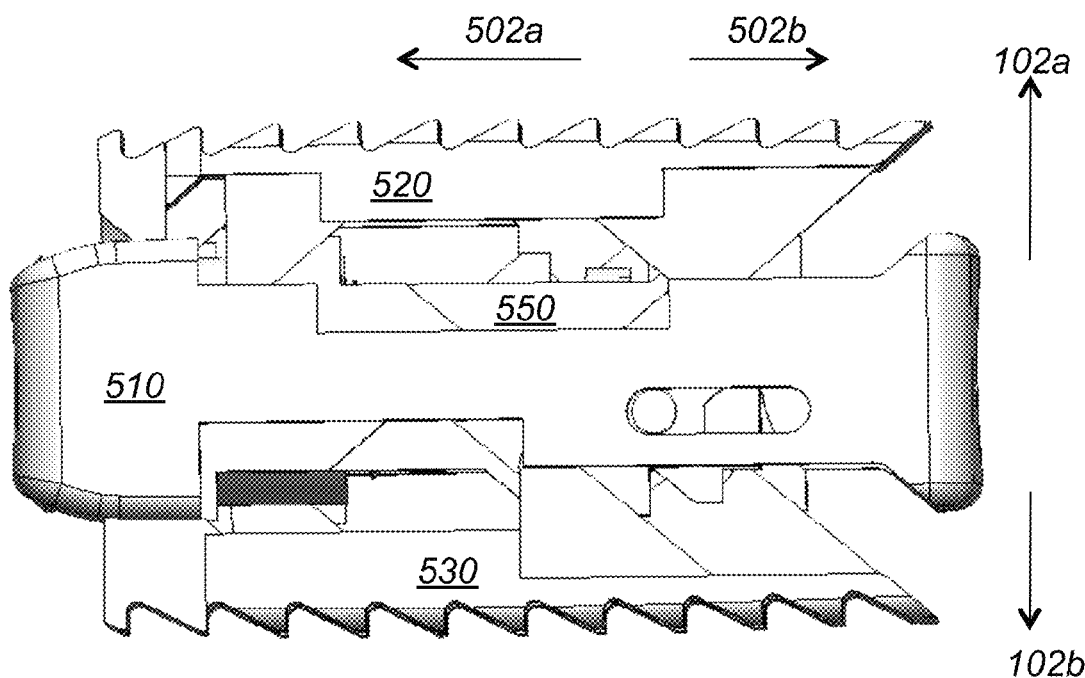
FIG. 28B is a side view of the intervertebral implant of FIG. 27A in the "expanded" configuration.
Figure 29:
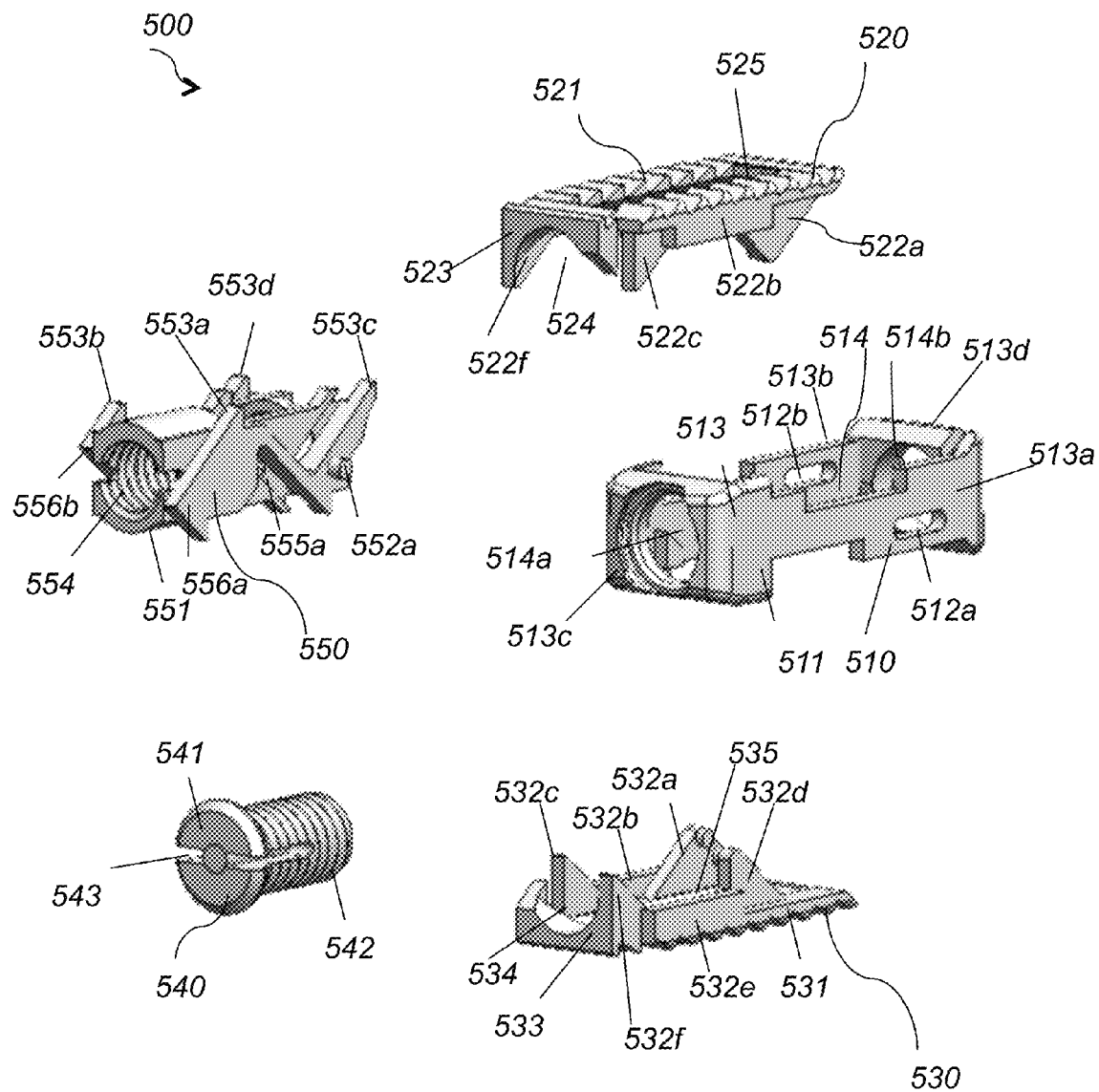
FIG. 29 is an exploded view of the intervertebral implant of FIG. 27A.

Rotating the actuator rod 440 clockwise moves the center component 430 along direction 402b and causes the side protrusions of the top endplate 420 to slide up on the corresponding inclined surfaces of the center component 430, and thereby moves the top endplate 420 upwards along 102a, as shown in the expanded configuration of FIG. 23B. Rotating the actuator rod 440 counter-clockwise moves the center component 430 along 402a and causes the side protrusions of the top endplate to slide down on the corresponding inclined surfaces of the center component 430, and thereby moves the top endplate 420 downwards along 102b, as shown in the collapsed configuration of FIG. 22B.

In this embodiment, fusion extends through the middle of the intervertebral implant through openings 426, and 415. In the expanded configuration, the back side 417 of the intervertebral implant 400 is open and is filled in situ with fusion promoting bone graft material.

Figure 37A:
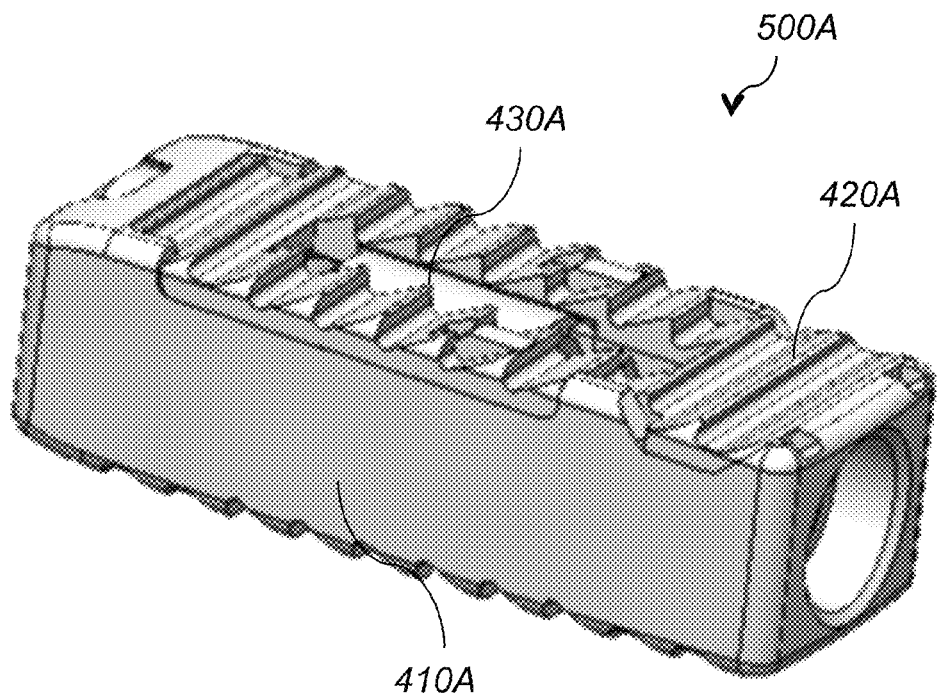
FIG. 37A is a perspective view of another example of the intervertebral implant of FIG. 17A in the "collapsed" configuration.
Figure 37B:
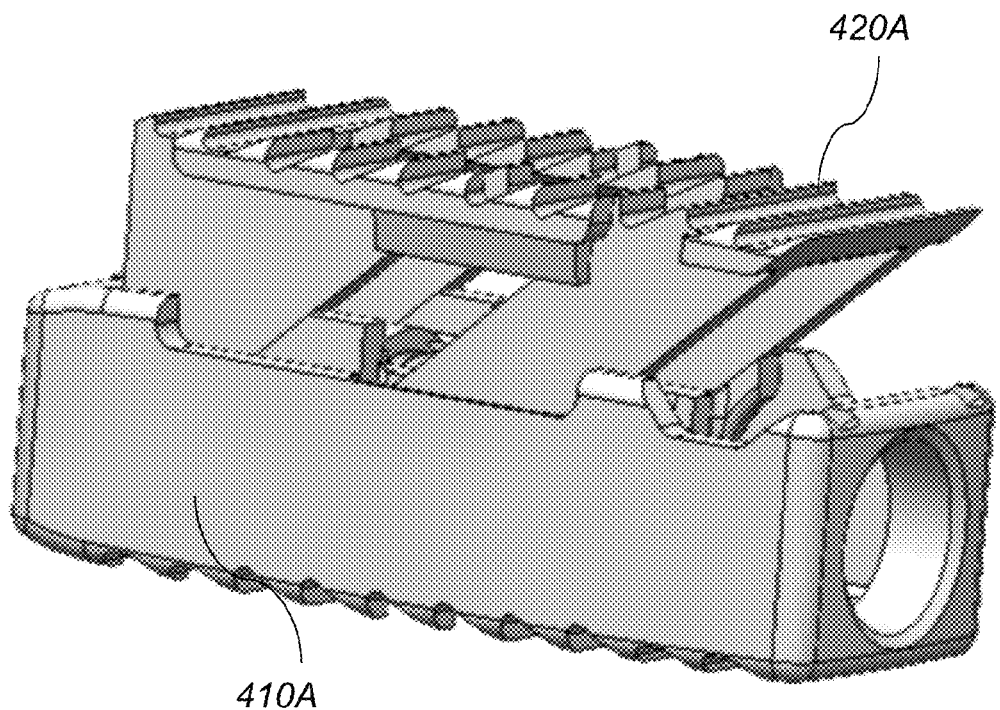
FIG. 37B is a perspective view of the intervertebral implant of FIG. 37A in the "expanded" configuration.
Figure 37C:
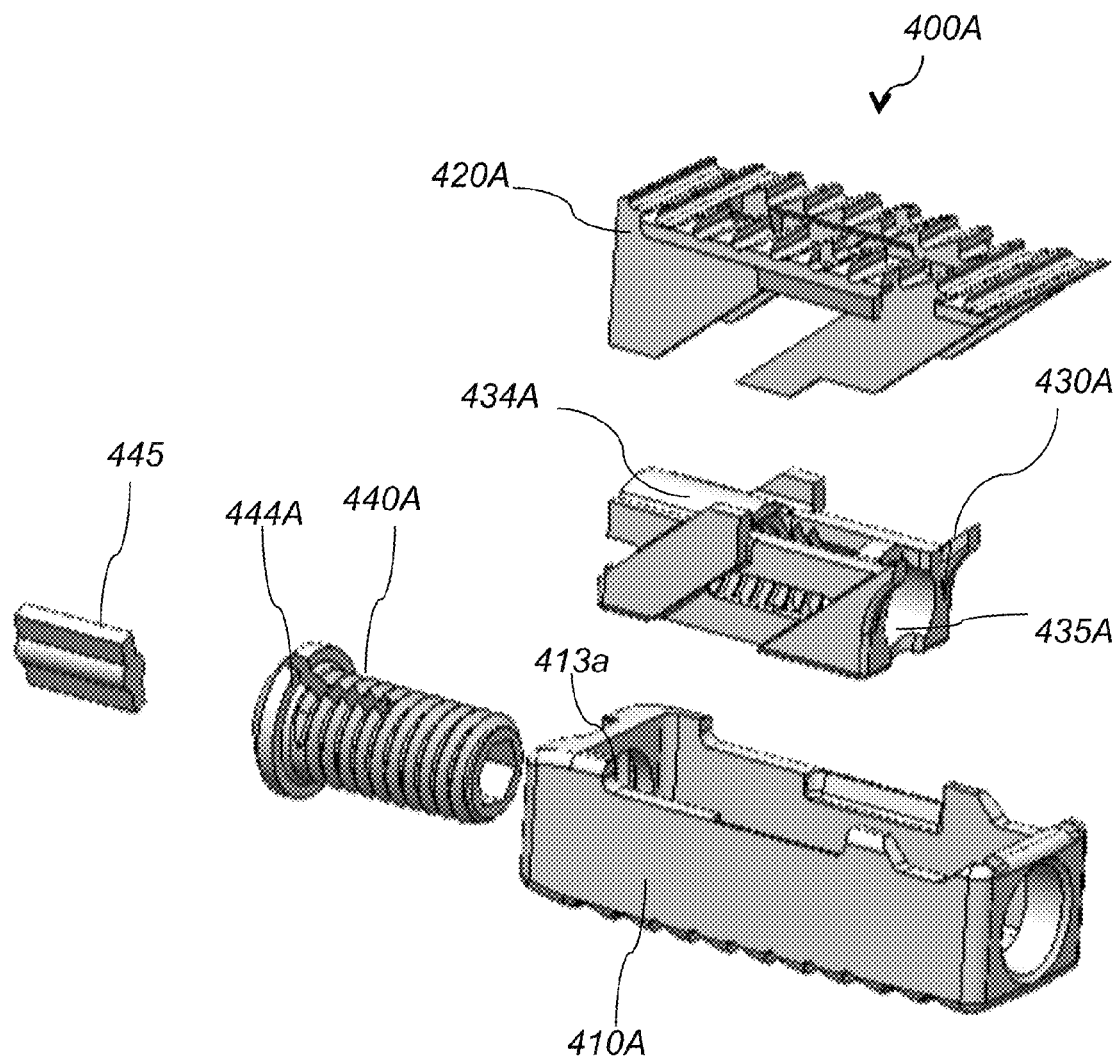
FIG. 37C is an exploded view of the intervertebral implant of FIG. 37A.

Referring to FIG. 37A-FIG. 37C, in another embodiment, upwards expanding intervertebral implant 400A includes a base body 410A, a single top endplate 420A, a center component 430A and an actuator rod 440A. In this embodiment, center component 430A includes a front component 434A that has a threaded through-opening 435A and extends past the middle of component 430A. Center component 430A is placed within the base body 410A so that through-opening 435A is aligned with through-opening 413a. Actuator 440A is cylindrically shaped and has a threaded outer surface. Actuator 440A also includes a slot 444A that is sized and shaped to receive key 445. Actuator rod 440 is inserted and threaded into through-openings 413a, 435A.

Referring to FIG. 27A-FIG. 29, in another embodiment, intervertebral implant 500 expands upwards and downwards with the same sliding mechanism, as in the above described intervertebral implant 400. Expanding intervertebral implant 500 includes a center body 510, a top endplate 520, a bottom endplate 530, a center component 550 and an actuator rod 540. Center body 510 includes sides 513a, 513b, 513c and 513d and a central top to bottom extending opening 514. Side 513c includes a threaded opening 514a and side 513d has a through opening 514b. Sides 513a and 513b include elongated horizontal slots 512a, 512b, respectively. Center component 550 is placed within center body 510 and includes a body 551, threaded through-opening 554 and side protrusions 553a, 553b, 553c, 553d with inclined surfaces. Center component also includes inclined side recesses 555a, 555b and cylindrical side protrusions 552a, 552b that are configured to slide within the elongated horizontal slots 512a, 512b of the center body 510, respectively.

Top endplate 520 includes a top plate 521 and sides protrusions 522a, 522b, 522c, 523d, 522e, 522f. Top plate 521 has teeth 521a on its top surface and a central through-opening 525. Side protrusions 522a 522c, 522d, 522f extend downwards and have inclined surfaces that match and complement corresponding inclined surfaces of the side protrusions 553c, 553a, 553d, 553b of the center component 550.

Bottom endplate 530 includes a bottom plate 531 and sides protrusions 532a, 532b, 532c, 532d, 532e, 532f. Bottom plate 531 has teeth 531a on its bottom surface and a central through-opening 535. Side protrusions 532a 532c, 532d, 532f extend upwards and have inclined surfaces that match and complement corresponding inclined surfaces of recesses 555a, 555b, and protrusions 556a, 556b of the center component 550.

Actuator 540 has a threaded cylindrically shaped body 542 and a slotted front end 541. Actuator 540 is inserted into the threaded through-openings 514a and 554. Rotating the actuator 540 clockwise moves the center component 550 along direction 502a and causes the side protrusions of the top endplate 520 and bottom endplate 530 to slide up and down, respectively, on the corresponding inclined surfaces of the center component 550, and thereby moves the top endplate 520 upwards along 102a and the bottom endplate downwards along 102b, as shown in the expanded configuration of FIG. 28B. Rotating the actuator 540 counter-clockwise moves the center component 550 along 502b and causes the side protrusions of the top endplate and bottom endplate to slide down and up, respectively, on the corresponding inclined surfaces of the center component 550, and thereby moves the top endplate 520 downwards along 102b and the bottom endplate 530 upwards along 102a, as shown in the collapsed configuration of FIG. 27B.

Figure 38A:
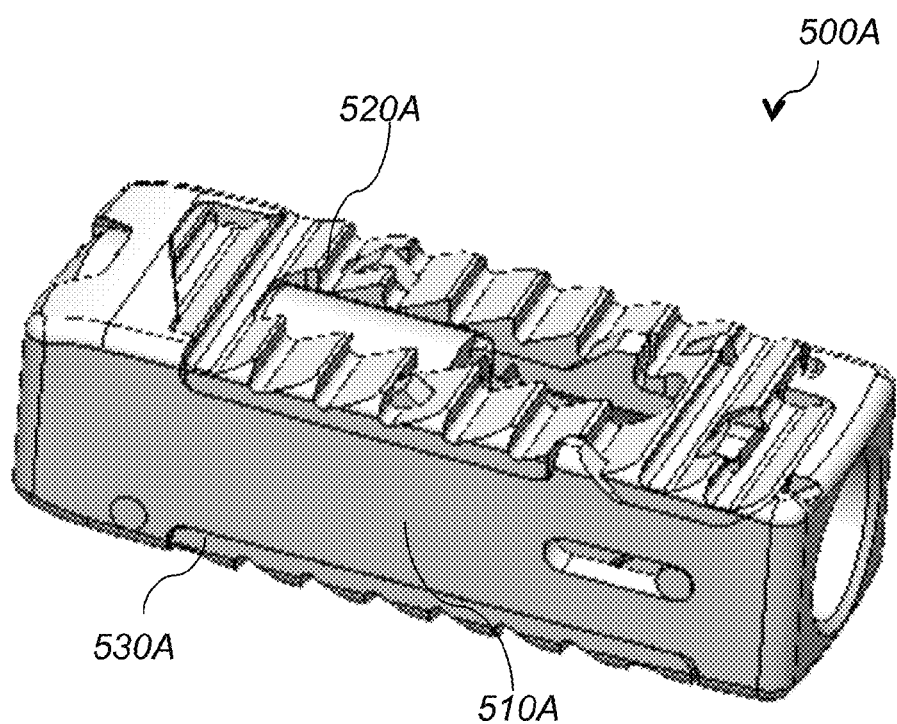
FIG. 38A is a perspective view of another example of the intervertebral implant of FIG. 1A in the "collapsed" configuration.
Figure 38B:
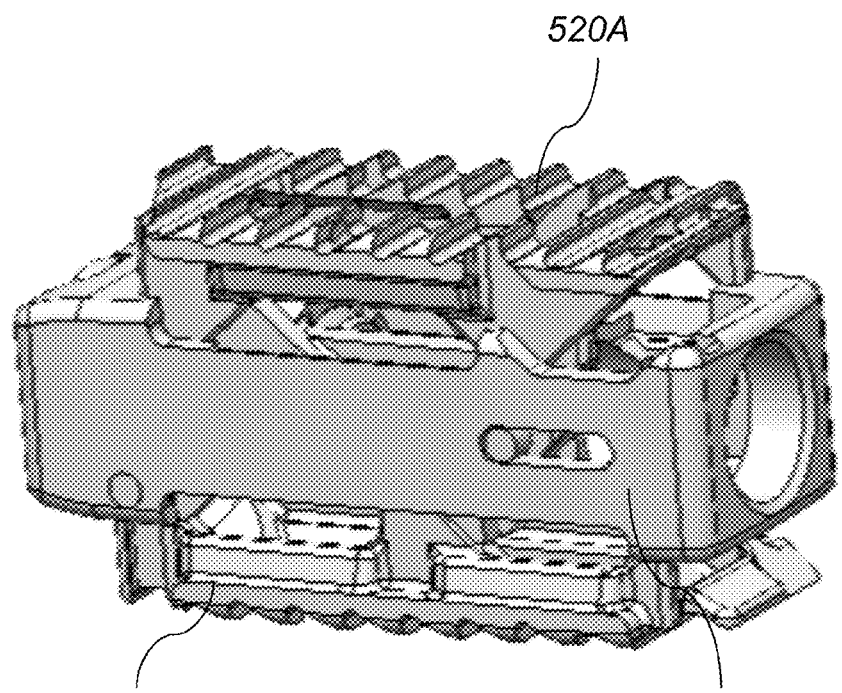
FIG. 38B is a perspective view of the intervertebral implant of FIG. 38A in the "expanded" configuration.
Figure 38C:
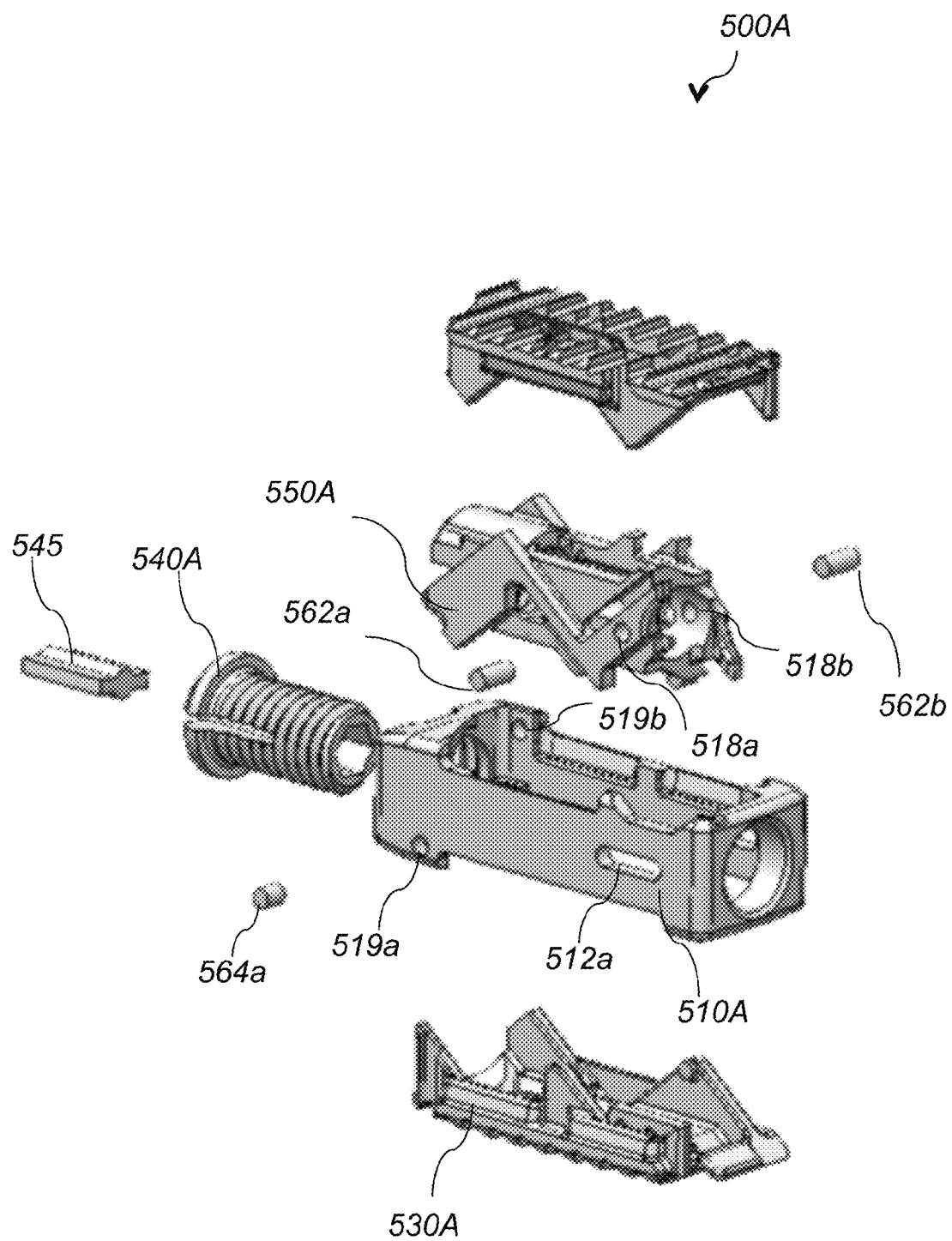
FIG. 38C is an exploded view of the intervertebral implant of FIG. 38A.

Referring to FIG. 38A-FIG. 38C, in another embodiment, intervertebral implant 500A expands upwards and downwards with the same sliding mechanism, as in the above described intervertebral implant 500. Expanding intervertebral implant 500A includes a center body 510A, a top endplate 520A, a bottom endplate 530A, a center component 550A and an actuator rod 540A. In this embodiment, the position of the center component 550A within the center body 510A is secured with removable pins 562a, 562b and 564a, 564b(not shown), that are inserted into openings 519a, 519b, and 512a, 512b, of the center body 510A, respectively. Pins 562a, 562b are also inserted into openings 518a, 518b of the center component 550A, respectively.

Figure 30A:
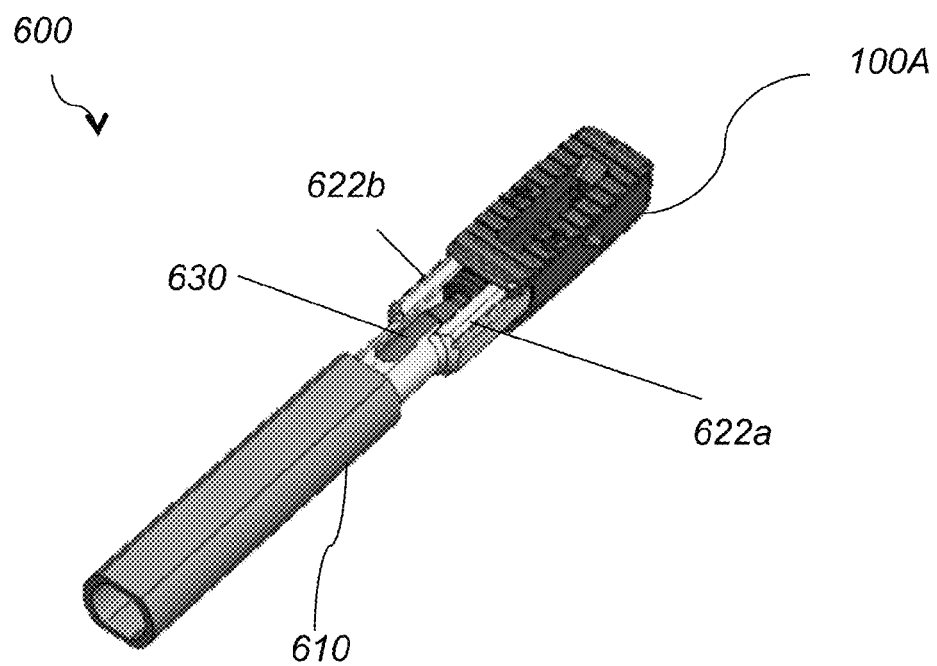
FIG. 30A is a perspective view of an inserter tool for the intervertebral implant of FIG. 1A.
Figure 30B:
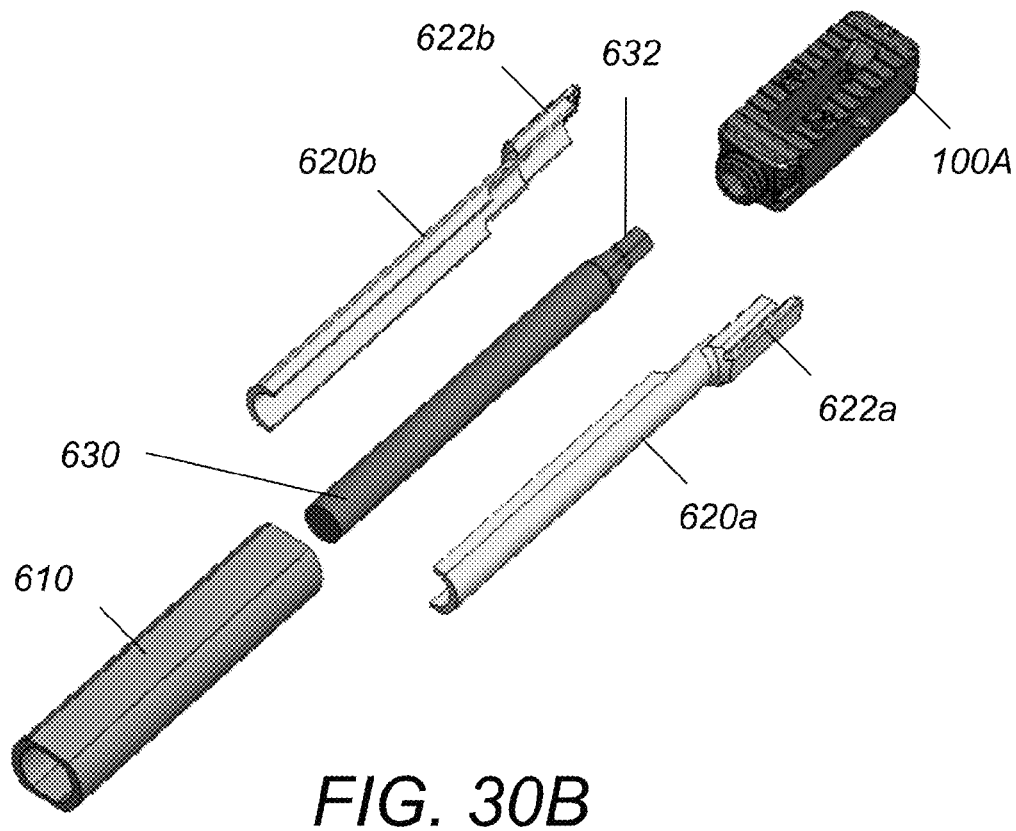
FIG. 30B is an exploded view of the inserter tool of FIG. 30A.

Custom designed inserter tools are used for inserting the above described intervertebral implants in the space between two adjacent vertebras 90a, 90b. Referring to FIG. 30A and FIG. 30B inserter 600 includes an elongated cylindrical shaft 630 that terminated in a hexagonal distal tip 632. Tip 632 complements the shape of opening 145 of the threaded actuator 140 used in the intervertebral implant 100A. Two elongated semi-cylindrical sides 620a, 620b wrap around shaft 630 and terminate in distal protrusions 622a, 622b, respectively. Distal protrusions 622a, 622b are shaped and sized to engage corresponding recesses formed on the outside or the inside surfaces of the center body 110. A hollow cylinder 610 slides over slides 620a, 620b and holds the inserter tool 600 together, as shown in FIG. 30A.

Referring to FIG. 31A-FIG. 32C, inserter 650 includes an elongated cylindrical shaft 680 that terminated in a distal tip 682. Tip 682 complements the shape of front 441b of the actuator rod 440 used in the intervertebral implant 400 of FIG. 26. In this example, tip 682 has a tri-lobe shape, as shown in FIG. 32A. A cylindrical sleeve 670 surrounds shaft 680 and has a front component 672 that is sized to surround the front 441b of actuator rod 440, and is shaped to complement the shape of the front opening 412a of the intervertebral implant 400, as shown in FIG. 32B and FIG. 32C. In this example, front component 672 has top and bottom protrusions 672a, 672b that match top and bottom recesses 673a, 673b in the front opening 412a of implant 440. A locking sleeve 660 that includes two distal protrusions 661a, 661b surrounds sleeve 670.

Figure 31A:
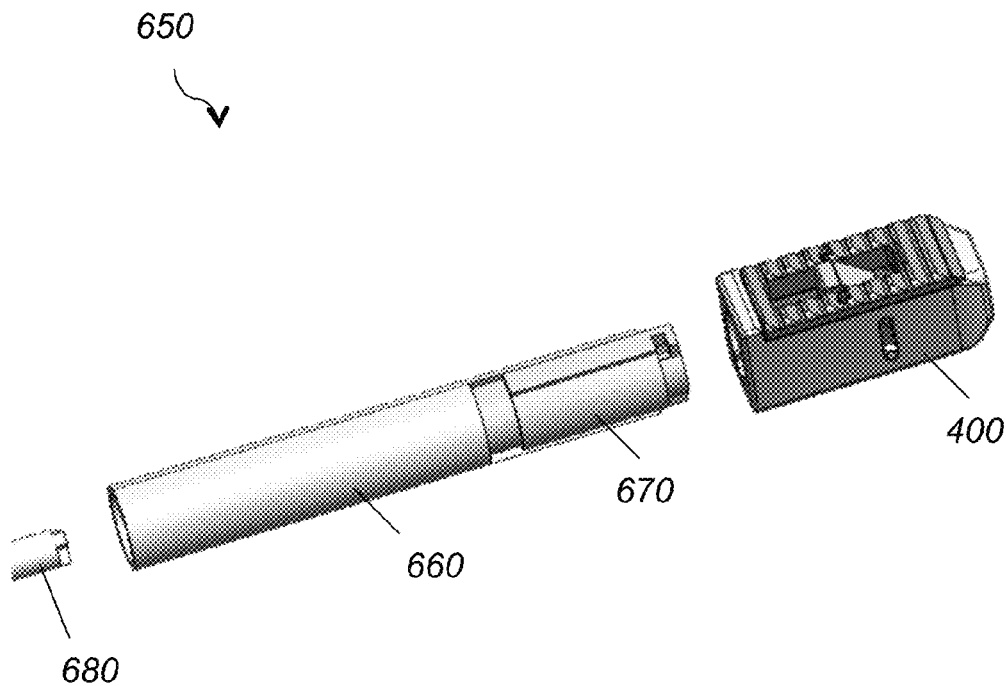
FIG. 31A is a perspective view of an inserter tool for the intervertebral implant of FIG. 17A.
Figure 31B:
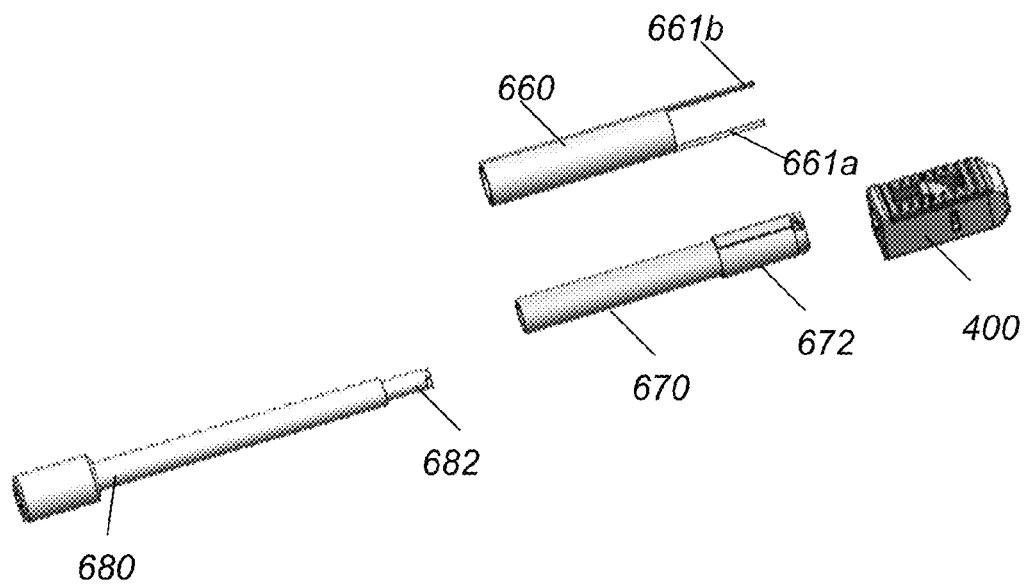
FIG. 31B is an exploded view of the inserter tool of FIG. 31A.
Figure 31C:
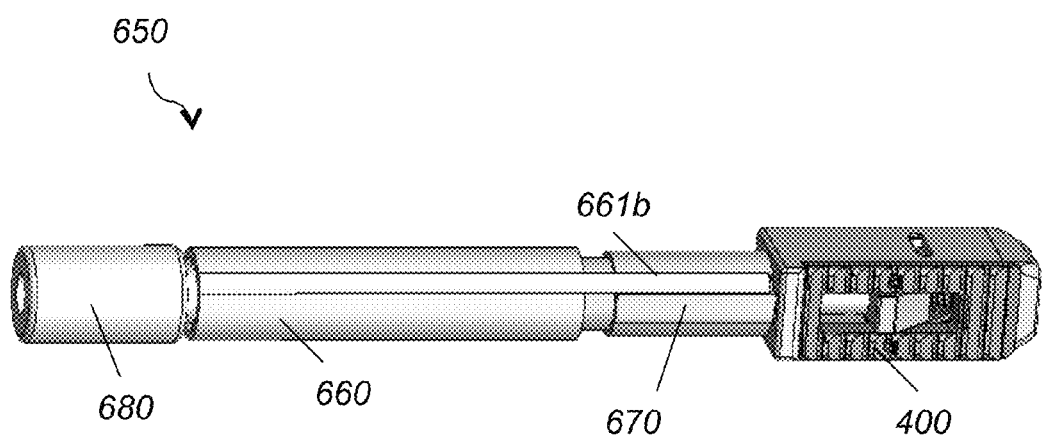
FIG. 31C is a top view of the inserter tool of FIG. 31A in the "inserted" position.
Figure 31D:
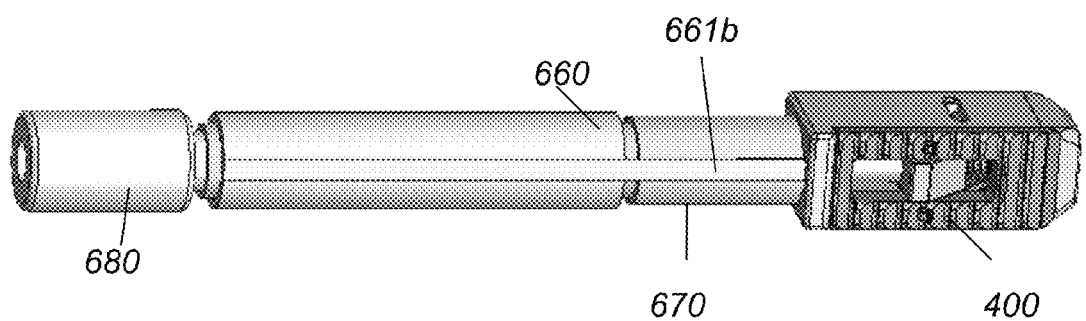
FIG. 31D is a top view of the inserter tool of FIG. 31A in the "locked" position.
Figure 33:
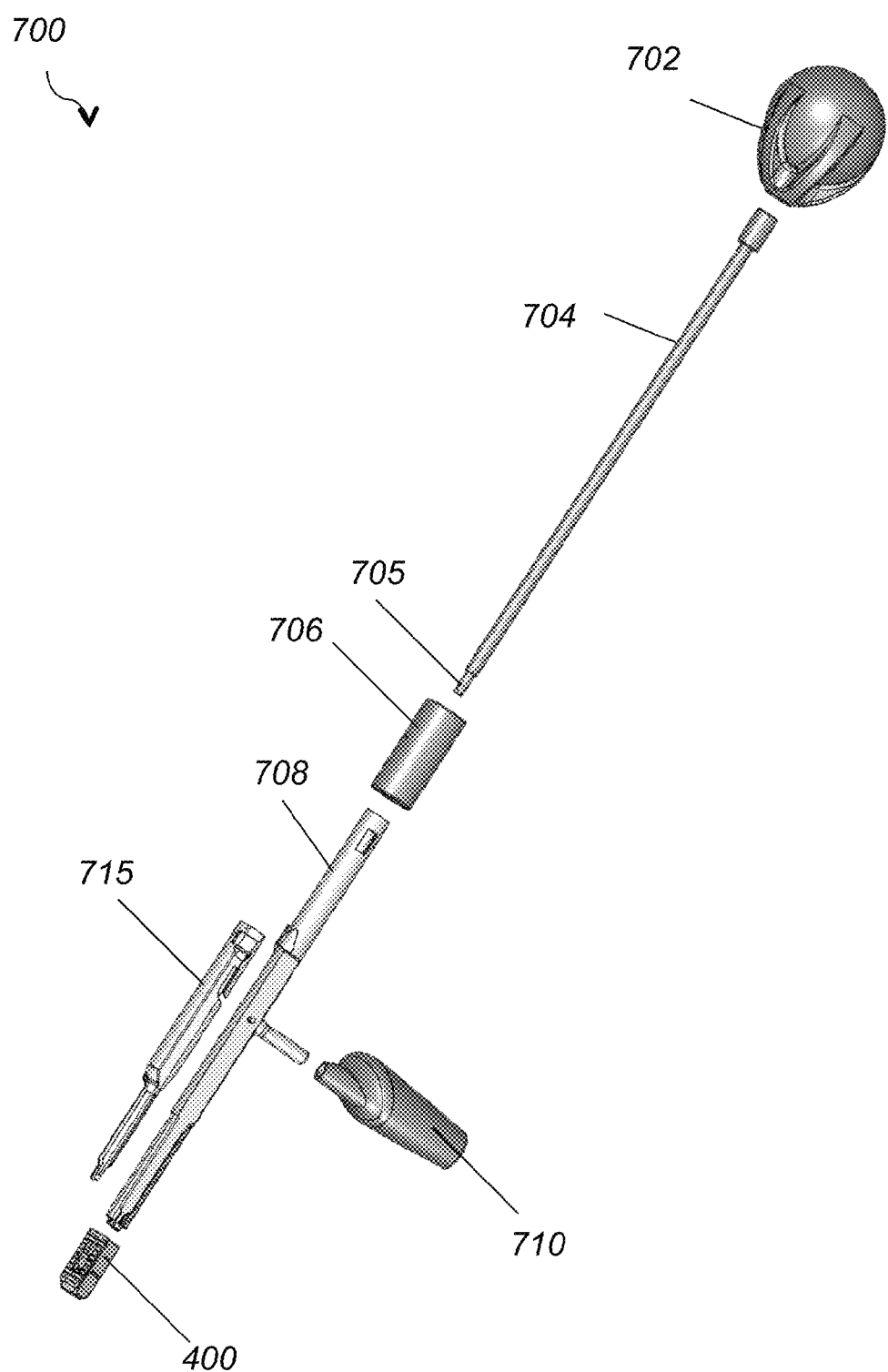
FIG. 33 and FIG. 34 are exploded views of another embodiment of an inserter tool for the intervertebral implant of FIG. 17A.
Figure 34:
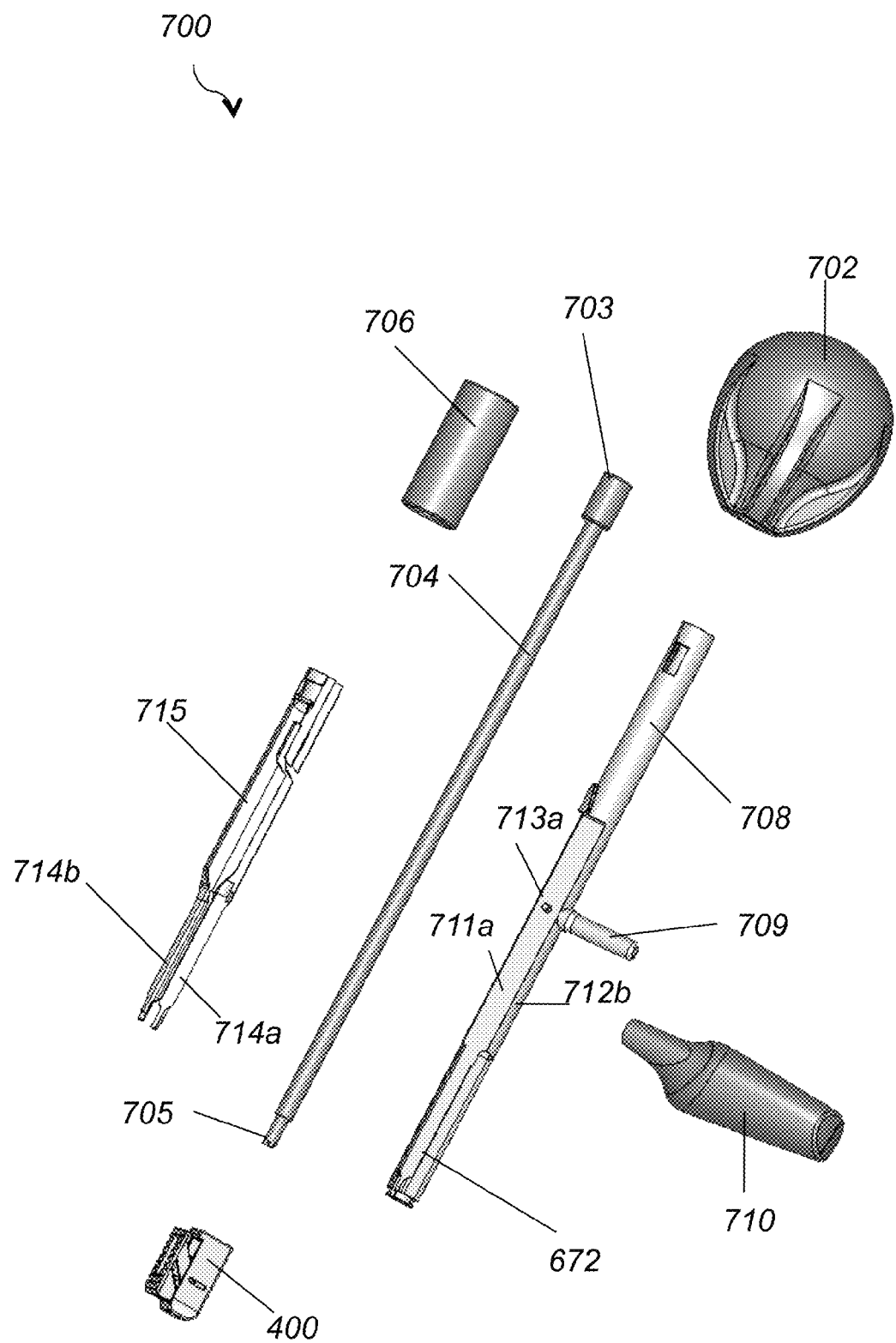

In operation, elongated shaft 680 is inserted into opening 412a and the distal tip 682 engages the front 441b of the actuator rod. Next, front component 672 of sleeve 670 is inserted into opening 412a so that protrusions 672a, 672b are aligned with recesses 673a, 673b, as shown in FIG. 31C, and then sleeve 670 is rotated to move protrusions 672a, 672b to the left or right of recesses 673a, 673b. Next, the locking sleeve 660 is moved forward so that the distal protrusions 661a, 661b are inserted into the recesses 673a, 673b, as shown in FIG. 31D, and thereby the inserter 600 is locked onto implant 400 while the elongated shaft 680 can still be rotated to move the actuator rod.

Referring to FIG. 33-FIG. 36B, inserter 700 includes an elongated cylindrical shaft 704, a sleeve component 708, a locking sleeve 714, an asymmetrical handle 710, a collar 706, and a spherical handle 702. Cylindrical shaft 704 terminates in a distal tip 705 and has a proximal end 703 that connects to the spherical handle 702. Tip 705 complements the shape of front 441b of the actuator rod 440 used in the intervertebral implant 400 of FIG. 26. In this example, tip 705 has a tri-lobe shape, as shown in FIG. 32A. Sleeve component 708 surrounds shaft 704 and has a front component 672 that is sized to surround the front 441b of actuator rod 440, and is shaped to complement the shape of the front opening 412a of the intervertebral implant 400, as shown in FIG. 32B and FIG. 32C. In this example, front component 672 has top and bottom protrusions 672a, 672b that match top and bottom recesses 673a, 673b, respectively, in the front opening 412a of implant 440. Sleeve component 708 is designed to enable a quarter turn rotation and has a portion with two opposite flat surfaces 711a, 711b and two opposite curve surfaces 712a, 712b. Flat surfaces 711a, 711b include pins 713a, 713b, respectively. Sleeve component 708 also includes an extension rod 709 that connects to the asymmetrical handle 710. Locking sleeve 715 includes two distal protrusions 714a, 714b and surrounds the lower portion of sleeve 708.

Figure 35A:
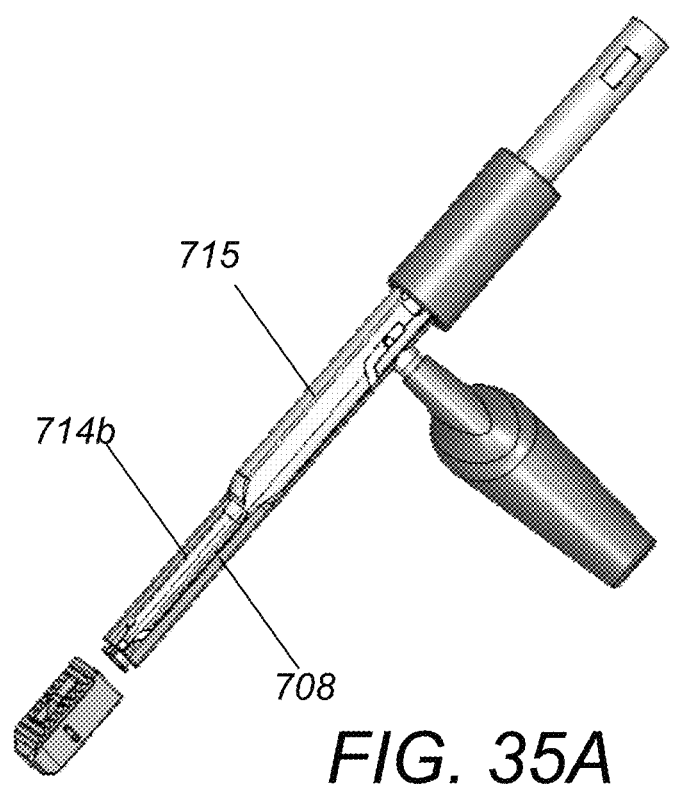
FIG. 35A is a perspective view of the inserter tool of FIG. 33 in the "detached" configuration.
Figure 35B:
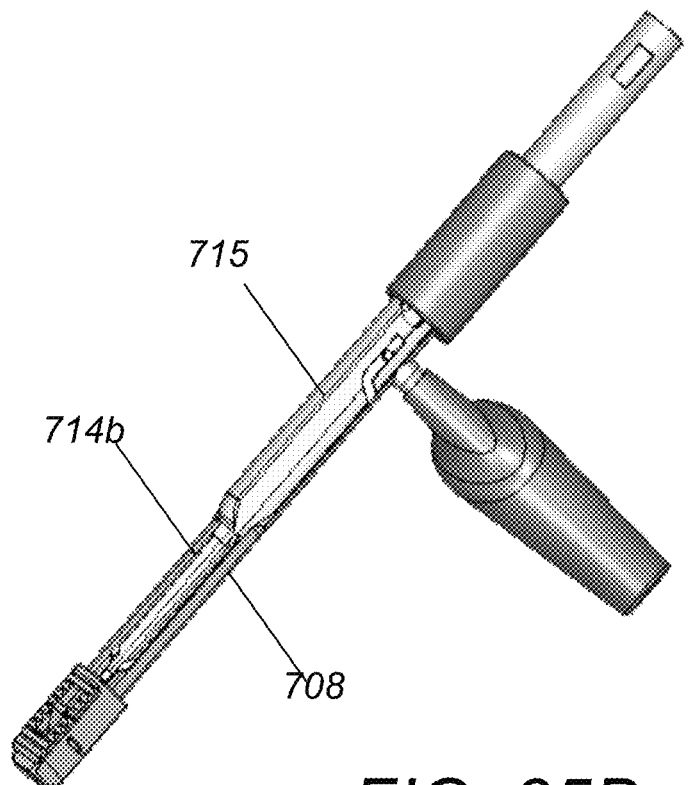
FIG. 35B is a perspective view of the inserter tool of FIG. 33 in the "inserted" configuration.
Figure 36A:
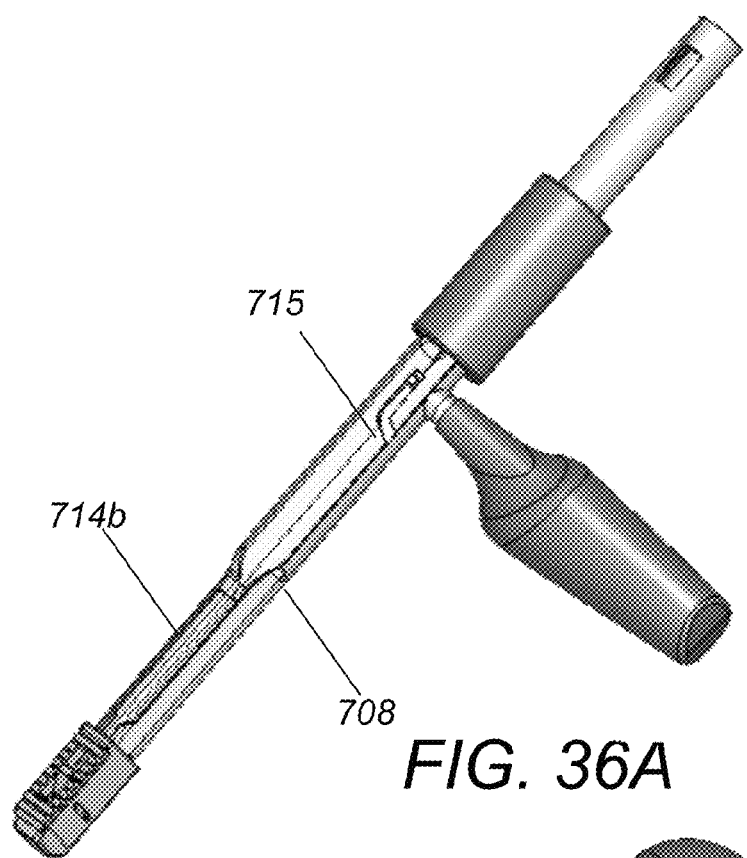
FIG. 36A is a perspective view of the inserter tool of FIG. 33 in the "locked" configuration.
Figure 36B:
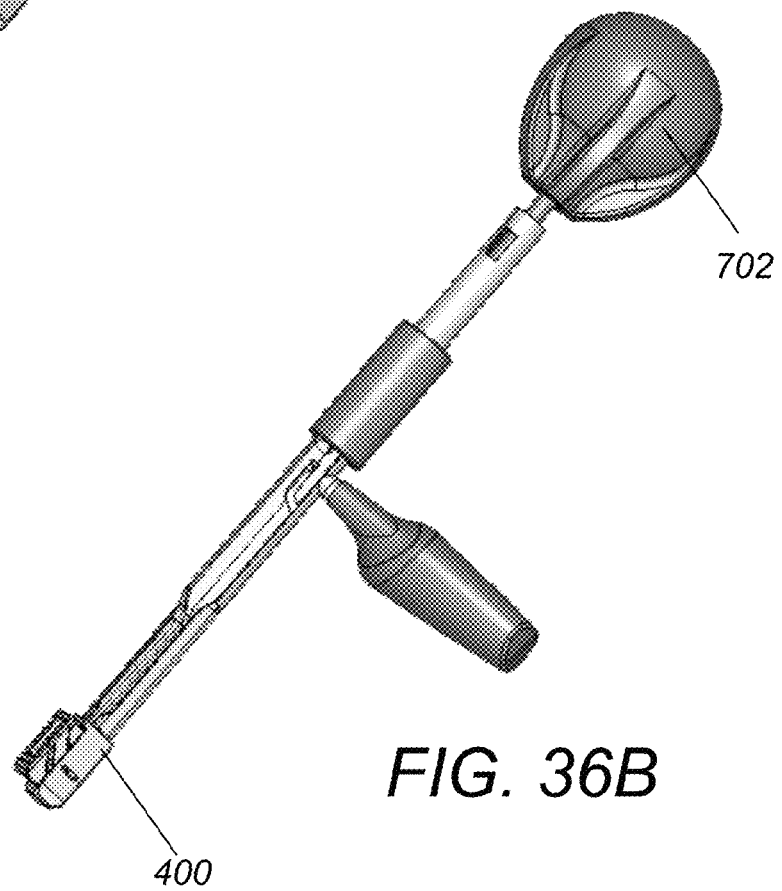
FIG. 36B is a perspective view of the inserter tool of FIG. 33 in the "expanded" configuration.
Figure 39:
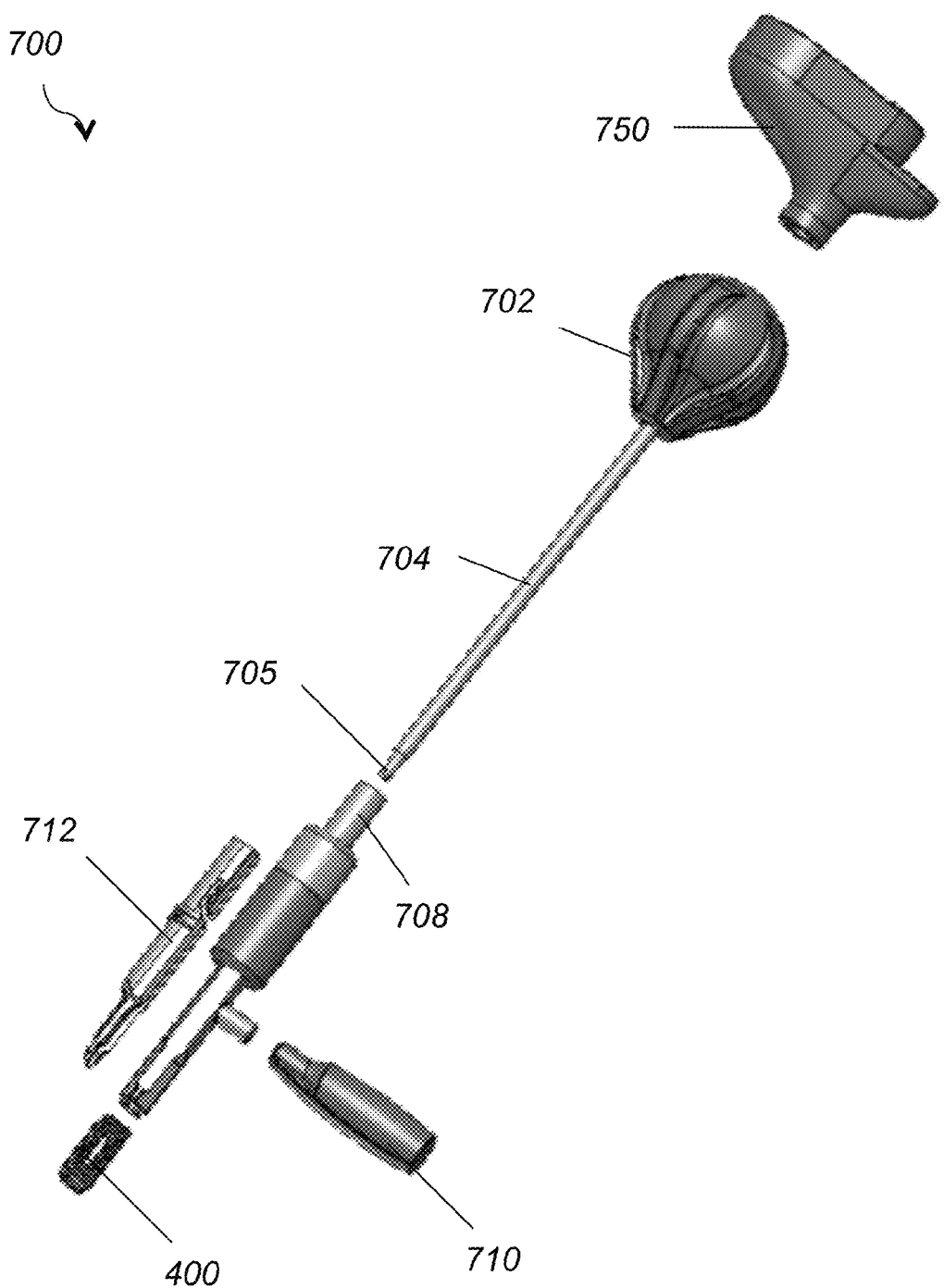
FIG. 39 is an exploded view of another embodiment of an inserter tool for the intervertebral implant of FIG. 17A.

In operation, elongated shaft 704 is inserted into opening 412a and the distal tip 705 engages the front 441b of the actuator rod. Next, front component 672 of sleeve 708 is inserted into opening 412a so that protrusions 672a, 672b are aligned with recesses 673a, 673b, as shown in FIG. 35B, and then sleeve 708 is rotated to move protrusions 672a, 672b to the left or right of recesses 673a, 673b. Next, the locking sleeve 715 is moved forward by rotating collar 706 by a quarter turn so that the distal protrusions 714a, 714b are inserted into the recesses 673a, 673b, as shown in FIG. 36A, and thereby the inserter 700 is locked onto implant 400 while the elongated shaft 704 can still be rotated to move the actuator rod and expand the implant 400, as shown in FIG. 36B. Inserter 700 may further include a funnel 750 used to feed bone graft material into an opening of the intervertebral implant 400, as shown in FIG. 39.

Several embodiments of the present invention have been described. Nevertheless, it will be understood that various modifications may be made without departing from the spirit and scope of the invention. Accordingly, other embodiments are within the scope of the following claims.

What is claimed is:

1. An expandable intervertebral implant comprising:
a base body comprising a front end and a back end, first and second side portions connecting the front end and the back end;
a top endplate configured to be placed onto an open top of the base body and to expand upward, wherein said top endplate comprises a plate, first and second side protrusions extending vertically downward from first and second sides of the plate, respectively, first and second protrusions comprising inclined surfaces and extending obliquely downward from a first end of the plate and third and fourth protrusions comprising a triangular shape with at least one inclined surface and extending downward from a second end of the plate;
a center component comprising first and second sides, and wherein each of said first and second sides of the center component comprises first and second protrusions comprising inclined surfaces and wherein the center component is configured to be placed within the base body and to interface with the top endplate and to move longitudinally forward or backward within the base body, thereby causing the top endplate to expand upwards or move downward, respectively;
wherein said first and second side protrusions of the top endplate interdigitate with complementary first and second recesses formed on the first and second side portions of the base body, respectively;
wherein the first and second protrusions of the top endplate interface with the first protrusions on each side of the center component, respectively; and
wherein the third and fourth protrusions of the top endplate interface with the second protrusions on each side of the center component, respectively.

2. The expandable intervertebral implant of claim 1, wherein the center component further comprises a threaded through-opening in a front portion thereof, and wherein said first and second protrusions of the center component comprise inclined surfaces.

3. The expandable intervertebral implant of claim 2, further comprising an actuator rod comprising an outer threaded surface and being configured to be threaded into the threaded through-opening in the front portion of the center component.

4. The expandable intervertebral implant of claim 3, wherein threading the actuator rod into the threaded through-opening in the front portion of the center component moves the center component longitudinally forward into the base body, and causes the inclined surfaces of the first and second protrusions of the top endplate to slide upward onto the inclined surfaces of the first protrusions of the first and second sides of the center component, respectively, and the inclined surfaces of the third and fourth protrusions of the top endplate to slide upward onto the inclined surfaces of the second protrusions of the first and second sides of the center component, respectively, thereby causing the top endplate to expand upward.

5. The expandable intervertebral implant of claim 3, wherein threading the actuator rod out of the threaded through-opening in the front portion of the center component moves the center component longitudinally backward out of the base body, and causes the inclined surfaces of the first and second protrusions of the top endplate to slide downward onto the inclined surfaces of the first protrusions of the first and second sides of the center component, respectively, and the inclined surfaces of the third and fourth protrusions of the top endplate to slide downward onto the inclined surfaces of the second protrusions of the first and second sides of the center component, respectively, thereby causing the top endplate to move downward.

6. The expandable intervertebral implant of claim 1, wherein the first and second recesses on the first and second side portions of the base body comprise rectangular-shape.

7. The expandable intervertebral implant of claim 6, wherein the first and second side portions of the base body further comprise triangular-shaped third and fourth recesses configured to complement and receive third and fourth side protrusions of the top endplate, respectively.

8. The expandable intervertebral implant of claim 1, further comprising removable pins configured to be inserted into openings formed in the first and second side portions of the base body and into openings formed in the center component, wherein the openings formed in the first and second side portions are coaxial with the openings formed in the center component.

9. The expandable intervertebral implant of claim 3, wherein the actuator comprises a slotted front end, sized and shaped to receive a key.

10. The expandable intervertebral implant of claim 1, wherein the base body further comprises a base plate and wherein the first and second side portions extend upward from the base plate.

11. The expandable intervertebral implant of claim 10, wherein an outer surface of the base plate comprises one of teeth, ridges, grooves or protrusions.

12. The expandable intervertebral implant of claim 1, wherein an outer surface of the top endplate comprises one of teeth, ridges, grooves or protrusions.

13. The expandable intervertebral implant of claim 1, further comprising a bottom endplate configured to be placed onto an open bottom of the base body and to expand downward, wherein said bottom endplate comprises a plate, first and second side protrusions extending vertically upward from first and second sides of the plate, respectively, first and second protrusions comprising inclined surfaces and extending obliquely upward from a first end of the plate and third and fourth protrusions comprising a triangular shape with at least one inclined surface and extending upward from a second end of the plate; and wherein the center component is also configured to interface with the bottom endplate and to move longitudinally forward or backward within the base body, thereby causing the bottom endplate to expand downward or move upward, respectively.

14. The expandable intervertebral implant of claim 13, wherein the center component comprises a threaded through-opening in a front portion, first and second sides, and wherein each of said first and second sides of the center component comprises first and second protrusions comprising upper and lower parallel inclined surfaces and a third protrusion connecting the first and second protrusions.

15. The expandable intervertebral implant of claim 14, further comprising an actuator rod comprising an outer threaded surface and being configured to be threaded into the threaded through-opening in the front portion of the center component.

16. The expandable intervertebral implant of claim 15, wherein threading the actuator rod into the threaded through-opening in the front portion of the center component moves the center component longitudinally forward into the base body, and causes the inclined surfaces of the first and second protrusions of the top endplate to slide upward onto the upper inclined surfaces of the first protrusions of the first and second sides of the center component, respectively, and the inclined surfaces of the third and fourth protrusions of the top endplate to slide upward onto the upper inclined surfaces of the second protrusions of the first and second sides of the center component, respectively, thereby causing the top endplate to expand upward.

17. The expandable intervertebral implant of claim 16, wherein threading the actuator rod into the threaded through-opening in the front portion of the center component moves the center component longitudinally forward into the base body, and also causes the inclined surfaces of the first and second protrusions of the bottom endplate to slide downward onto the lower inclined surfaces of the first protrusions of the first and second sides of the center component, respectively, and the inclined surfaces of the third and fourth protrusions of the bottom endplate to slide downward onto the lower inclined surfaces of the second protrusions of the first and second sides of the center component, respectively, thereby causing the bottom endplate to expand downward.

18. The expandable intervertebral implant of claim 1, wherein the plate of the top endplate comprises a longitudinally extending central opening and first and second openings positioned on either side of the longitudinally extending central opening.

19. The expandable intervertebral implant of claim 1, wherein the base body further comprises first and second recesses formed on outer surfaces of the first and second side portions thereof, respectively, and wherein the first and second recesses are configured to receive grasping protrusions of an inserter tool.

20. The expandable intervertebral implant of claim 1, wherein the back end of the base body comprises a through-opening configured to receive bone graft material.

21. The expandable intervertebral implant of claim 3, wherein the actuator comprises a front end with a tri-lobe shaped slot configured to receive a tri-lobe shaped tip of an inserter tool.

* * * * *